US012594160B2

(12) United States Patent (10) Patent No.: US 12,594,160 B2
Ratz et al. (45) Date of Patent: Apr. 7, 2026

(54) PROSTHETIC HEART VALVE

(71) Applicant: inQB8 Medical Technologies, LLC, Wilmington, DE (US)

(72) Inventors: J. Brent Ratz, Winchester, MA (US); Arshad Quadri, West Hartford, CT (US); Christopher Stivers, Somerville, MA (US)

(73) Assignee: inQB8 Medical Technologies, LLC, Burlington, MA (US)

( * ) Notice: Subject to any disclaimer, the term of this patent is extended or adjusted under 35 U.S.C. 154(b) by 267 days.

(21) Appl. No.: 17/458,914

(22) Filed: Aug. 27, 2021

(65) Prior Publication Data

US 2022/0087816 A1 Mar. 24, 2022

Related U.S. Application Data

(60) Provisional application No. 63/082,970, filed on Sep. 24, 2020, provisional application No. 63/072,022, filed on Aug. 28, 2020.

(51) Int. Cl.
*A61F 2/24* (2006.01)

(52) U.S. Cl.
CPC .......... *A61F 2/2418* (2013.01); *A61F 2/2427* (2013.01)

(58) Field of Classification Search
CPC .................................................... A61F 2/2418
See application file for complete search history.

(56) References Cited

U.S. PATENT DOCUMENTS

| | | | |
|---|---|---|---|
| 9,585,751 | B2 | 3/2017 | Morriss et al. |
| 9,987,132 | B1 | 6/2018 | Hariton et al. |
| 10,105,223 | B2 | 10/2018 | Savage et al. |
| 10,420,642 | B2 | 9/2019 | Gloss et al. |
| 10,617,519 | B2 | 4/2020 | Vidlund et al. |
| 10,687,939 | B2 | 6/2020 | Cooper et al. |

(Continued)

FOREIGN PATENT DOCUMENTS

| | | |
|---|---|---|
| EP | 2777617 A1 | 9/2014 |
| JP | 2014-522678 A1 | 9/2014 |

(Continued)

OTHER PUBLICATIONS

International Search Report and Written Opinion for International Application No. PCT/US2021/047906 mailed Dec. 6, 2021.

(Continued)

*Primary Examiner* — Suba Ganesan
(74) *Attorney, Agent, or Firm* — Wolf, Greenfield & Sacks, P.C.

(57) ABSTRACT

Described herein are prosthetic heart valves and methods for improving the functionality of native heart valves. An exemplary prosthetic heart valve may include one or more support structures, in which at least one support structure defines an elongate central passageway having a longitudinal. The prosthetic heart valve may include a plurality of leaflet elements attached to the at least one support structure and disposed within the elongate central passageway for control of blood flow through the elongate central passageway. The at least one support structure may be configured to biodynamically fix the prosthetic heart valve to native leaflets of a native heart valve of a heart.

24 Claims, 46 Drawing Sheets

(56) References Cited

U.S. PATENT DOCUMENTS

| | | | |
|---|---|---|---|
| 11,324,594 B2 | 5/2022 | Ratz et al. | |
| 11,602,433 B2 | 3/2023 | Ratz et al. | |
| 2002/0055775 A1 | 5/2002 | Carpentier et al. | |
| 2004/0127981 A1 | 7/2004 | Rahdert et al. | |
| 2005/0010287 A1 | 1/2005 | Macoviak et al. | |
| 2007/0088431 A1 | 4/2007 | Bourang et al. | |
| 2008/0071368 A1 | 3/2008 | Tuval et al. | |
| 2009/0005863 A1 | 1/2009 | Goetz et al. | |
| 2010/0049313 A1 | 2/2010 | Alon et al. | |
| 2012/0035722 A1 | 2/2012 | Tuval | |
| 2012/0203336 A1 | 8/2012 | Annest | |
| 2013/0211508 A1 | 8/2013 | Lane et al. | |
| 2013/0325110 A1 | 12/2013 | Khalil et al. | |
| 2013/0325114 A1 | 12/2013 | McLean et al. | |
| 2014/0222136 A1 | 8/2014 | Geist et al. | |
| 2014/0277390 A1* | 9/2014 | Ratz | A61F 2/2418 623/1.26 |
| 2014/0277422 A1 | 9/2014 | Ratz et al. | |
| 2014/0277427 A1 | 9/2014 | Ratz et al. | |
| 2014/0316518 A1 | 10/2014 | Kheradvar et al. | |
| 2014/0379076 A1 | 12/2014 | Vidlund et al. | |
| 2015/0157477 A1 | 6/2015 | Shahriari | |
| 2015/0320556 A1* | 11/2015 | Levi | A61F 2/2427 29/515 |
| 2015/0342733 A1 | 12/2015 | Alkhatib et al. | |
| 2015/0351904 A1 | 12/2015 | Cooper et al. | |
| 2016/0008131 A1 | 1/2016 | Christianson et al. | |
| 2016/0095700 A1 | 4/2016 | Righini | |
| 2016/0310268 A1 | 10/2016 | Oba et al. | |
| 2017/0056166 A1* | 3/2017 | Ratz | A61F 2/2418 |
| 2017/0071733 A1 | 3/2017 | Ghione et al. | |
| 2017/0095328 A1 | 4/2017 | Cooper et al. | |
| 2017/0100236 A1 | 4/2017 | Robertson et al. | |
| 2017/0128199 A1* | 5/2017 | Gurovich | A61F 2/2409 |
| 2017/0216026 A1* | 8/2017 | Quill | A61F 2/2427 |
| 2017/0281341 A1* | 10/2017 | Lim | A61F 2/2418 |
| 2017/0319333 A1 | 11/2017 | Tegels et al. | |
| 2018/0021129 A1 | 1/2018 | Peterson et al. | |
| 2018/0028177 A1 | 2/2018 | Van Oepen et al. | |
| 2018/0055629 A1* | 3/2018 | Oba | A61L 27/3625 |
| 2018/0289485 A1 | 10/2018 | Rajagopal et al. | |
| 2018/0303612 A1* | 10/2018 | Pasquino | A61F 2/2448 |
| 2019/0008639 A1 | 1/2019 | Landon et al. | |
| 2019/0038405 A1 | 2/2019 | Iamberger et al. | |
| 2019/0069997 A1 | 3/2019 | Ratz et al. | |
| 2019/0083245 A1 | 3/2019 | Hariton et al. | |
| 2019/0083263 A1* | 3/2019 | Hariton | A61F 2/2445 |
| 2020/0038184 A1 | 2/2020 | McLean | |
| 2020/0155305 A1 | 5/2020 | McLean | |
| 2020/0205978 A1 | 7/2020 | Padala et al. | |
| 2020/0306044 A1 | 10/2020 | Ratz et al. | |
| 2021/0113332 A1 | 4/2021 | Benichou et al. | |
| 2021/0298902 A1 | 9/2021 | Ratz et al. | |
| 2021/0378822 A1 | 12/2021 | Ratz et al. | |
| 2023/0263631 A1 | 8/2023 | Ratz et al. | |
| 2024/0008984 A1 | 1/2024 | Ratz et al. | |

FOREIGN PATENT DOCUMENTS

| | | |
|---|---|---|
| JP | 2016-512753 A | 5/2016 |
| JP | 2017-148551 A | 8/2017 |
| WO | WO 2018/213209 A1 | 11/2018 |
| WO | 2019/010370 A1 | 1/2019 |
| WO | WO 2019/010303 A1 | 1/2019 |

OTHER PUBLICATIONS

International Search Report and Written Opinion for International Application No. PCT/US2021/049004 mailed Dec. 3, 2021.
International Search Report and Written Opinion for International Application No. PCT/US2020/024765 mailed Jun. 15, 2020.
International Preliminary Report on Patentability (Chapter II) for International App. No. PCT/US2020/024765 dated Sep. 2, 2021.
Extended European Search Report for EP Application No. 20778511.4 dated Mar. 17, 2023.
U.S. Appl. No. 16/836,882, filed Mar. 31, 2020, Ratz et al.
U.S. Appl. No. 17/346,127, filed Jun. 11, 2021, Ratz et al.
U.S. Appl. No. 17/346,711, filed Jun. 14, 2021, Ratz et al.
Extended European Search Report for EP Application No. 21862806.3 dated Aug. 26, 2024.
Extended European Search Report for EP Application No. 21865164.4 dated Sep. 20, 2024.

* cited by examiner

△ LENGTH = 5.5

① Pre-cut opening

2600

>>

③ 3 Separate ends

2604 create braid from tops of fabric slide through hole @ carabiner braid

④

2606 sutures

>> 1 end opening

② 2 separate ends

2602 fold over + suture >>> together sutures opening sutures

3702

3704

PLEATED
PUFFY LAYER     3902

RV
ARMS

3902

RV ARMS

RIB CAGE

AV RECEIVED
AT TROUGH
OF RV ARM

3902

WHEN "RIB
CAGE" EXPANDS
IT FORCES
PUFFY LAYER
OPEN AND
EXPANDS
PLEATS

CYLINDER

NATIVE
LEAFLET
IN
BETWEEN

5300

5300

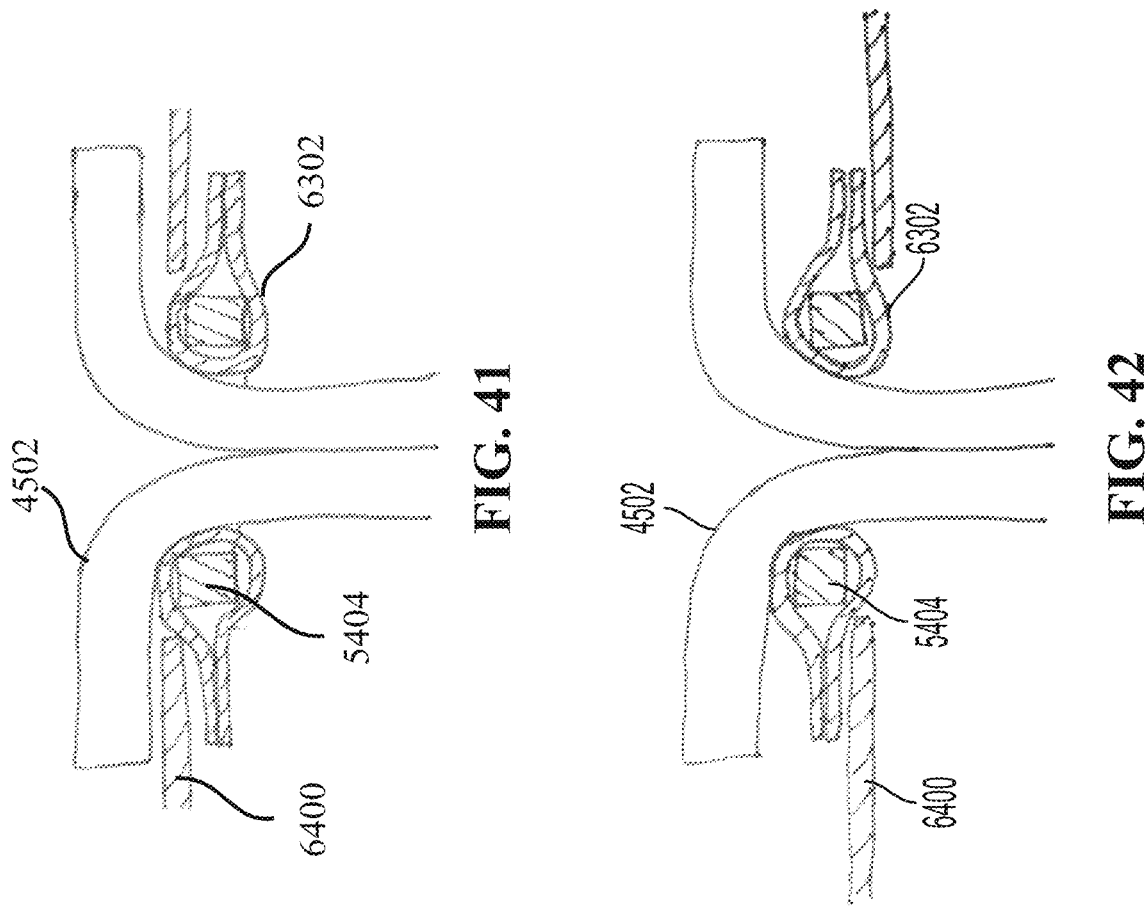
FIG. 41
FIG. 42
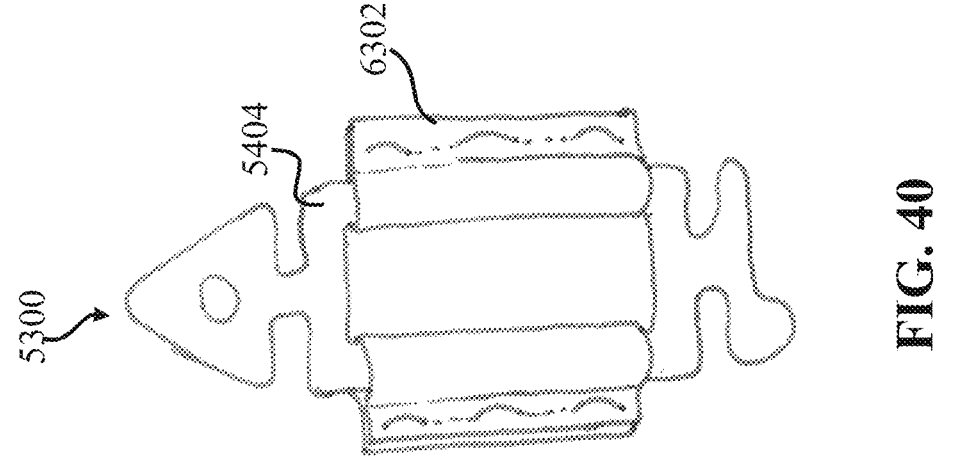
FIG. 40

7600

7702

7602

7600

EXPAND INTO
COMM GAPS

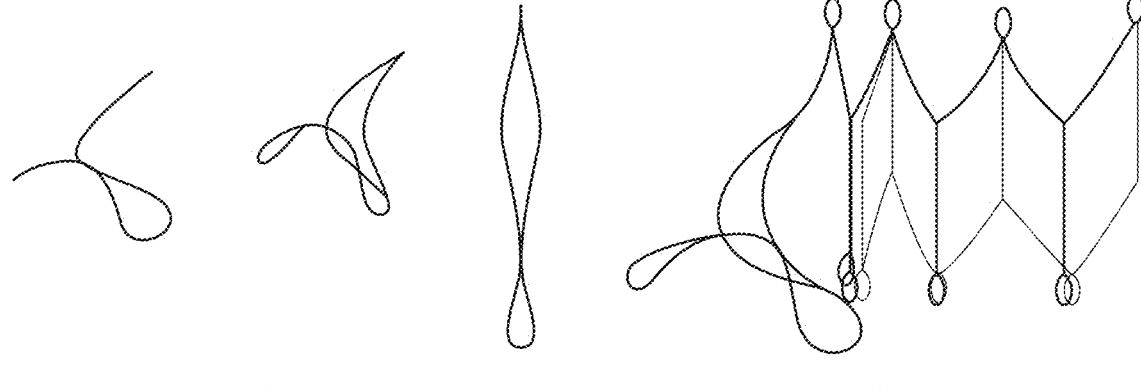
FIG. 57          FIG. 58
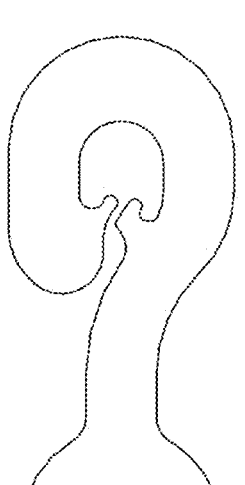
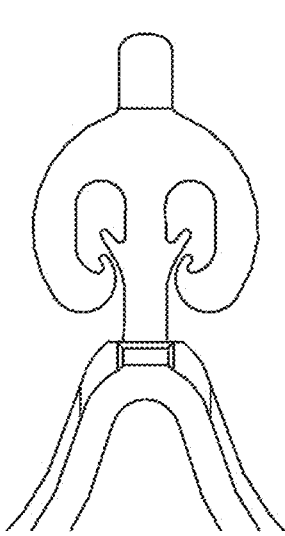
FIG. 59A          FIG. 59B ventricular cover if annular-
directed arms extend radially
beyond distal portion of RV "up"
arms
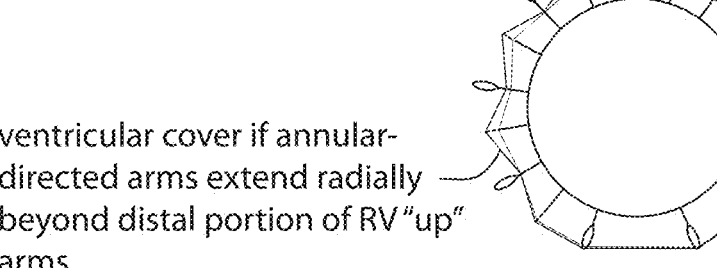
FIG. 62A
ventricular cover if annular-
directed arms extend radially
beyond distal portion of RV "up"
arms
FIG. 62B
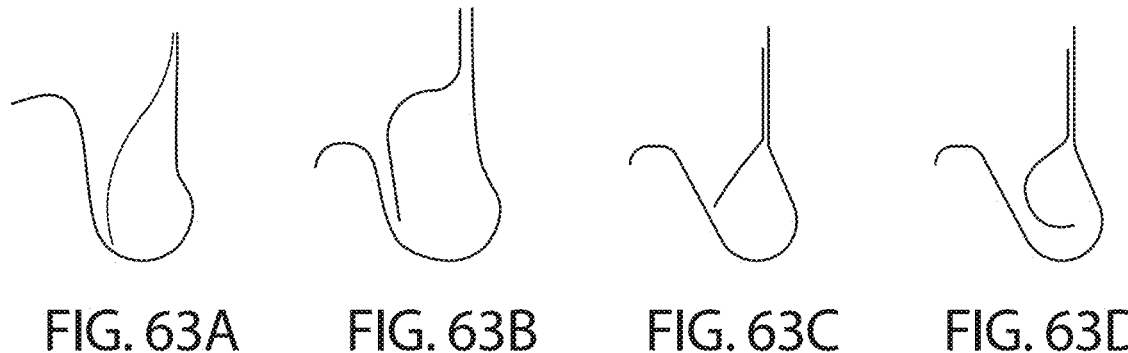
FIG. 63A        FIG. 63B        FIG. 63C        FIG. 63D

PROSTHETIC HEART VALVE

RELATED APPLICATIONS

This Application claims priority under 35 U.S.C. 119(e) to U.S. Application Ser. No. 63/082,970, filed Sep. 24, 2020, entitled "PROSTHETIC HEART VALVE". This Application claims priority under 35 USC 119(e) to U.S. Application Ser. No. 63/072,022, filed Aug. 28, 2020, entitled "PROSTHETIC HEART VALVE". The entire contents of these applications are incorporated herein by reference in their entirety.

TECHNICAL FIELD

The present disclosure generally relates to implantable cardiac devices and, more particularly, to prosthetic tricuspid valves.

BACKGROUND

Significant advancements have been made in the transcatheter treatment of heart valve disease. Initial clinical efforts focused on the pulmonary valve and were quickly followed by devices focused on the percutaneous replacement of the aortic valve to treat Aortic Stenosis. In parallel, there were numerous programs that attempted to address Mitral Regurgitation through transcatheter repair technologies and later through transcatheter mitral valve replacement.

Tricuspid valve disease is a condition in which the tricuspid valve located between the right ventricle and the right atrium of the heart of does not function properly. There are multiple forms of tricuspid valve disease, including, for example, tricuspid valve regurgitation, in which blood flows backwards from the right ventricle into the right atrium, tricuspid valve stenosis, in which the tricuspid valve is narrowed, thereby decreasing blood flow from the right atrium to the right ventricle, and tricuspid atresia, which is congenital non-formation or mal-formation of the tricuspid valve, thereby blocking or decreasing blood flow from the right atrium to the right ventricle. Tricuspid valve disease has been largely ignored as a "lesser" valve disease, relative to Aortic Stenosis (greatest level of mortality) and Mitral Regurgitation (greatest prevalence).

There are currently few tricuspid-specific prosthetic tricuspid valves. In many cases tricuspid valve defects have been treated using repurposed prosthetic aortic and mitral valves. Prosthetic aortic and mitral valves that have been repurposed for use in the tricuspid valve rigidly fix by asserting pressure on the native annulus of the tricuspid valve, making the prosthetic valve immobile. Because of the tricuspid valve's proximity to conductive regions of the heart, this rigid fixation of a prosthetic valve within the tricuspid valve may lead to heart block and/or other conduction abnormalities.

SUMMARY

Accordingly, there is a need for prosthetic valves specifically configured for the repair of the tricuspid valve, as replacement of the tricuspid presents unique issues. In addition, innovative aspects of a tricuspid-specific prosthetic valve may offer improvements to heart valves configured for other atrio-ventricular valves (i.e., mitral valve).

Described herein are embodiments of a prosthetic heart valve configured for tricuspid valve repair.

In one aspect, the disclosure features a prosthetic heart valve including one or more support structures, wherein at least one support structure defines an elongate central passageway having an longitudinal axis and wherein the at least one support structure is asymmetrical, from at least one perspective, about the longitudinal axis; and a plurality of leaflet elements attached to the at least one support structure and disposed within the elongate central passageway for control of blood flow through the elongate central passageway, in which the at least one support structure is configured to biodynamically fix the prosthetic heart valve to native leaflets of a native heart valve of a heart.

Various embodiments of the prosthetic heart valve may include one or more of the following features.

The at least one support structure may be configured to biodynamically fix the prosthetic heart valve to the native leaflets such that the at least one support structure is moveable within a native annulus of the native heart valve responsive to changes in pressure on one or more sides of the native heart valve. The at least one support structure may include a cylindrical portion comprising an atrial end and a ventricular end, and the elongate central passageway is defined by the cylindrical portion of the at least one support structure. The at least one support structure may include an atrial set of arms, each arm of the atrial set of arms comprises a proximal atrial segment that is proximal to the cylindrical portion and a distal atrial segment that is distal to the cylindrical portion, at least one of a size, a shape, or an angle of a first atrial arm of the atrial set of arms is different from a corresponding one of a size, a shape, or an angle of a second atrial arm of the atrial set of arms. The angle may be an angle of the distal atrial segment and/or proximal atrial segment to the longitudinal axis.

The size of the first atrial arm may be greater than the size of the second atrial arm. The first atrial arm may have a first length in a direction parallel to the longitudinal axis and the second atrial arm may have a second length in the direction parallel to the longitudinal axis, and the first length may be greater than the second length. The first length may be greater than the second length when the prosthetic heart valve is implanted in the heart. The distal atrial segment of the first atrial arm has a first distal end at a first distance from the longitudinal axis and the distal atrial segment of the second atrial arm has a second distal end at a second distance from the longitudinal axis, and the distal atrial segment of the first atrial arm extends relative to the longitudinal axis such that the first distance is less than the second distance.

The prosthetic heart valve may include an atrial cover comprising a plurality of distal atrial covers configured to be disposed adjacent to the distal atrial segments of the atrial set of arms. Each distal atrial cover may include one or more pleats such that the distal atrial cover is configured to expand or contract as a corresponding one of the atrial set of arms increases or decreases in length. The atrial set of arms may be attached to the ventricular end of the cylindrical portion of the at least one support structure.

The at least one support structure may include a ventricular set of arms, each arm of the ventricular set of arms comprises a proximal ventricular segment that is proximal to the cylindrical portion and a distal ventricular segment that is distal to the cylindrical portion, at least one of a size, a shape, or an angle of a first ventricular arm is different from a corresponding one of a size, a shape, or an angle of a second ventricular arm. The angle may be an angle of the distal atrial segment and/or the proximal atrial segment to the longitudinal axis.

The size of the first ventricular arm may be greater than the size of the second ventricular arm. The first ventricular arm has a first length in a direction parallel to the longitudinal axis and the second ventricular arm has a second length in the direction parallel to the longitudinal axis, and the first length is greater than the second length. The first length may be greater than the second length when the prosthetic heart valve is implanted in the heart. In an implanted configuration, a first subset of the ventricular set of arms is proximate to a ventricular side of a first one of the native leaflets, and a second subset of the ventricular set of arms is proximate to an atrial side of a second one of the native leaflets. In the implanted configuration, at least one arm of a third subset of the ventricular set of arms is proximate to at least one of: a commissure of the native heart or an atrial side of the first native leaflet.

At least one arm of the third subset may have a first length in a direction parallel to the longitudinal axis and another arm of the third subset may have a second length in a direction parallel to the longitudinal axis, and the first length is greater than the second length. Each arm of the first subset may be configured such that the arms of the first subset, when in the implanted configuration, do not contact a native annulus of the heart, thereby reducing trauma to the heart. A ventricular cover may be disposed adjacent to a perimeter of the proximal ventricular segments, in which the perimeter is opposite the cylindrical portion. A ventricular cover may be disposed adjacent to the proximal ventricular segments of the ventricular set of arms. A portion of the ventricular cover may extend to be disposed adjacent to the distal ventricular segments of a subset of the ventricular set of arms. The ventricular set of arms may be attached to the atrial end of the cylindrical portion of the at least one support structure. The cylindrical portion of the at least one support structure may be radially collapsible for transcatheter implantation.

In another aspect, the disclosure features a method for improving a functionality of a native heart valve of a heart. The method may include positioning, within the native heart valve, a prosthetic heart valve including one or more support structures, in which at least one support structure defines an elongate central passageway having a longitudinal axis and the at least one support structure is asymmetrical, from at least one perspective, about the longitudinal axis; and a plurality of leaflet elements attached to the at least one support structure and disposed within the elongate central passageway for control of blood flow through the elongate central passageway, in which the at least one support structure biodynamically fixes the prosthetic heart valve to native leaflets of the native heart valve.

In another aspect, the disclosure features a prosthetic heart valve including one or more support structures, in which at least one support structure defines an elongate central passageway having a longitudinal axis and the at least one support structure is configured to biodynamically fix the prosthetic heart valve to native leaflets of a native heart valve of a heart. The prosthetic heart valve includes a plurality of leaflet elements attached to the at least one support structure and disposed within the elongate central passageway for control of blood flow through the elongate central passageway; and a cover configured to be disposed between a portion of the at least one support structure and an atrial side of at least one of the native leaflets. When the prosthetic heart valve is implanted in the native heart valve, the cover is configured to reduce leakage around the prosthetic heart valve.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 40 is a side view of a bracket of a prosthetic heart valve having two frame sleeves, in accordance with an embodiment.

FIG. 41 is a top, cross-sectional view of the bracket of FIG. 40 wherein the frame sleeves are located in an interior portion of the cylindrical portion of the prosthetic heart valve, in accordance with an embodiment.

FIG. 42 is a top, cross-sectional view of the bracket of FIG. 40 wherein the frame sleeves are located in an exterior portion of the cylindrical portion of the prosthetic heart valve, in accordance with an embodiment.

FIG. 57 illustrates several views of one arm of a ventricular set of arms configured to contact a native leaflet on a ventricular side of the leaflet and on an atrial side of the native leaflet, in accordance with an embodiment.

FIG. 58 is a side view illustrating one arm of a ventricular set of arms attached to a support structure and configured to contact a native leaflet on a ventricular side of the leaflet and on an atrial side of the native leaflet, in accordance with an embodiment.

FIGS. 59A-59B illustrate CAD drawings of several embodiments of a hook of an arm of an atrial set of arms, in accordance with an embodiment.

FIGS. 62A-62B depict several views of a cover for a ventricular set of arms, in accordance with two embodiments.

FIGS. 63A-63D depict several views of two arms of a ventricular set of arms, in accordance with different embodiments.

Figure 1:
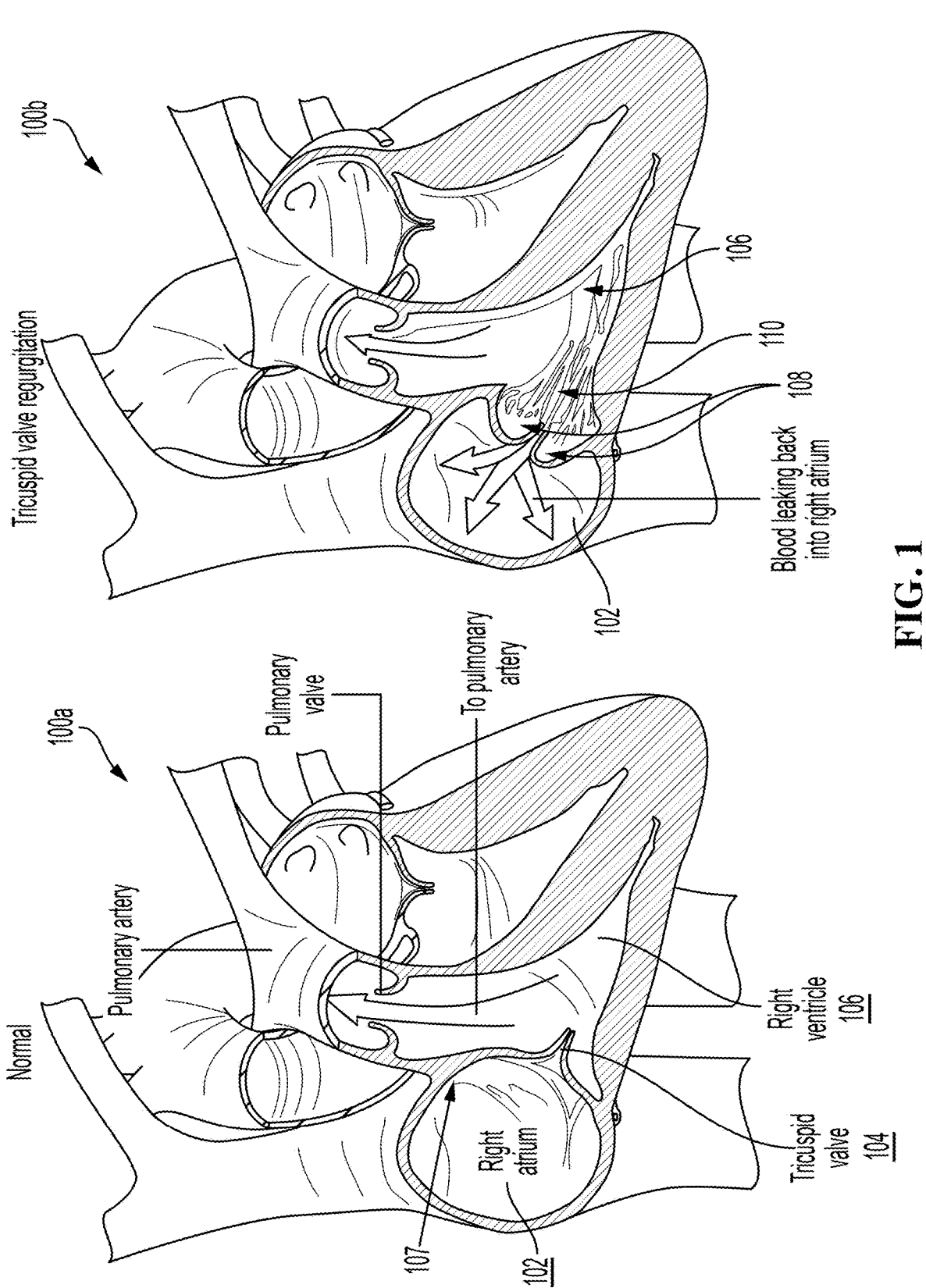
FIG. 1 is a cross-sectional view of the heart describing the anatomy of the right side of the heart during normal physiology and during the disease state of tricuspid regurgitation.

7 patent document or the patent disclosure, as it appears in the Patent and Trademark Office patent file or records, but otherwise reserves all (copyright or mask work) rights whatsoever.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Because aortic and mitral valve replacements have generally been the focus of device development, there exists a need for a solution for Tricuspid Regurgitation (TR), particularly because there is growing evidence showing that TR is associated with higher mortality rates and should not be left untreated even if the other heart valves have been addressed.

Like the mitral valve, the tricuspid valve is generally in an atrio-ventricular position. Consequently, it might be expected, in some cases, that a mitral valve replacement may be repurposed for use in the tricuspid position. However, specific aspects of the tricuspid valve anatomy and the surrounding anatomy (e.g., the tricuspid valve's larger size and proximity to conductive regions of the heart) make a dedicated solution more favorable than such a repurposing of mitral valve devices. Examples of a prosthetic tricuspid valve and methods for implanting the same may be found in International Application No. PCT/US2020/024765, titled "PROSTHETIC HEART VALVE" and filed on Mar. 25, 2020, which is incorporated herein by reference in its entirety for all purposes.

In addition, innovative aspects of a tricuspid-specific prosthetic valve may offer improvements to heart valves designed for other atrioventricular valves (i.e., mitral valve). The term "tricuspid valve" will therefore be used herein in reference to a prosthetic valve that is preferentially intended for the tricuspid position but may also be used for other atria-ventricular valves.

In accordance with aspects of the disclosure, a biodynamic prosthetic tricuspid valve is provided herein. As mentioned above, as referred to herein, the term "biodynamic" with regard to a prosthetic tricuspid valve, refers to a configuration of the prosthetic tricuspid valve that allows the prosthetic tricuspid valve to maintain axial stabilization within a native tricuspid valve of a heart, but to move within the native tricuspid valve responsive to alternating pressure differentials on either side of the native tricuspid valve during cardiac cycles of the heart, without directly attaching to (and/or without contacting) a native annulus and/or native chords of the native tricuspid valve, thereby preserving the natural motion of the native annulus. Specifically, the prosthetic tricuspid valve is axially stabilized within the native tricuspid valve by grasping the native leaflets of the native tricuspid valve, rather than relying on annular force or direct annular or chordal attachment. As referred to herein, the term "axial stabilization" with regard to a prosthetic tricuspid valve located within a native tricuspid valve refers to a portion of the prosthetic tricuspid valve being interposed between any two diametrically opposed points on a native annulus of the native tricuspid valve.

In some embodiments, the prosthetic tricuspid valve includes one or more support structures. For example, as discussed in further detail below, the prosthetic tricuspid valve may include, in some cases, one, two, three, or more than three support structures. At least one of the one or more support structures includes, in some embodiments, a cylindrical portion having an atrial end and a ventricular end. In some embodiments, the cylindrical portion of the one or more support structures defines an elongate central passageway of the prosthetic tricuspid valve. In some embodiments, a central axis (also referred to as the "longitudinal axis") of the elongate central passageway extends within the elongate central passageway from the atrial end of the cylindrical portion to the ventricular end of the cylindrical portion. When the prosthetic tricuspid valve is in an implanted configuration in a native tricuspid valve of a heart, blood generally flows through the elongate central passageway of the prosthetic tricuspid valve from an atrium of the heart to a ventricle of the heart, along the central axis of the elongate central passageway. Furthermore, in some additional embodiments, a plurality of leaflet elements attaches to the one or more support structures and are disposed within the elongate central passageway for control of blood flow through the elongate central passageway.

In some embodiments, ventricular arms extending from a first end of the cylindrical portion of the one or more support structures extend into the ventricle of the heart to contact the ventricular surface of the native leaflets, while atrial arms extending from a second end opposite the first end of the cylindrical portion of the one or more support structures extend into the atrium to contact the atrial surface of the native leaflets. Advantageously, in some embodiments, various features of the prosthetic tricuspid valve described herein configure the valve for transcatheter implantation, re-positioning, and/or removal. For example, the prosthetic tricuspid valve described herein may be easily positioned and deployed in a wide range of patients with the ability to control the deployment, assess complete functionality, and/ or maintain the ability to recapture and remove the implant prior to full release.

A "patient" or "subject" as used herein generally refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention described herein is directed toward use with humans. However, other subjects are also possible. In some embodiments, a subject may demonstrate health benefits, e.g., upon implantation of the valves described herein.

Although various examples are described herein in which prosthetic tricuspid valves are configured for replacement of the native tricuspid valve, it should be appreciated that appropriate modifications may be made for use of the prosthetic tricuspid valves disclosed herein to replace other native heart valves (e.g., other atrioventricular valves) and/ or in any other non-heart valves.

FIG. 1 displays a side cross-sectional view of two versions 100a, 100b of an exemplary native heart. The embodiment 100a depicts a normal anatomy of the native heart, in which blood flows from a right atrium 102 through a tricuspid valve 104 into a right ventricle 106, then through a pulmonary valve to the pulmonary artery. Separating the right atrium 102 from other parts of the heart (e.g., the left atrium) is the atrial septal wall 107. Embodiment 100b depicts a native heart with tricuspid regurgitation, in which blood leaks from the right ventricle 106 through the tricuspid valve 104 and into the right atrium 102. Also depicted in FIG. 1 are two leaflets 108 of the native tricuspid valve 104 which, in embodiment 100b, are shown having chordae 110 attached to the ventricular side of the leaflets and which serve to control the opening of the valve 104.

Figure 2:
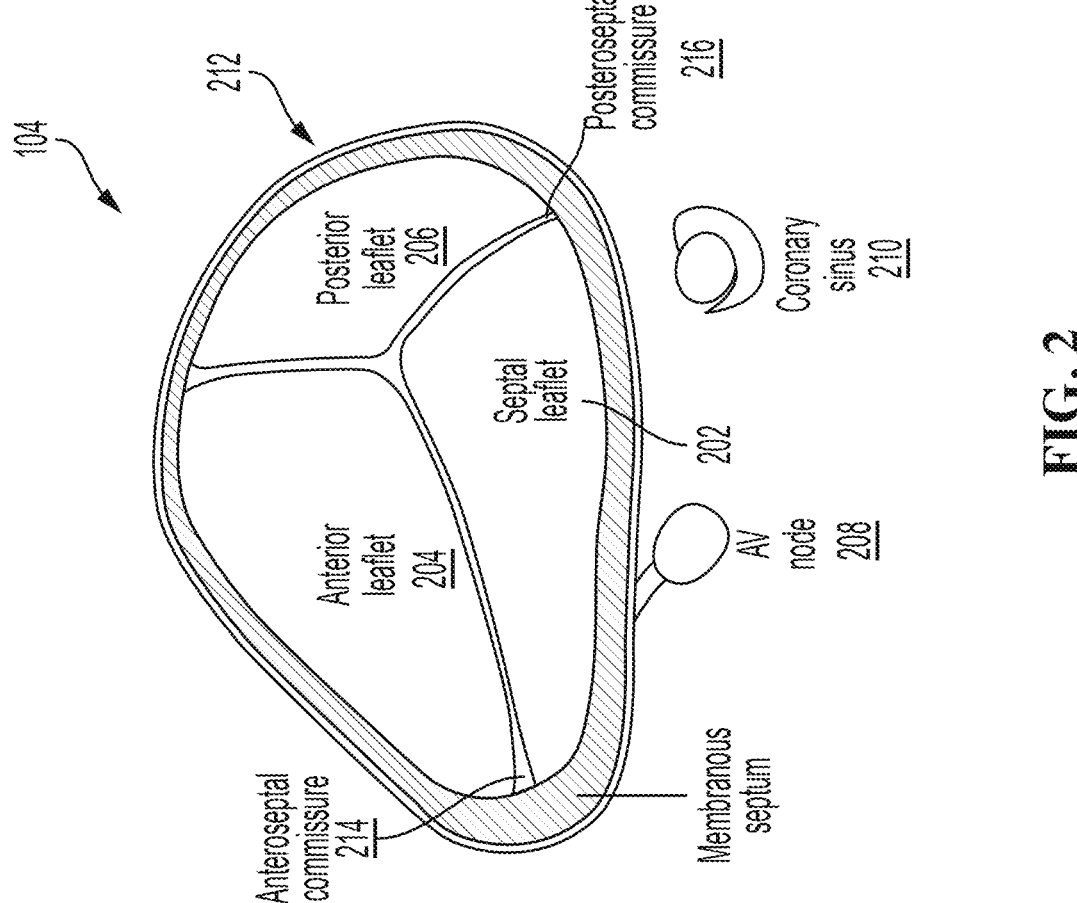
FIG. 2 is an en-face drawing of the tricuspid valve anatomy, depicting a non-uniform, or asymmetric shape.

FIG. 2 depicts a top view of an exemplary tricuspid valve 104, including typical anatomical positioning of the three native leaflets (septal 202, anterior 204, and posterior 206), as well as surrounding anatomical structures, such as the Atrioventricular Node (AV Node) 208 and Coronary Sinus 210. In some embodiments, tricuspid annulus 212 circumferentially surrounds the three native leaflets 202, 204, 206 and, in this example, the tricuspid annulus 212 has a non-circular or asymmetric shape. The area between the anterior leaflet 204 and septal leaflet is generally referred to as the anteroseptal commissure 214. The area between septal leaflet 202 and posterior leaflet 206 is generally referred to as posteroseptal commissure 216.

Support Structures

Figure 3:
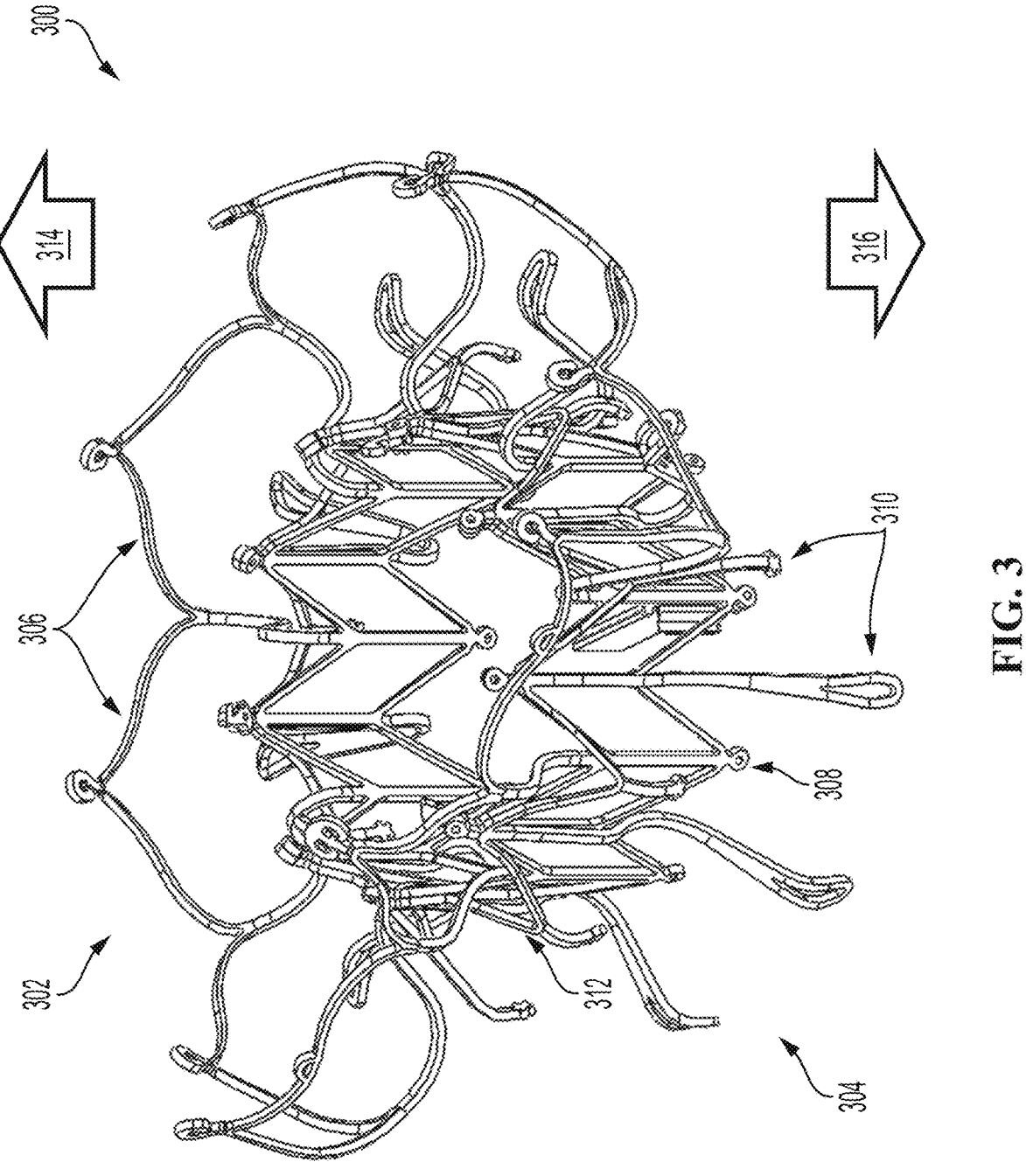
FIG. 3 is a CAD drawing of a perspective view of two support structures for a prosthetic heart valve, in accordance with an embodiment.
Figure 4A:
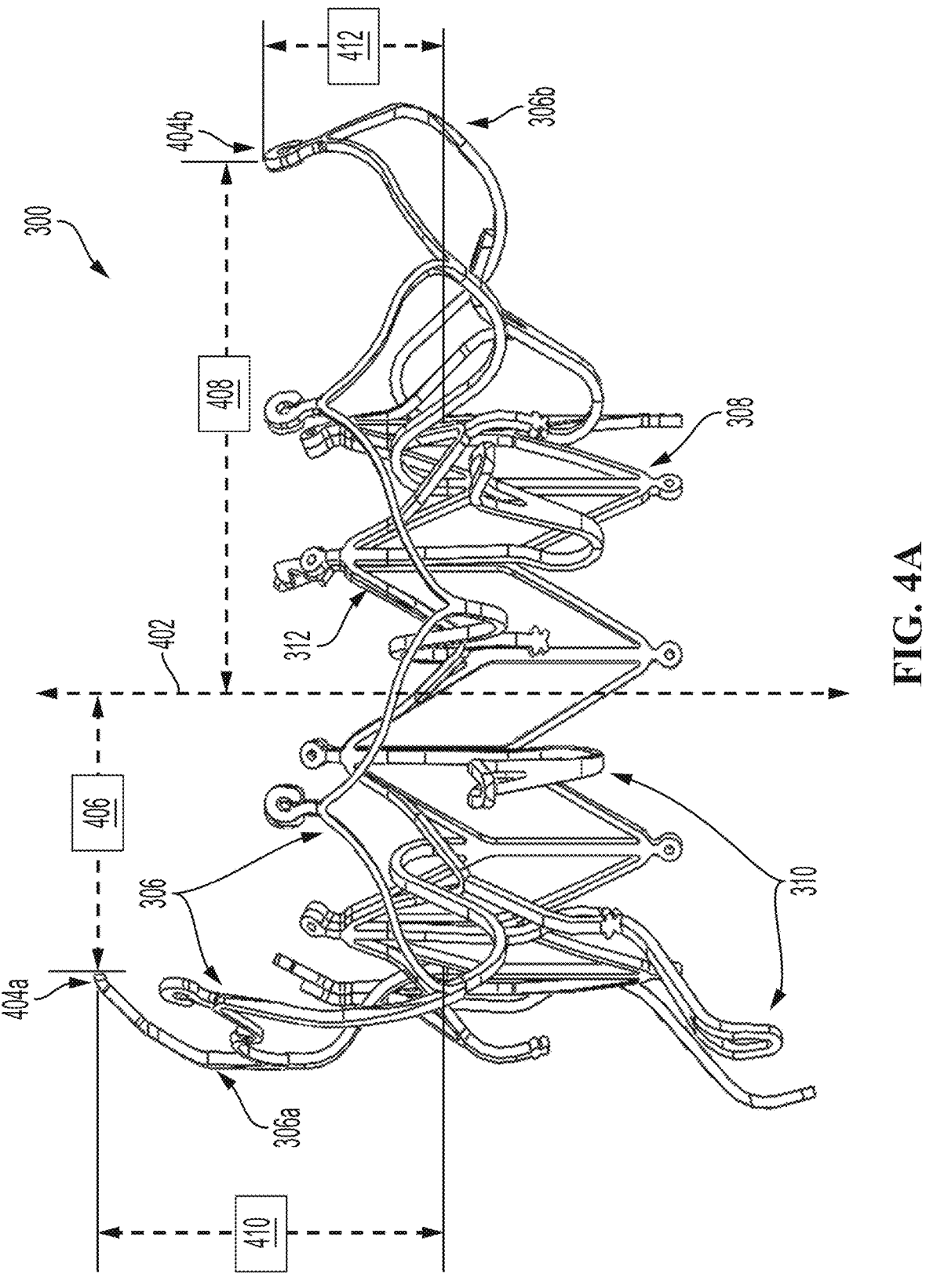
FIGS. 4A-4B are CAD drawings of a side view of two support structures for a prosthetic heart valve, in accordance with an embodiment.
Figure 4B:
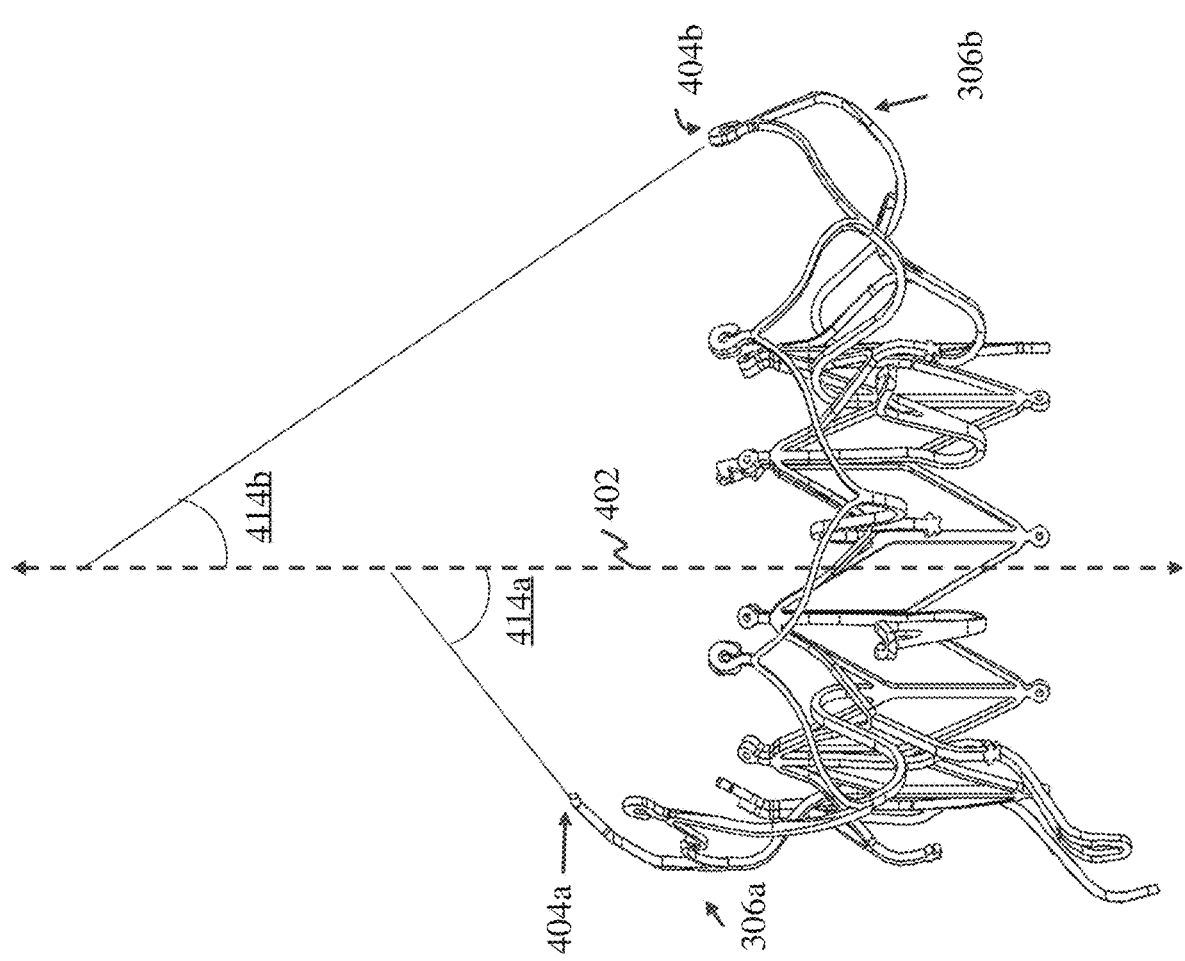
Figure 5:
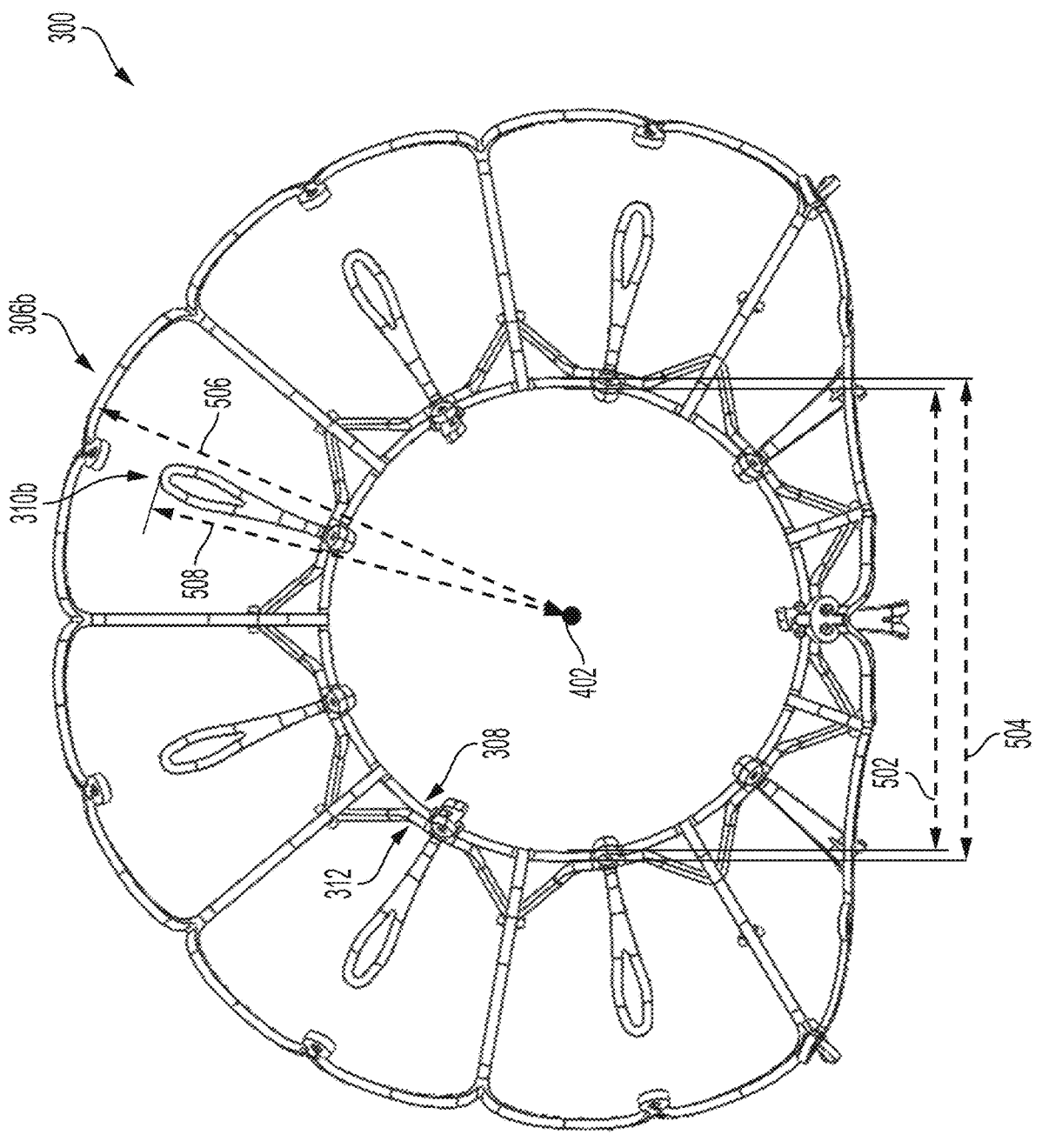
FIG. 5 is a CAD drawing of a top view of two support structures for a prosthetic heart valve, in accordance with an embodiment.

FIG. 3-FIG. 5 show several views of one or more example support structures 300 of an exemplary prosthetic heart valve, which is configured to fit within a native tricuspid annulus 212. However, in some embodiments, the prosthetic heart valve may have a generally symmetric shape. FIG. 3 illustrates a perspective view of the support structures 300. The exemplary support structures 300 may include an atrial support structure 302 and a ventricular support structure 304. The atrial support structure 302 may include, in some embodiments, an atrial set of arms 306 (also referred to as "atrial arms") and an atrial cylindrical portion 308. The ventricular support structure 304 may include, in some embodiments, a ventricular set of arms 310 (also referred to as "ventricular arms") and a ventricular cylindrical portion 312. In some such embodiments, the atrial set of arms 306 extend generally above the atrial cylindrical portion 308 (in the atrial direction 314) and the ventricular set of arms 310 extend generally below ventricular cylindrical portion 312 (in the ventricular direction 316). In some embodiments, the atrial support structure 302 interfaces with ventricular support structure 304 such that the atrial cylindrical portion 308 "sits" in the ventricular cylindrical portion 312. In some embodiments, the structures 302 and 304 interlock such that, once combined, structures 302 and 304 may operate as a single structure. In some embodiments, the atrial support structure 302 and ventricular support structure 304 may be shaped such that the atrial cylindrical portion 308 is aligned with the ventricular cylindrical portion 312. In some embodiments, one or more atrial arms 306, the atrial cylindrical portion 308, one or more ventricular arms 310, and/or the ventricular cylindrical portion 312 may be shaped such that the prosthetic heart valve has an asymmetric shape to avoid trauma to the surrounding anatomy (e.g., the septal wall 107). In some embodiments, the prosthetic heart valve is generally symmetric in shape.

FIG. 4A illustrates a side view of the exemplary support structures 300. As illustrated in this view, one or more members of the atrial cylindrical portion 308 aligns with one or more members of the ventricular cylindrical portion 312. In particular, the atrial cylindrical portion 308 and ventricular cylindrical portion 312 form a cylindrical space (also referred to as the "elongate central passageway") about central axis 402. In some embodiments, a distal portion 404 of one or more atrial arms 306 (e.g., atrial arm 306a) may be bent towards the central axis 402 of the elongate central passageway such that the distal end 404a of the arm 306a has a maximum distance 406 to the central axis 402 that is less than the distance 408 of the distal end 404b of other arms (e.g., atrial arm 306b) of the atrial set of arms to the central axis 402. As illustrated in FIG. 4B, in some embodiments, a distal portion 404 of one or more atrial arms 306 (e.g., atrial arm 306a) may be bent towards the central axis 402 such that the distal end 404a of the arm 306a has an angle 414a to the central axis 402 that is different from the angle 414b of the distal end 404b of other arms (e.g., atrial arm 306b) of the atrial set of arms to the central axis 402. For example, angle 414a may be greater than angle 414b.

As depicted in FIG. 4A, one or more arms of the atrial set of arms 306 depicted in FIG. 3-FIG. 5 may have, in some embodiments, an axial length that is either less than or greater than the axial length of the other arms of the atrial set of arms 306. An arm may, in some cases, have a first dimension parallel (also referred to as "axial length") to the central axis 402 and a second dimension perpendicular (also referred to as "radial length") to the central axis 402. For example, atrial arm 306a of FIG. 4A has a greater axial length 410 than the axial length 412 of atrial arm 306b. In some embodiments, it may be desirable for one or more first arms of the atrial set of arms to be shorter than one or more second arms of the atrial set of arms in a compressed configuration such that, when deployed in a bent configuration, the first atrial arm(s) (e.g., arm 306a) minimizes its coverage of the septal wall 107, which may impede future ability to perform trans-septal cardiac procedures. As illustrated in FIG. 4A, one or more atrial arms 306 are asymmetric with respect to at least one other atrial arm, thereby forming an asymmetric atrial support structure 302. In some embodiments, one or more atrial arms are symmetric with respect to at least one other atrial arm. In some embodiments, the atrial support structure is symmetric in shape.

In some embodiments, a ventricular aim (e.g 310a of arms 310 in FIG. 4B) is configured to originate from the atrial side. Ventricular arm 310b of FIG. 4B, in some embodiments, is configured to originate from the atrial side 314. In some embodiments, an atrial arm (e.g., arm 306b of arms 306 in FIG. 4A) is configured to originate from the ventricular side.

As illustrated in FIG. 5, in some embodiments, the diameter 502 of the atrial cylindrical portion 308 may be less than the diameter 504 of the ventricular cylindrical portion 312. In some embodiments, one or more atrial arms 306 have a greater radial length 506 than one or more ventricular arms 310. For example, atrial arm 306*b* has a greater radial length 506 than the radial length 508 of corresponding ventricular arm 310*b*.

Figure 6:
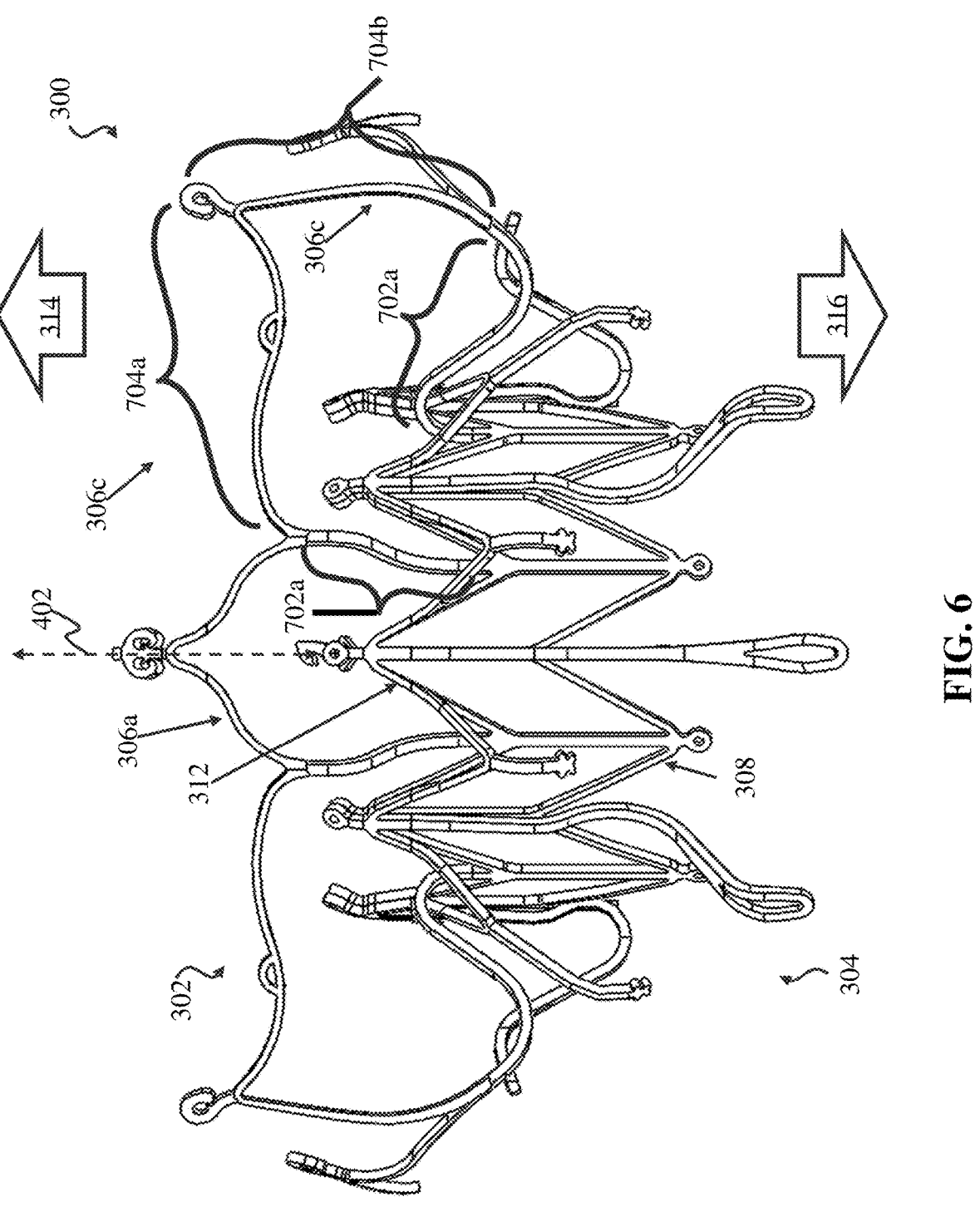
FIG. 6 is a CAD drawing of a front view of a cross-section of two support structures for a prosthetic heart valve, in accordance with an embodiment.

FIG. 6 illustrates a front view of a cross-section of the support structures 302 and 304. FIG. 6 also depicts an embodiment in which the proximal segment 702*a* of the one or more atrial arms (e.g., arm 306*c*) has a first proximal curvature towards the ventricular end 316 of the atrial cylindrical portion 308 and a second distal curvature in the direction 314 of the atrial portion of the cylindrical portion. In some such embodiments, the distal segments 704*a*, 704*b* (collectively referred to as 704) of the atrial arms serves to connect two adjacent proximal segments 702*a*, 702*b* (collectively referred to as 702) of the atrial arms (e.g., of arm 306*c*), where the distal segment 704 of the atrial arms curves towards the central axis 402 of the elongate central passageway to ensure the distal segment 704 is atraumatic to the surrounding anatomy.

Figure 7:
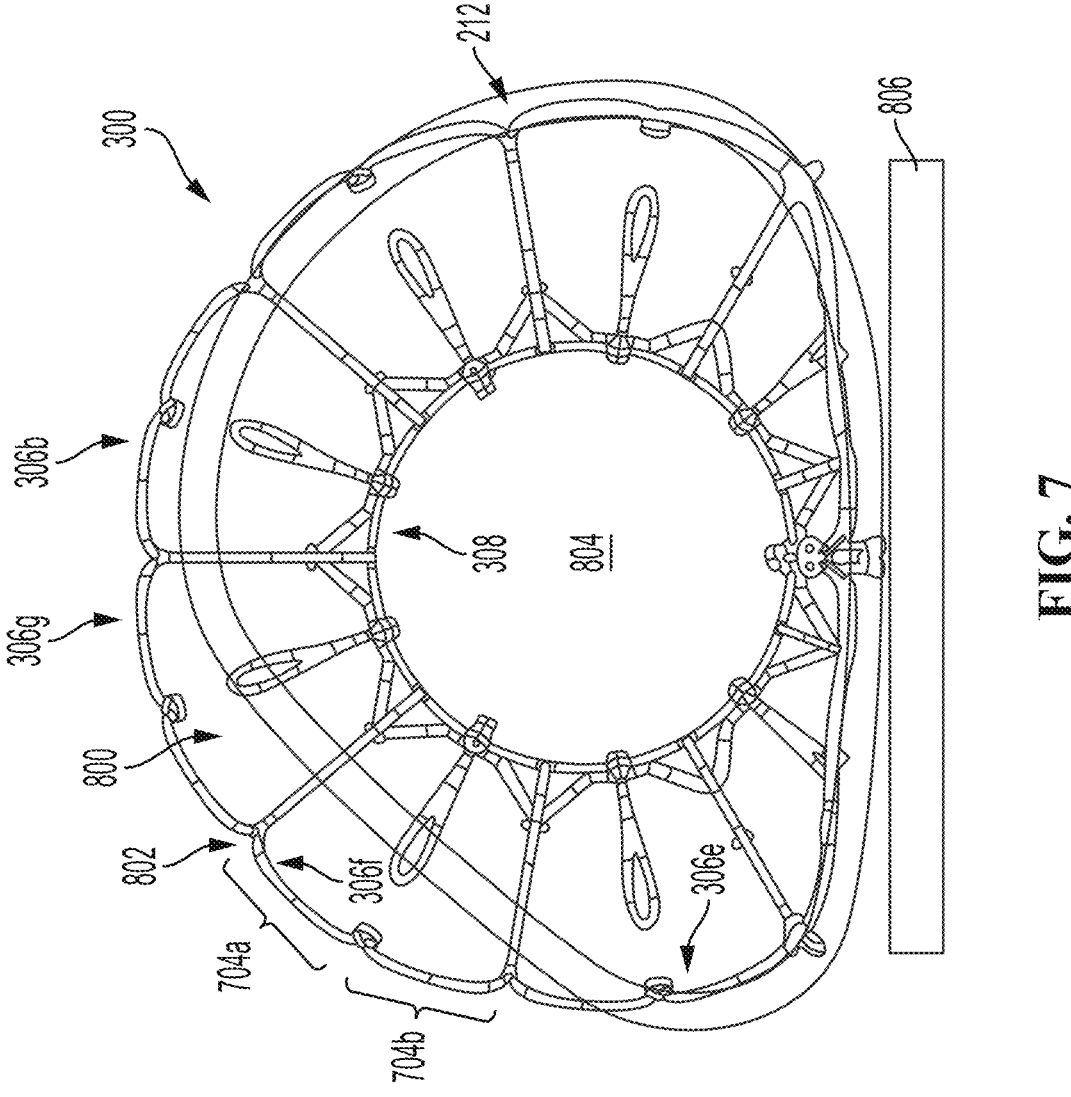
FIG. 7 shows a top view of a prosthetic heart valve in a native tricuspid valve annulus, in accordance with an embodiment.

FIG. 7 shows a top view of the example support structures 300 of prosthetic heart valve in a deployed configuration in a native tricuspid annulus 212 in which one or more atrial arms (e.g., arms 306*e*, 306*f*, 306*g*) form a circumferential region 800 that is configured to extend beyond the native tricuspid annulus 212. In this example embodiment, the distal segments 704*a*, 704*b* (collectively referred to as 704) of the atrial arms are joined to the proximal segments 702 of FIG. 6 of the atrial set of arms 306 at a location 802 that is beyond the interior edge of the native tricuspid annulus 212. In this way, the atrial set of arms 306 of the prosthetic heart valve may be configured to prevent regurgitant blood flow from the native ventricle 106 to the native atrium 102 around the exterior of the cylindrical portion (indicated as area 804 within the atrial cylindrical portion 308) of the prosthetic heart valve.

Figure 9:
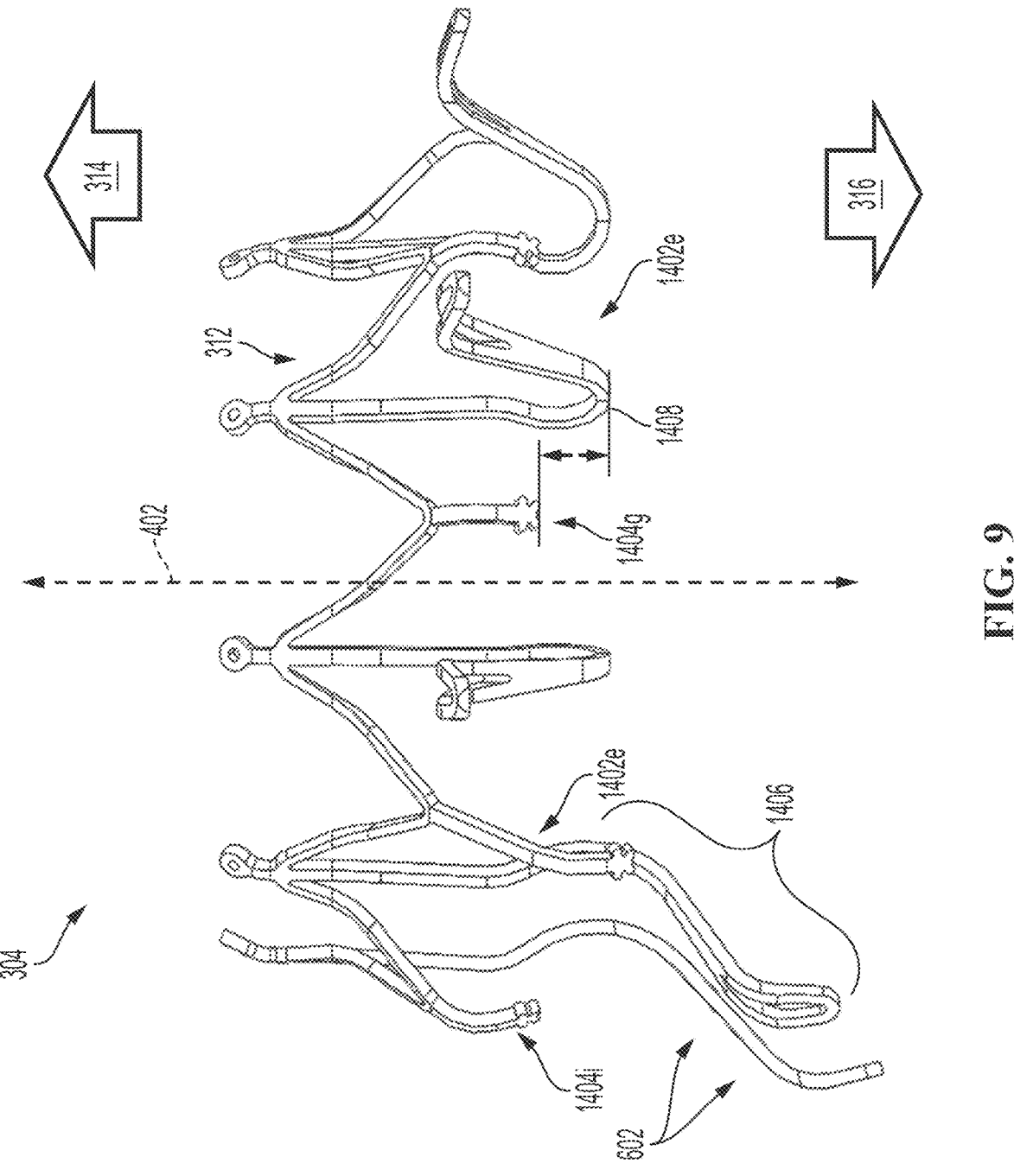
FIG. 9 is a CAD drawing of a side view of a support structure for a prosthetic heart valve, in accordance with an embodiment.

In some embodiments, the ventricular set of arms 310 may include three ventricular-directed arms (collectively referred to as 602, e.g., as shown in FIG. 9 below) configured to hold a native leaflet radially outward from a native tricuspid valve 104 in an open position. The ventricular-directed arms 602 of the ventricular set of arms and the arms of the atrial set of arms are configured to enable the outer edge of the cylindrical portion of the prosthetic heart valve to be located closer to a wall of the native heart, which may help to minimize paravalvular regurgitant flow if, for example, a native leaflet of the native tricuspid valve 104 is held radially outward from the native tricuspid valve in an open position. In the example of FIG. 7, the prosthetic heart valve is configured to be located closer to the septal wall 806 of the native heart. In another set of embodiments, the prosthetic heart valve is configured to be located closer to any other wall of the heart along the circumference of a native annulus 212. Similarly, in the example of FIG. 7, the prosthetic heart valve is configured to hold the septal leaflet radially outward from the native tricuspid valve 104 in an open position. In another set of embodiments, the prosthetic heart valve is configured hold the anterior and/or posterior leaflets radially outward from the native tricuspid valve in an open position.

In some embodiments, the ventricular set of arms 310 includes three ventricular-directed arms. In another set of embodiments, there may be one, two, or more than three ventricular-directed arms. Similarly, in the embodiments depicted in FIG. 3-FIG. 7, the atrial set of arms 306 includes three arms that are asymmetric relative to other arms of the atrial support structure 302. However, in some embodiments, the atrial set of arms includes arms that are generally symmetric relative to other arms of the atrial support structure. In another set of embodiments, there may be one, two, or more than three arms that are asymmetric relative to other arms of the atrial support structure 302. In yet another set of embodiments, there may be no arms that are asymmetric relative to other arms of the atrial support structure 302.

Figure 8A:
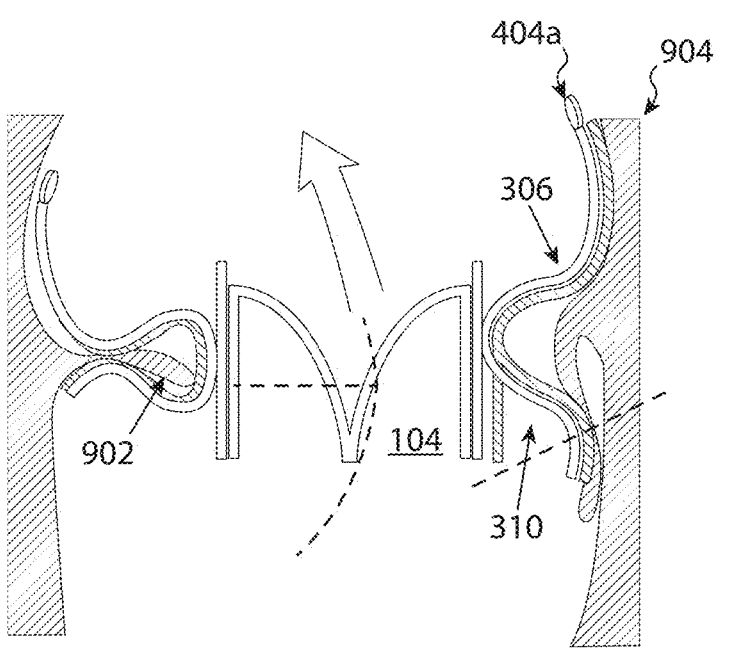
FIG. 8A shows a side view of a prosthetic heart valve in a native tricuspid valve annulus, in accordance with an embodiment.

FIG. 8A depicts cross-sectional side views of the support structures 300 of a prosthetic heart valve implanted in a native tricuspid valve 104 in which the ventricular-directed arms of the ventricular set of arms 310 are shown to hold a leaflet 902 radially outward from the native tricuspid valve 104 in an open position and the the atrial set of arms 306 rest along a wall of the native heart. Also shown in FIG. 8A is a distal portion 404*a* of an atrial arm 306*a* curving away from a wall 904 of the native heart so as to be atraumatic to the wall 904 of the native heart. The ventricular-directed arms of the ventricular set of arms 310 may, in some embodiments, also have a distal curvature toward a central axis 402 of the elongate central passageway to avoid trauma to the native leaflets, the wall of the native heart, and/or any other surrounding anatomy.

In some embodiments, the ventricular-directed arms of the ventricular set of arms 310 may be further configured to avoid obstruction of an Outflow Tract of a right ventricle 106 of the native heart.

Figure 8B:
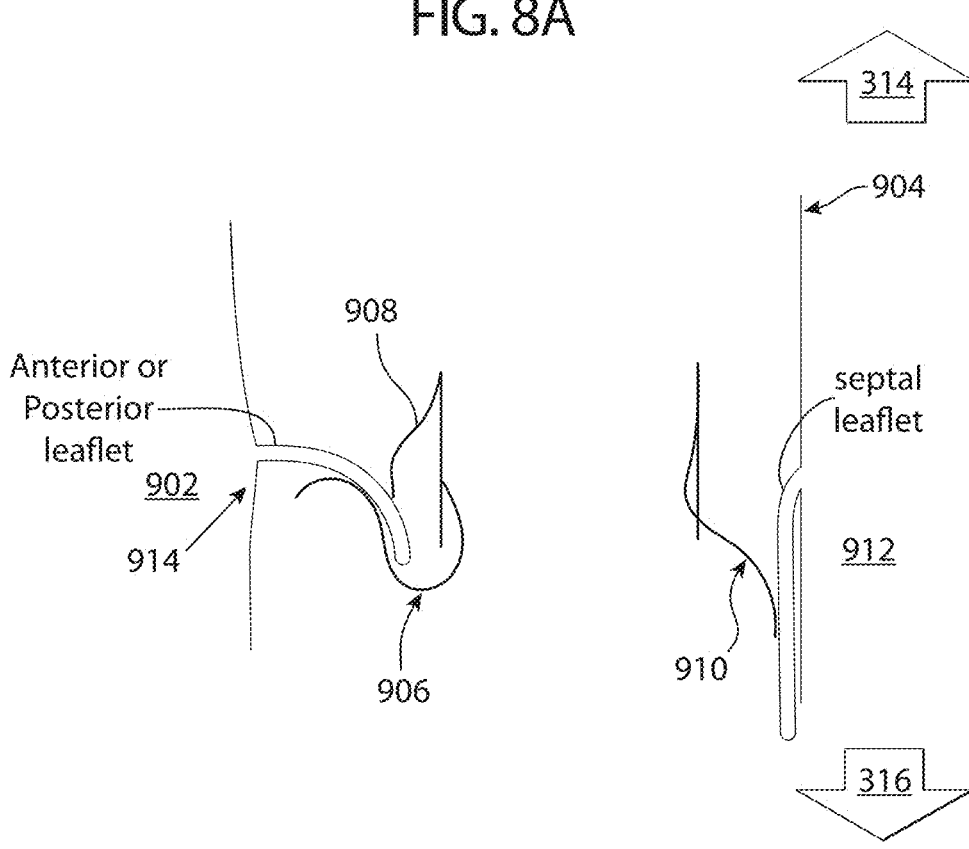
FIG. 8B is a drawing of a side view of possible points of contact by the atrial and/or ventricular arms with a native heart.

FIG. 8B also illustrates possible points of contact by ventricular arms 310 with a native heart. In particular, ventricular arm 906 (of arms 310) is configured to originate from the atrial side 314 of the anterior or posterior leaflet 902 and contact the ventricular side of the leaflet 902. Ventricular arm 906 may be shaped such that it exerts force (e.g., a pinching force with arm 908) against leaflet 902. Ventricular arm 906 may be shaped such that the arm 906 does not contact an annulus portion 914. Ventricular arm 908 is configured to originate from the atrial side 314 and contact the atrial side of leaflet 902. Ventricular arm 910 is configured to originate from the atrial side 314 and contact (e.g, exert force on) septal leaflet 912 against septal wall 904.

The arms of the atrial set of arms may extend from an atrial side of an atrial cylindrical portion of a support structure. The atrial set of arms of the support structure may have a flat pattern.

FIG. 9 depicts a view of an embodiment of a ventricular set of arms 310 of the ventricular support structure 304 in which three of the arms 602 have a ventricular-directed orientation 316 and are configured to contact a native leaflet on an atrial side of the native leaflet and six of the arms 1402 (including arm 1402*e*) have an atrial-directed orientation 314 and are configured to contact a native leaflet on a ventricular side of the native leaflet. The atrial-directed arms 1402 of the ventricular set of arms may be configured to avoid contact with a native annulus 212 of a native heart. The arms of the ventricular set of arms extend from an atrial side of a ventricular cylindrical portion 312 of a ventricular support structure 304. In another set of embodiments, the ventricular set of aims may include one, two, or more than three ventricular-directed arms 602. The ventricular support structure 304 may further include a third set of arms such as an annular-directed set of arms 1404, as further described below.

FIG. 9 also depicts an embodiment in which the ventricular-directed arms 602 (e.g., a third set of arms) of the ventricular set of arms 310 are configured to be atraumatic to the surrounding anatomy. Each ventricular-directed arm 602 of the ventricular set of arms 310 has a distal segment 1406 with a first proximal curvature towards the central axis 402 of the elongate central passageway, a second intermediate curvature away from the central axis 402 of the elongate central passageway, and a third distal curvature towards the central axis 402 of the elongate central passageway such that the distal-most portion of the one or more arms 602 of the ventricular set of arms is approximately parallel with the central axis 402 of the elongate central passageway to avoid trauma to the surrounding anatomy.

FIG. 9 also depicts a subset (1404g, and 1404i) of the multiple (in this example, nine) arms (collectively referred to as 1404, e.g., a third set of arms) of the ventricular set of arms, which are configured to contact the native leaflet on the atrial side of the native leaflet. In some embodiments, the arms have a maximum distance to the central axis of the elongate central passageway that is less than the maximum distance of any of the atrial-directed arms and/or the maximum distance of the ventricular-directed arms of the ventricular set of arms to central axis. In some embodiments, the maximum distance from one or more arms to the central axis of the elongate central passageway may be greater than the maximum distance of any of the atrial-directed arms and/or ventricular-directed arms of the ventricular set of arms to the central axis. The arms of the ventricular set of arms are shown to alternate with either the ventricular-directed arms of the ventricular set of arms or the atrial-directed arms of the ventricular set of arms. More specifically, the arms of the ventricular set of arms may extend away from the central axis of the elongate central passageway generally towards the ventricular end of the one or more support structures. Referring to FIG. 9, in the embodiment depicted, the arms 1402 of the ventricular set of arms has a first proximal bend that extends away from the central axis 402 of the elongate central passageway, for example, forming about a 45° angle, and a second distal bend that extends towards the central axis 402 of the elongate central passageway to prevent trauma to the surrounding anatomy. In some embodiments, the distal-most portion is pointed towards the central axis 402.

The arms may have different lengths, depending on the desired function of the arms. In some embodiments, one or more arms are configured to engage a commissure of the native heart valve to prevent transvalvular regurgitant flow through one or more openings at the commissures. Two of the arms may be longer than the other arms and may extend farther radially from the central axis of the elongate central passageway to better fill an opening at the commissure. In some embodiments, three of the arms may be configured to engage the commissure of the native heart valve. In another set of embodiments, the arms may all be the same length.

Figure 16:
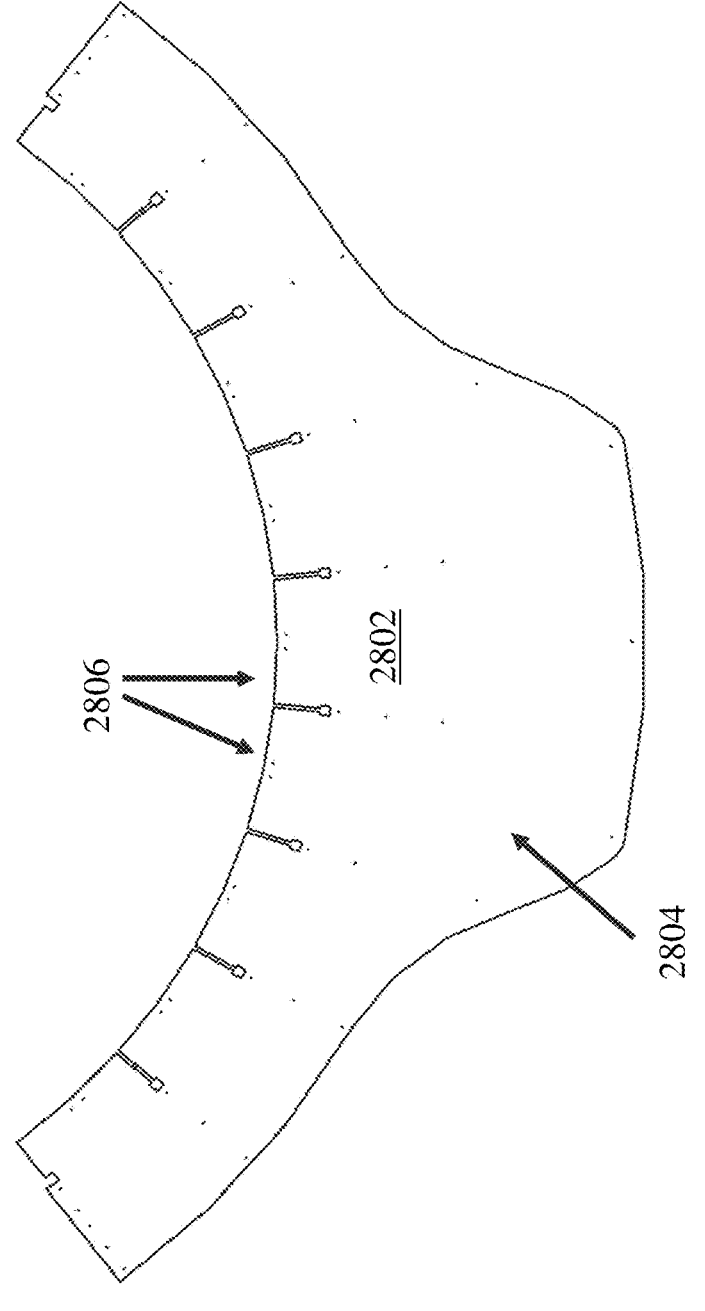
FIG. 16 is a CAD drawing of a top view of a cover for a ventricular set of arms, in accordance with an embodiment.

FIG. 9 shows that a distal end of the shorter arms of the ventricular set of arms does not, in some embodiments, extend in a ventricular direction 316 beyond the portion of the third set of arms that is perpendicular to the central axis of the elongate central passageway. In particular, the distal ends of the ventricular arms (e.g., arm 1404g) do not, in some embodiments, extend beyond the bend 1408 of the atrial-directed arms (e.g., arm 1402e). This configuration enables a cover (also referred to as a "skirt") (e.g., cover 2802, 3202, or 3302, described elsewhere) to be attached to the ventricular support structure 304 as illustrated in FIG. 16.

in some embodiments, the distal portion of the one or more arms 1404 may be configured to facilitate attachment of one or more covers (e.g., cover 2802, 3202, or 3302, described elsewhere herein) to the ventricular set of arms 310 with a suture or other type of thread, string, wire, cable, or line. In some embodiments, one or more arms of the ventricular set of arms 310 may have one or more fenestrations located anywhere along the one or more arms, which may be desirable to aid in attaching one or more covers to the ventricular set of arms. In some embodiments, one or more arms have a single fenestration located at the distal tip of each arm, and the ventricular-directed arms each have three fenestrations of different sizes located near the distal tip of each ventricular-directed arm. In some embodiments, the fenestrations may be of equal sizes. According to some embodiments, the distal tips of the arms each has four protruding elements, which may be useful in providing an anchoring structure around which a suture may be wrapped. Other embodiments may have fewer or greater protrusions.

In some embodiments, the support structure comprises a third set of arms attached to the support structure. In some embodiments, the third set of arms is a subset of the ventricular set of arms. In some embodiments, the third set of arms is a subset of the atrial set of arms. In some embodiments, the third set of arms is independent of the ventricular set and atrial set of arms. The third set of arms may extend, in some embodiments, from the atrial side of the support structure. In another set of embodiments, the third set of arms extend from the ventricular side of the frame. The third set of arms may be, in some cases, used to support a cover (e.g., a ventricular cover, an atrial cover) that aids in sealing of the prosthetic heart valve. In an exemplary set of embodiments, the third set of arms support a ventricular cover. Advantageously, the incorporation of a cover such as a ventricular cover may facilitate a larger washout area for the prosthetic heart valve as compared to prosthetic heart valves without the cover. Without wishing to be bound by theory, increasing of the washout area with the covers described herein may, in some cases, advantageously lead to a reduction in areas of stagnated blood flow and/or thrombosis formation proximate the prosthetic heart valve. By way of example for illustrative purposes only, in prosthetic heart valves in which the native leaflets are permitted to sit against the prosthetic heart valve, the washout area would be relatively small as compared to the embodiments described herein.

In some embodiments, the third set of arms and/or cover may advantageously hold the native leaflets and/or native chordae away from the central cylindrical portion of the prosthetic heart valve. In some embodiments, such a configuration may advantageously maximize the outflow diameter of the prosthetic heart valve (e.g., serving as the outermost valve cylinder) and/or prevent native leaflets and/or chordae from contacting the support structure e.g., thereby minimizing damage of the native leaflets and/or chordae. In some embodiments, the cover may advantageously have cuts and/or openings which facilitate a greater amount of washout area (as compared to other configurations). For example, in some embodiments, the third set of arms may include a ventricular cover, thereby providing greater washout area and/or an improved sealing surface on the ventricular cover.

In some embodiments, the atrial and ventricular sets of arms are bent such that in an implanted configuration in which the at least one support structure biodynamically fixes the prosthetic heart valve to the native leaflets of the native heart valve, in the event of motion of the cylindrical portion of the at least one support structure toward the atrial side of the native heart valve due to a ventricular systolic pressure load, one or more arms of the ventricular set of arms resist the motion while one or more arms of the atrial set of arms relax to maintain contact with the atrial side of the native leaflets. Similarly, in the event of motion of the cylindrical portion of the at least one support structure toward the ventricular side of the native heart valve due to a ventricular diastole pressure load and/or an elimination of a previously applied ventricular systolic load, one or more arms of the atrial set of arms resist the motion while one or more arms of the ventricular set of arms relax to maintain contact with the ventricular side of the native leaflets. This also creates, in some embodiments, a trampoline effect where the native leaflets act as spring-like elements to least partially absorb the applied pressure load and/or elimination of a previously applied pressure load.

For example, securing the prosthetic tricuspid valve to either side (e.g., the atrial surface or the ventricular surface) of the native leaflets may, in some cases, create a trampoline effect where ventricular systolic pressure load may be partially absorbed by the upward (atrial) motion and tensioning of the native leaflets. For example, in the event of motion of the cylindrical portion of the support structure toward the atrial side of the native tricuspid valve (e.g., due to a ventricular systolic pressure load), the ventricular arms resist the motion while the atrial arms relax to maintain contact with the atrial side of the native leaflets. Additionally, in the event of motion of the cylindrical portion of the support structure toward the ventricular side of the native tricuspid valve, the atrial arms resist the motion while the ventricular arms relax to maintain contact with the ventricular side of the native leaflets. Furthermore, as a result of the trampoline effect, force from the distal segment of each ventricular arm against the ventricular side of the native leaflets may be further distributed throughout an atrial and/or ventricular sealing skirt (i.e., cover) to minimize the risk of erosion through the native leaflets. In this way, for example, the prosthetic tricuspid valve may be, in some cases, biodynamically fixed within the native tricuspid valve during the cardiac cycle.

In some embodiments, the third set of arms and/or cover may push against the native leaflets of the native heart thereby improving the seal and/or minimizing damage to the native leaflets of the native heart. Advantageously, the third set of arms and/or cover may serve to distribute the forces across the prosthetic heart valve, thereby improving and/or enhancing the above-described trampoline effect. The third set of arms may also serve to increase the total surface area for sealing against the native leaflets, thereby reducing the likelihood of paravalvular leak.

Figures 10A, 10B, 10C:
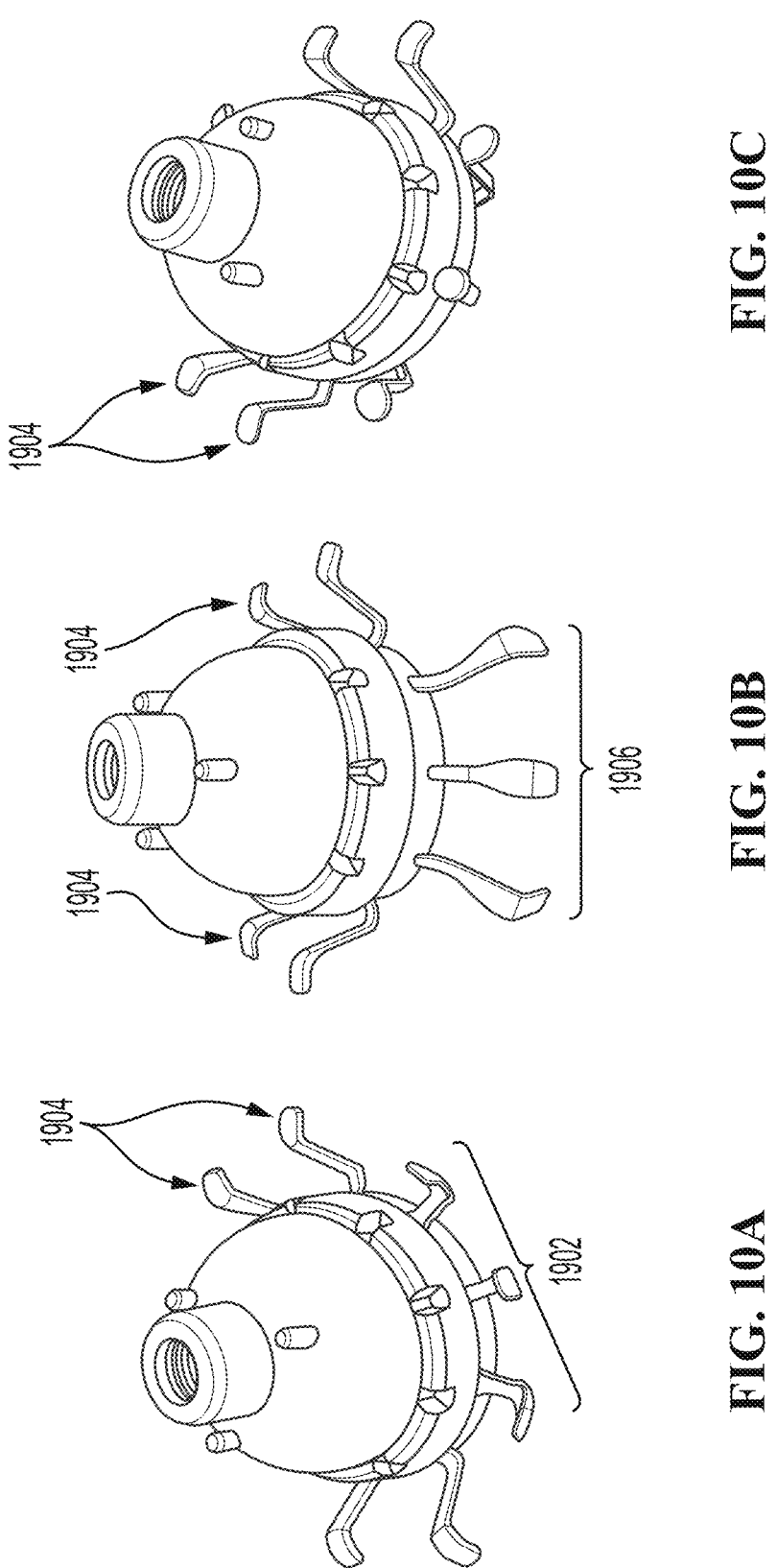
FIGS. 10A-10C illustrate several variations of a ventricular set of arms, in accordance with several embodiments.

FIGS. 10A-10C depict several embodiments for a ventricular set of aims 310 in which the arms have different orientations, lengths, and shapes. In FIG. 10A, three of the arms 1902 (also referred to as "gutter" arms) of the ventricular set of arms have a distal portion that extends in an atrial direction to contact the native leaflets on a ventricular side of the native heart valve and six of the arms 1904 (also referred to as "up" arms) have an atrial-direction orientation with an atraumatic distal bend. FIG. 10B depicts a ventricular set of arms in which three of the arms 1906 (also referred to as "down" arms) have a ventricular-directed orientation and six of the arms 1904 ("up" arms) have an atrial-direction orientation with an atraumatic distal bend. FIG. 10C depicts a ventricular set of arms in which all of the arms 1904 (e.g., the nine "up" arms) have the same atrial-direction orientation with an atraumatic distal bend.

Atrial Cover Embodiments

Figure 11:
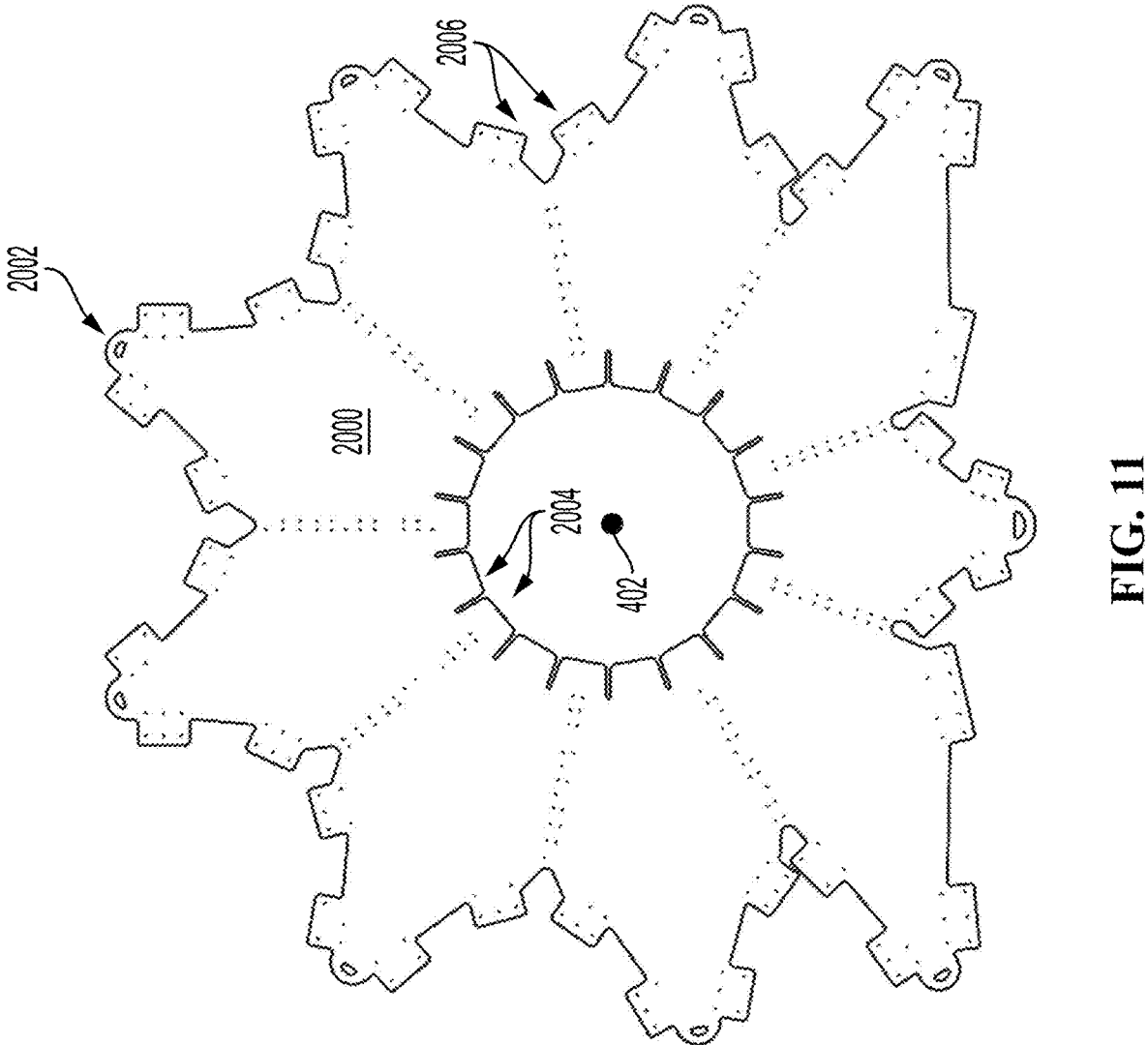
FIG. 11 illustrates a CAD drawing of a top view of a cover for an atrial set of arms, in accordance with an embodiment.

FIG. 11 is a top view of an atrial cover 2000 for an atrial set of arms, which includes a central donut-shaped region and nine radially-extending members, according to one set of embodiments. In some embodiments, the atrial cover is configured to be attached to the atrial set of arms 306. In its attached configuration, the central donut-shaped region is configured to contact an atrial side of the atrial set of arms, while the radially-extending members are configured to contact a ventricular side of the atrial set of arms. In the embodiment shown in FIG. 11, the atrial cover also has tabs extending perpendicularly from the edges of each radially-extending member and which are configured to wrap around a segment of the atrial set of arms and attach to a side of the atrial cover in order to facilitate attachment of the atrial cover to the atrial set of arms. In some embodiments, the tabs are attached to the atrial cover by means of a suture (or thread, string, wire, etc.). In some embodiments, the tabs, when attached to the atrial cover, are configured to slide along at least a portion of the distal segment of an arm of the atrial set of arms, which may be advantageous to enable the atrial cover to completely enclose the region between adjacent distal segments of the arms of the atrial set of arms when the atrial set of arms is in both an expanded and a compressed configuration. The atrial cover may have one or more fenestrations through which a suture (or thread, string, wire, etc.) may be passed to attach the tab of the atrial cover to the radially-extending member, thereby attaching the atrial cover to the atrial set of arms. In some embodiments, the atrial cover of FIG. 11 may be divided into thirds to create three similarly shaped or identically shaped covers that may be separately attached to the atrial set of arms. Using more than one atrial cover may be advantageous, for example, to facilitate assembly of the prosthetic heart valve. In some embodiments, two or more than three atrial covers may be used.

In the embodiment shown in FIG. 11, the donut-shaped portion of the atrial cover has fenestrations that are radially aligned with the proximal portion of the arms of the atrial set of arms and which may be used to attach the atrial cover to the atrial set of arms, for example using suture, thread, string, wire, etc. In some embodiments, one or more of the spices of the radially-extending members may have one or more fenestrations. As shown in FIG. 11, each apex of the radially-extending members has a single fenestration 2002 which may be used to attach the atrial cover to the atrial set of arms (see e.g., arms 306 in FIG. 12) by passing a hook of the distal portion of the arms of the atrial set of arms through the fenestrations 2002, either temporarily to facilitate attachment, or permanently to further enhance attachment of the atrial cover 2000 to the atrial set of arms.

Also shown in FIG. 11 are tabs 2004 lining the inner edge of the donut-shaped portion of the atrial cover, which may be used to allow the atrial cover to follow an atrial-directed curvature of the atrial set of arms without over-stretching the inner edge of the atrial cover. As shown, the atrial cover has 18 inner tabs 2004; however, In another set of embodiments, the atrial cover may have as few as two inner tabs, more than 18 inner tabs, or any other number of inner tabs, for example nine (9), six (6), or three (3) inner tabs.

In some embodiments, the radially-extending members of the atrial cover may be configured to contact the atrial side of the atrial set of arms, in which case the tabs 2006 of the radially-extending members may be configured to wrap around a segment of the atrial set of arms to contact a ventricular side of the atrial cover in order to facilitate attachment of the atrial cover to the atrial set of arms.

In FIG. 11, the atrial cover 2000 is depicted as being produced from a flat, two-dimensional pattern. In another set of embodiments, the atrial cover may be produced as a three-dimensional structure, for example, by knitting, weaving, molding, forming, casting, or printing. In some embodiments, an atrial cover with a three-dimensional structure has a deployed configuration whose central diameter extends in a ventricular direction to create an elongate central passageway and which may be configured to cover the inner surface of a cylindrical portion of a support structure of a prosthetic heart valve.

Figure 12:
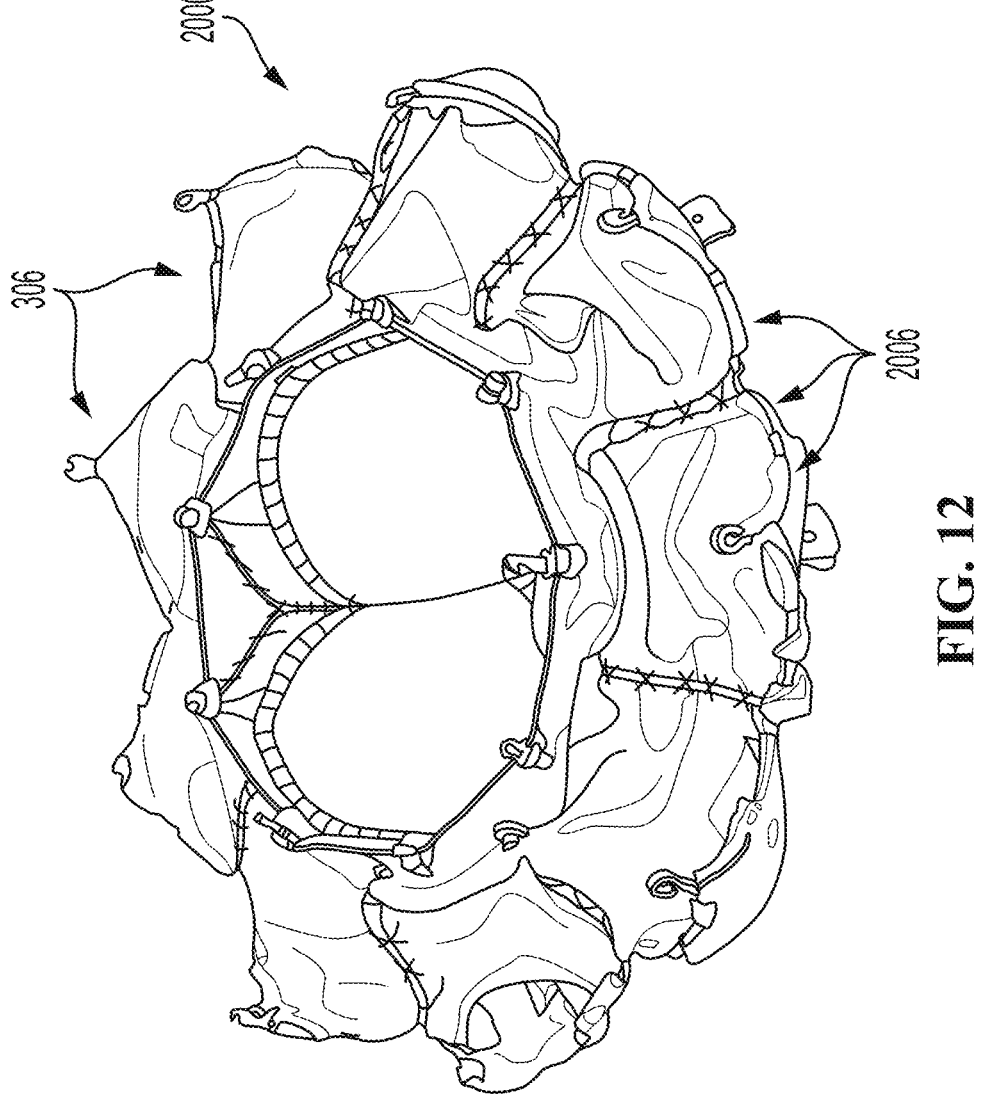
FIG. 12 presents a perspective photograph of an exemplary atrial cover attached to an exemplary atrial set of arms, in accordance with an embodiment.

FIG. 12 shows a photograph of an exemplary atrial cover (e.g., atrial cover 2000 of FIG. 11) attached to an atrial set of arms 306, according to an exemplary embodiment. In some embodiments, the tabs 2006 of the radially-extending members of atrial cover 2000 are wrapped around segments of the atrial set of arms 306 to contact a ventricular side of atrial cover 2000 in order to facilitate attachment of atrial cover 2000 to the atrial set of arms 306.

Figure 13:
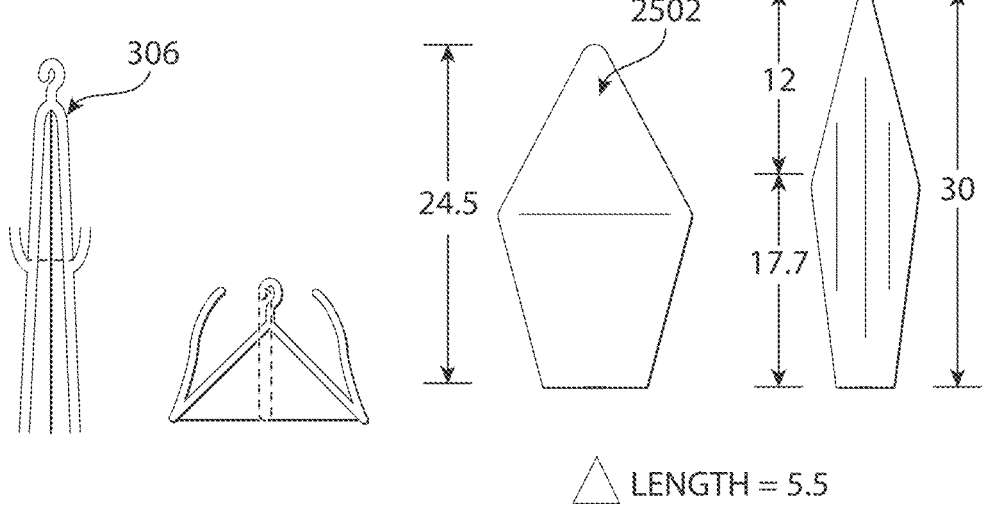
FIG. 13 illustrates a change in length of an arm of an atrial set of arms between a compressed and an expanded configuration, in accordance with an embodiment.

In some embodiments, one or more of the radially-extending members of the atrial cover may have one or more pleats configured to allow the atrial cover to increase or decrease the length of the one or more radially-extending members. In some embodiments, the radially-extending members of the cover may have a single pleat, comprising a peak in an atrial direction and a valley in a ventricular direction. The pleats of the atrial cover may, in some embodiments, allow the atrial cover to lengthen when attached to the atrial set of arms in which each arm of the atrial set of arms lengthens, as shown in FIG. 13. In some embodiments, the radially-extending members 2502 of a cover for the atrial set of arms 306 may have more than one pleat, or less than one pleat, for example, half of a pleat (one peak or one valley), two full pleats, (two peaks and two valleys), two and a half pleats (two peaks and three valleys or three peaks and two valleys), etc. Note that, once folded over the atrial arms, the tabs on the radially-extending members are configured to form a sleeve, in some embodiments. The sleeves and pleats may work together to conform to an atrial arm as the arm expands and contracts.

Figure 14:
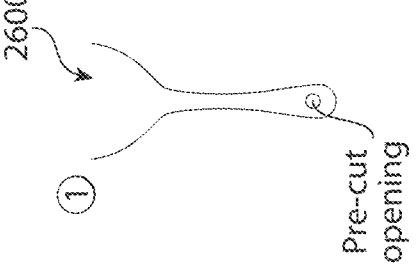
FIG. 14 illustrates several variations of one or more members that extend from a cover for an atrial set of arms, in accordance with an embodiment.

In some embodiments, one or more radially-extending members may be configured to attach to a delivery system for a prosthetic heart valve to help in deployment, positioning, repositioning, and/or recapture of the prosthetic heart valve. FIG. 14 shows several embodiments of an atrial cover whose one or more radially-extending members extend farther radially. In one set of embodiments, the one or more radially-extending members 2600 may have one or more fenestrations at located distally to facilitate attachment to the delivery system. In another set of embodiments, the radially-extending members 2602 may have two or more farther-extending members. In one such embodiment, radially-extending members may have three farther-extending members that may be braided to form a single farther-extending member 2604. In another embodiment, the one farther-extending member 2606 may be looped through a feature of the delivery system and attached to itself, for example using suture, thread, string, wire, adhesive, cable, or other means of attachment.

Figure 15:
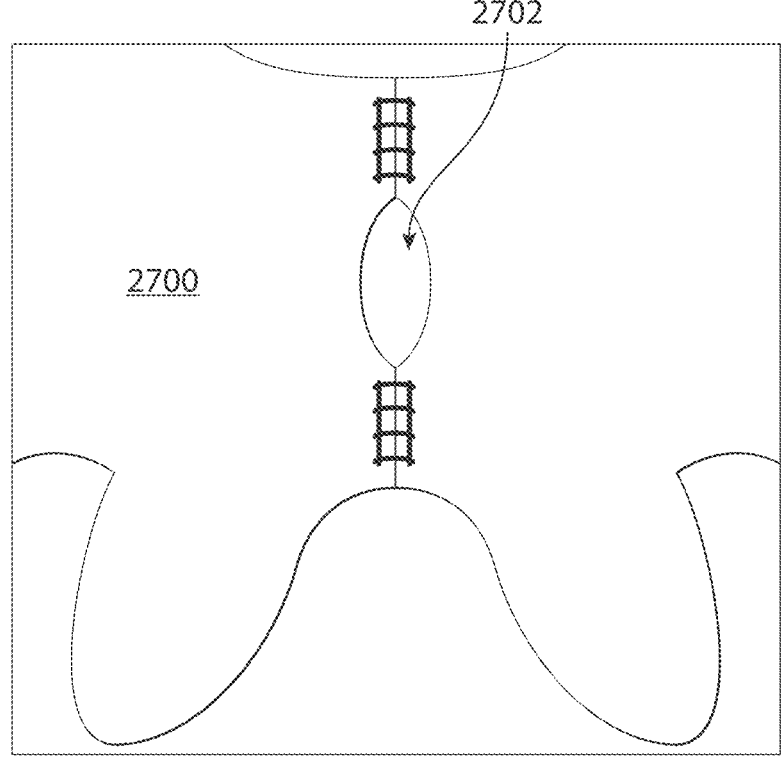
FIG. 15 illustrates a fenestration of a cover for an atrial set of arms, in accordance with an embodiment.

In some embodiments, the atrial cover 2700 may further include one or more fenestrations 2702 in the donut-shaped region of the atrial cover. In the embodiment depicted in FIG. 15, the fenestration is formed by connecting two edges of the donut-shaped region in such a way to create an opening between the connected regions of the edges.

Ventricular Cover Embodiments

FIG. 16 is a top view of a ventricular cover 2802 for a ventricular set of arms 310, which includes a central ventricular-directed flap portion 2804 and nine atrial-directed tabs 2806, according to one set of embodiments. In some embodiments, the ventricular cover 2802 is configured to contact an outer surface of the ventricular set of arms 310. The ventricular cover 2802 shown in FIG. 16 has a first side and a second side, such that the first and second sides are configured to be placed adjacent one another to create a continuous circumference and which may be placed on the outer surface of the ventricular set of arms 310. In some embodiments, the ventricular cover 2802 may be configured to contact an internal surface of the ventricular set of arms 310. The ventricular cover 2802 may have one or more fenestrations through which a suture (or thread, string, wire, etc.) may be passed to attach the ventricular cover 2802 to the ventricular set of arms 310.

The ventricular-directed flap portion 2804 of the ventricular cover 2802 is configured to contact an outer surface of the one or more ventricular-directed arms 602 of the ventricular set of arms. In the embodiment shown in FIG. 16, the central ventricular-directed flap portion of the ventricular cover 2802 is configured to cover three ventricular-directed arms 602 of the ventricular set of arms. In some embodiments, the ventricular cover 2802 may be configured to cover one, two, or more than three ventricular-directed arms 602 of the ventricular set of arms. In some embodiments, the flap portion 2804 is not centrally located but may be located closer to the first side of the ventricular set of arms, or closer to the second side of the ventricular set of arms.

Figure 17:
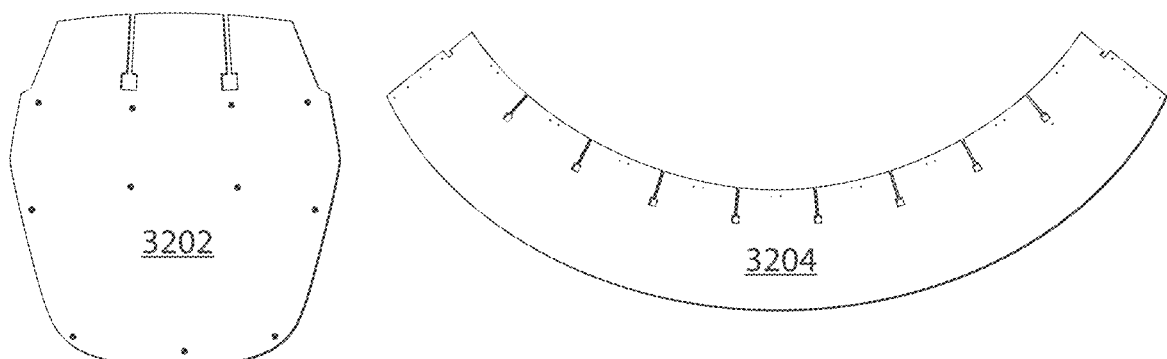
FIG. 17 is a top view of a ventricular cover for a ventricular set of arms that includes two covers, in accordance with an embodiment.

In some embodiments, the ventricular cover 2802 may include two or more covers. For example, in the embodiment shown in FIG. 17, the ventricular cover may include a first cover 3202 that includes a ventricular-directed flap, and a second cover 3204 that includes one or more atrial-directed tabs extending from a single strip-like member. In some such embodiments, the first cover 3202 may be placed on an outer surface of the second cover 3204, and the second cover 3204 may be placed on an outer surface of the ventricular set of arms 310. In another embodiment, the first cover 3202 may be placed on an outer surface of the ventricular set of arms 310, and the second cover 3204 may be placed on an outer surface of the first cover 3202. In another set of embodiments, the first cover 3202 and/or the second cover 3204 may be placed on an inner surface of the ventricular set of arms 310, and the two covers 3202, 3204 and the ventricular set of arms 310 may be arranged to construct any combination of the aforementioned configurations.

Figure 18:
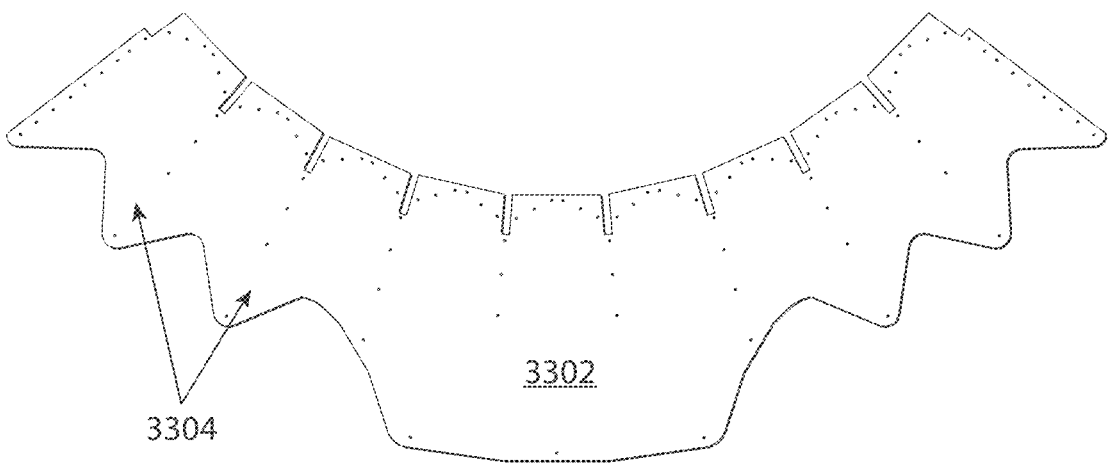
FIG. 18 is a CAD drawing of a top view of a cover for a ventricular set of arms, in accordance with another embodiment.

The ventricular cover 3302 may further include ventricular-directed tabs 3304, as shown in FIG. 18. The ventricular-directed tabs 3304 of FIG. 18 may be configured to attach to a cylindrical portion of one or more support structures of a prosthetic heart valve, which may be advantageous to provide additional structural support to the ventricular set of arms or to stabilize the one or more ventricular covers.

In some embodiments, the atrial-directed tabs of the ventricular cover each have an apex, which may be desirable to minimize the amount of cover material used in the construction of the prosthetic heart valve, to help reduce overall profile size in a compressed configuration.

In some illustrative embodiments, the ventricular cover is depicted as being produced from a flat, two-dimensional pattern; however, in another set of embodiments, the ventricular cover may be produced as a three-dimensional structure, for example, by knitting, weaving, molding, forming, casting, printing, etc. For example, the three-dimensional structure may include, at least in part, plastic, metal, fabric, etc. In some embodiments, a ventricular cover may have a three-dimensional structure in a deployed configuration whose central portion extends in a ventricular direction to create an elongate central passageway and which may be configured to cover the inner surface of a cylindrical portion of a support structure of a prosthetic heart valve.

Figure 19:
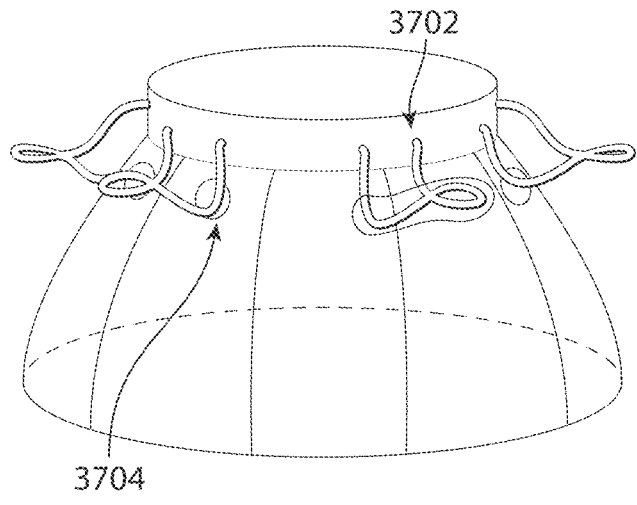
FIG. 19 is a perspective view of a cover for a ventricular set of arms in a deployed configuration, in accordance with an embodiment.
Figure 20A:
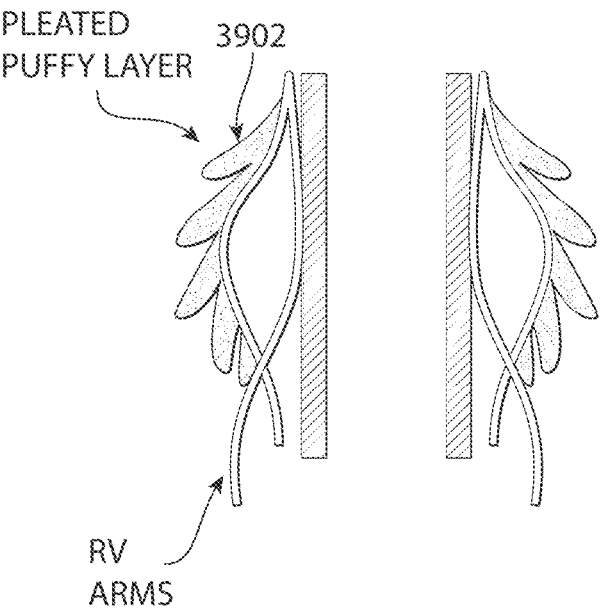
FIGS. 20A-20D illustrate a deployment sequence of a prosthetic heart valve having a cover for a ventricular set of arms with pleats, in accordance with an embodiment.
Figure 20B:
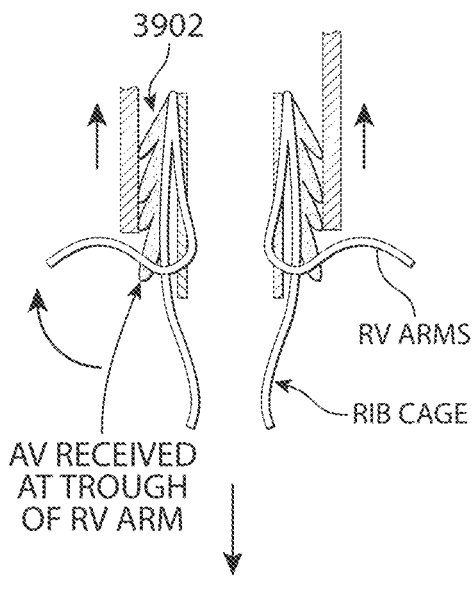
Figure 20C:
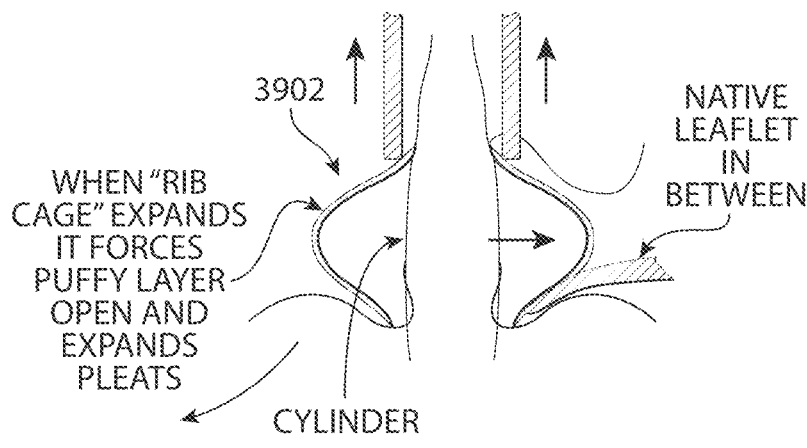
Figure 20D:
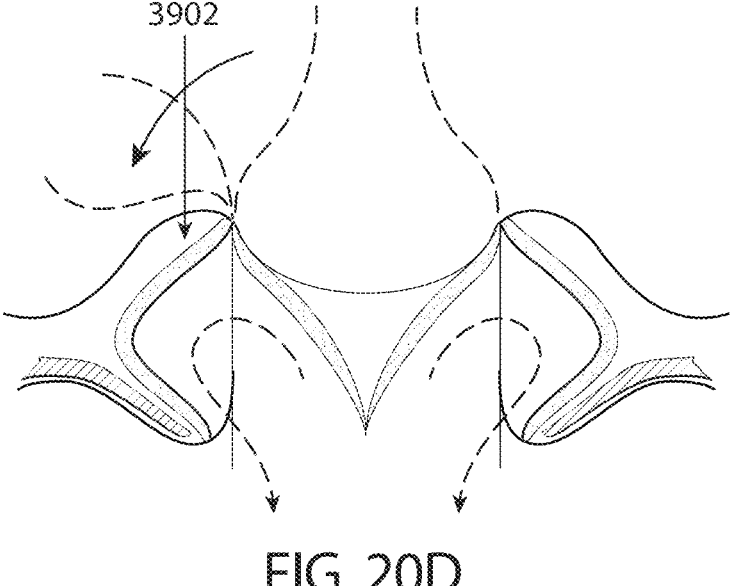

FIG. 19 depicts an embodiment of a ventricular cover 3702 in which a ventricular end of the ventricular cover extends farther in a ventricular direction beyond the ventricular-most portion of one or more arms of the ventricular set of arms. The ventricular cover 3702 of FIG. 19 further depicts multiple fenestrations 3704 configured to enable one or more arms of the ventricular set of arms to pass through the fenestrations in such a way that prevents leakage of blood through the fenestrations.

Cover Deployment

In some embodiments, one or more atrial covers are combined with one or more ventricular covers in a deployed configuration. For example, in some embodiments, the atrial cover 2000 of FIG. 11 is combined with the ventricular cover 2802 of FIG. 16. As another example, in some embodiments, the atrial cover 2000 of FIG. 11 is combined with one of the two ventricular covers 3202, 3204 depicted in FIG. 17. The atrial covers and ventricular covers of the prosthetic heart valve may include any combination of the aforementioned embodiments, as well as other embodiments not disclosed herein.

In some embodiments, the ventricular cover may further include one or more pleats configured to expand in a radial dimension when the ventricular cover is moved from a compressed to a deployed configuration. The one or more pleats may be configured to organize the ventricular cover in a compressed configuration to minimize a maximum radial thickness of the ventricular cover which may be desirable to minimize profile size of the prosthetic heart valve. As shown in FIGS. 20A-20D, the ventricular cover 3902 may have one, two, three, four, or more than four pleats that extend circumferentially around the body of the ventricular cover 3902, and which expand radially when the ventricular set of arms 310 transitions to a deployed configuration. In another set of embodiments, the pleats may extend axially along the ventricular cover such that when compressed, the pleats bend radially inward and/or outward in a controlled manner which may facilitate crimping into a smaller profile size. For example, the ventricular cover may have nine symmetrically oriented and axially-directed pleats, although in other embodiments the ventricular cover may have one, two, three, or more than three axially-directed pleats, including more than nine axially-directed pleats. In some embodiments, the ventricular cover may have both axially-directed and circumferentially-directed pleats.

Figure 21:
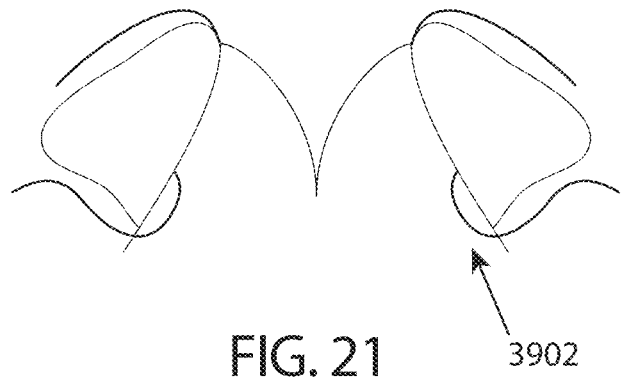
FIG. 21 illustrates a prosthetic heart valve with a support structure having a flared ventricular end, in accordance with an embodiment.
Figures 22A, 22B, 22C, 22D:
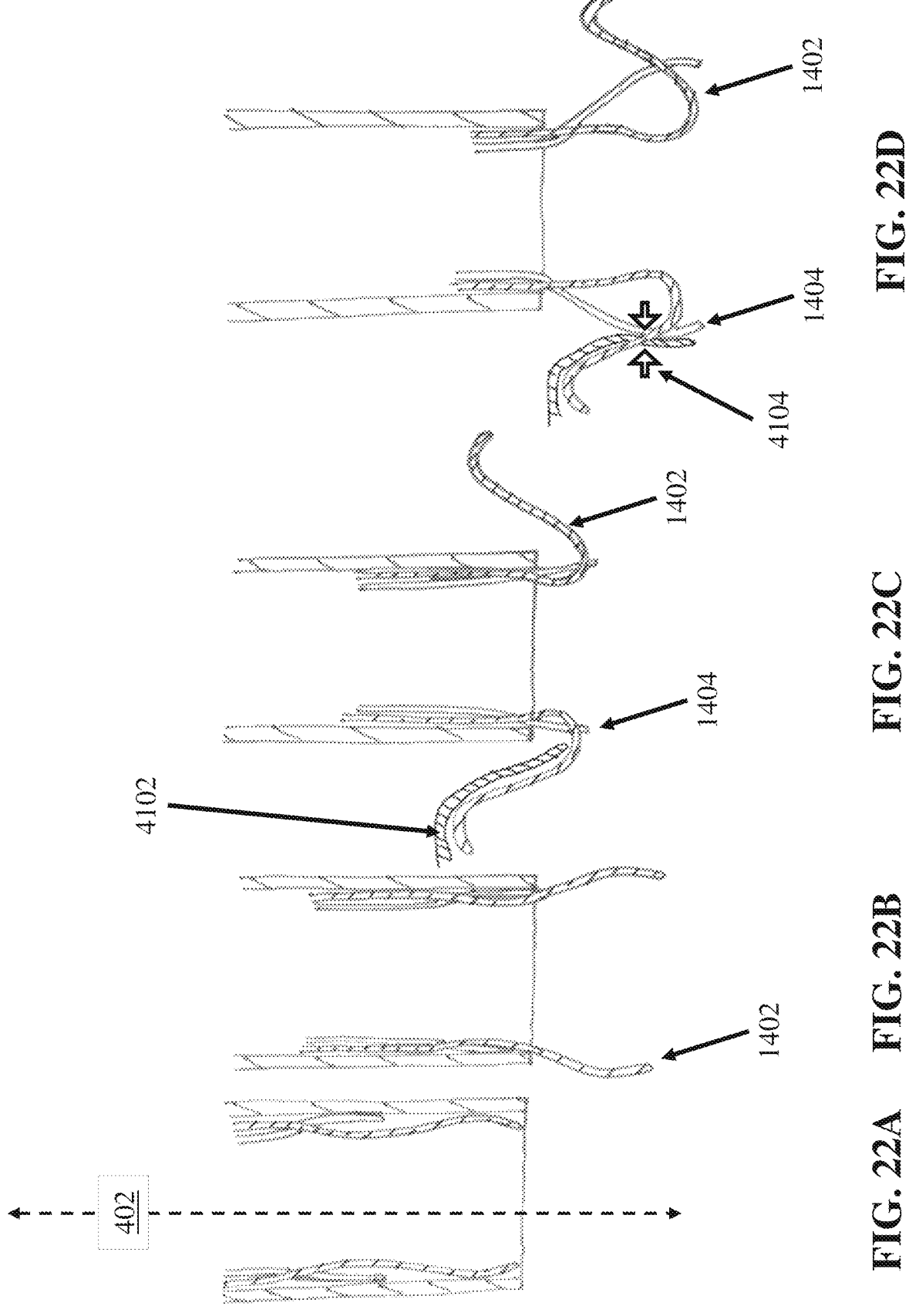
FIGS. 22A-22D illustrate the radial expansion of a ventricular set of arms during deployment, in accordance with an embodiment.

FIG. 21 depicts an embodiment in which the prosthetic heart valve has a flared ventricular end of a support structure of the prosthetic heart valve, which may be desirable to further reduce transvalvular blood flow and/or lead to a reduction in areas of stagnated blood flow and/or thrombosis formation proximate the prosthetic heart valve.

As described herein, in some embodiments, the valve includes a third set of arms. In some embodiments, the third set of arms provide support to the cover. In some embodiments, the third set of arms may be an atrial set of arms that are annularly-directed. In some embodiments, the third set of arms may be a ventricular set of arms that are annularly-directed. In some embodiments, the third set of arms may be an independent set of arms that are annularly-directed. In some embodiments, the third set of arms may be an atrial set of arms that are atrially-directed. In some embodiments, the third set of arms may be a ventricular set of arms that are atrially-directed. In some embodiments, the third set of arms may be an independent set of arms that are atrially-directed.

In some embodiments, for example, one or more of the third set of arms are configured to contact the native leaflets on a ventricular side of the native heart valve at a time prior to the time at which one or more of the third set of arms contact the native leaflets on an atrial side of the native heart. In some embodiments, the contact (e.g., contact between the ventricular cover and the native leaflets) creates an external seal. In some embodiments, the third set of arms do not contact the native leaflets. In some such embodiments, the third set of arms are configured to expand the cover (e.g., the ventricular cover which contacts the atrial side of the native leaflets).

In some embodiments, the ventricular set of arms and/or the third set of arms may exert a clamping force on the native leaflets. Advantageously, such clamping may, in some embodiments, provide an additional or alternative means for biodynamic fixation of the prosthetic heart valve to the native leaflets.

For example, in the embodiment illustrated in FIGS. 22A-22D, the bend region of the distal segments of the third set of arms 1402 (e.g., of the ventricular set of arms) that extends perpendicularly away from the central axis 402 of the elongate central passageway is in greater proximity to the ventricular end of the cylindrical portion of the one or more support structures than the bend region of the one or more arms of the third set of 1404 of the ventricular set of arms configured to contact the native leaflets on an atrial side of the native heart that extends generally towards the ventricular end of the one or more support structures. In some embodiments, staggering the location of the bend regions in this way allows for a damping force 4104 to be exerted on the native leaflet 4102 due to the opposing forces imparted on the native leaflet by the arms 1402 and the arms 1404.

Figure 23:
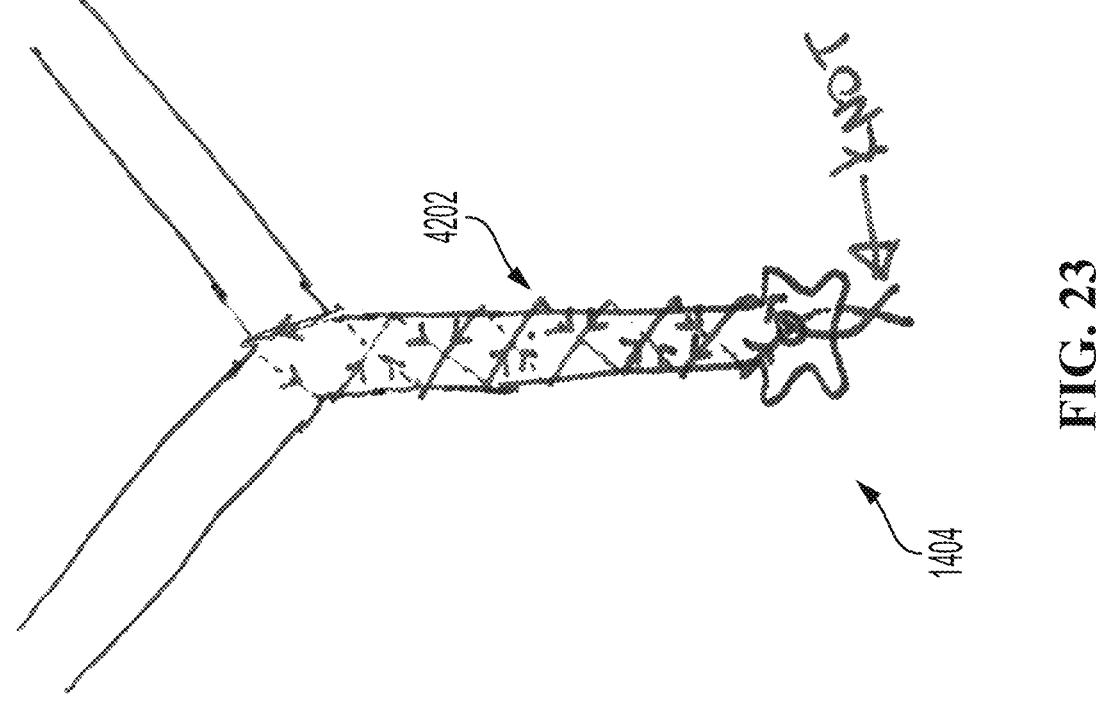
FIG. 23 illustrates a sewing pattern for attaching an arm of a ventricular set of arms to a cover for the ventricular set of arms, in accordance with an embodiment.

FIG. 23 shows a side view of one arm 1404 of the third set of arms of FIG. 9 with a distal fenestration and around which a suture pattern is depicted. One or more sutures 4202 may be used to attach one or more ventricular covers in such a way that only one knot is tied at the distal end of the arm 1404. In some embodiments, the may have one or more than one fenestration, for example, two fenestrations located at the distal end may allow better fixation of sutures.

Figure 24:
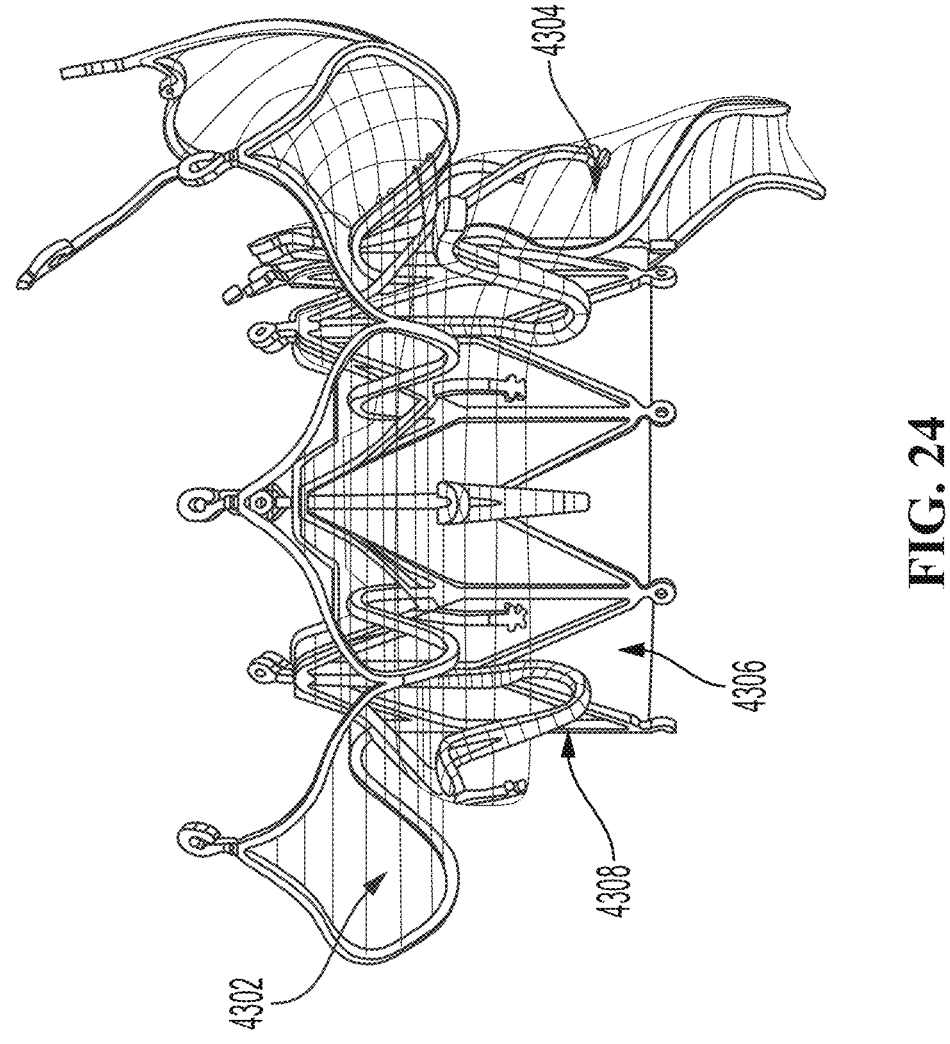
FIG. 24 illustrates a side view of an cover attached to an atrial set of arms, a cover attached to a ventricular set of arms, and a cover attached to a cylindrical portion of an elongate central passageway of a prosthetic heart valve, in accordance with an embodiment.

FIG. 24 shows the support structures 300 of prosthetic heart valve of FIG. 3-FIG. 7 which further includes an atrial cover 4302, a ventricular cover 4304, a cylindrical cover 4306 configured to cover an inner surface of the cylindrical portion of the prosthetic heart valve and several sleeves 4308 configured to cover each of the third set of arms of FIG. 9. The sleeves may provide a more atraumatic surface to further prevent damage to the native leaflets (e.g., perforation due to wear over time). In a preferred embodiment, the prosthetic heart valve includes sleeves 4308, coveting each of the atrial-directed arms. In another set of embodiments, the prosthetic heart valve may include more or less than six sleeves 4308. For example, nine sleeves 4308 may be used to cover the six atrial-directed arms and the three ventricular-directed arms. In another set of embodiments, each sleeve 4308 may be configured to cover only a portion of one or more arms of the ventricular set of arms, for example, only a distal portion of the atrial-directed arms. The sleeves may have an open or closed distal end. In some embodiments, the sleeves may be connected to the atrial cover, the ventricular cover, and/or the cylinder cover.

Any of the covers or sleeves previously described may be made of a biocompatible polymer material, such as polyester, nylon, or polytetrafluoroethylene, an elastomeric material such as silicone rubber, biological tissue such as porcine or bovine tissue, or any other flexible, biocompatible material. The covers or sleeves may be attached to any portion or portions of the prosthetic heart valve by using suture, thread, string, wire, or other type of line, through the use of heat to weld, stake, or melt the cover or sleeves material, through the use of hook and loop connection, or by any other means.

Figures 25, 26:
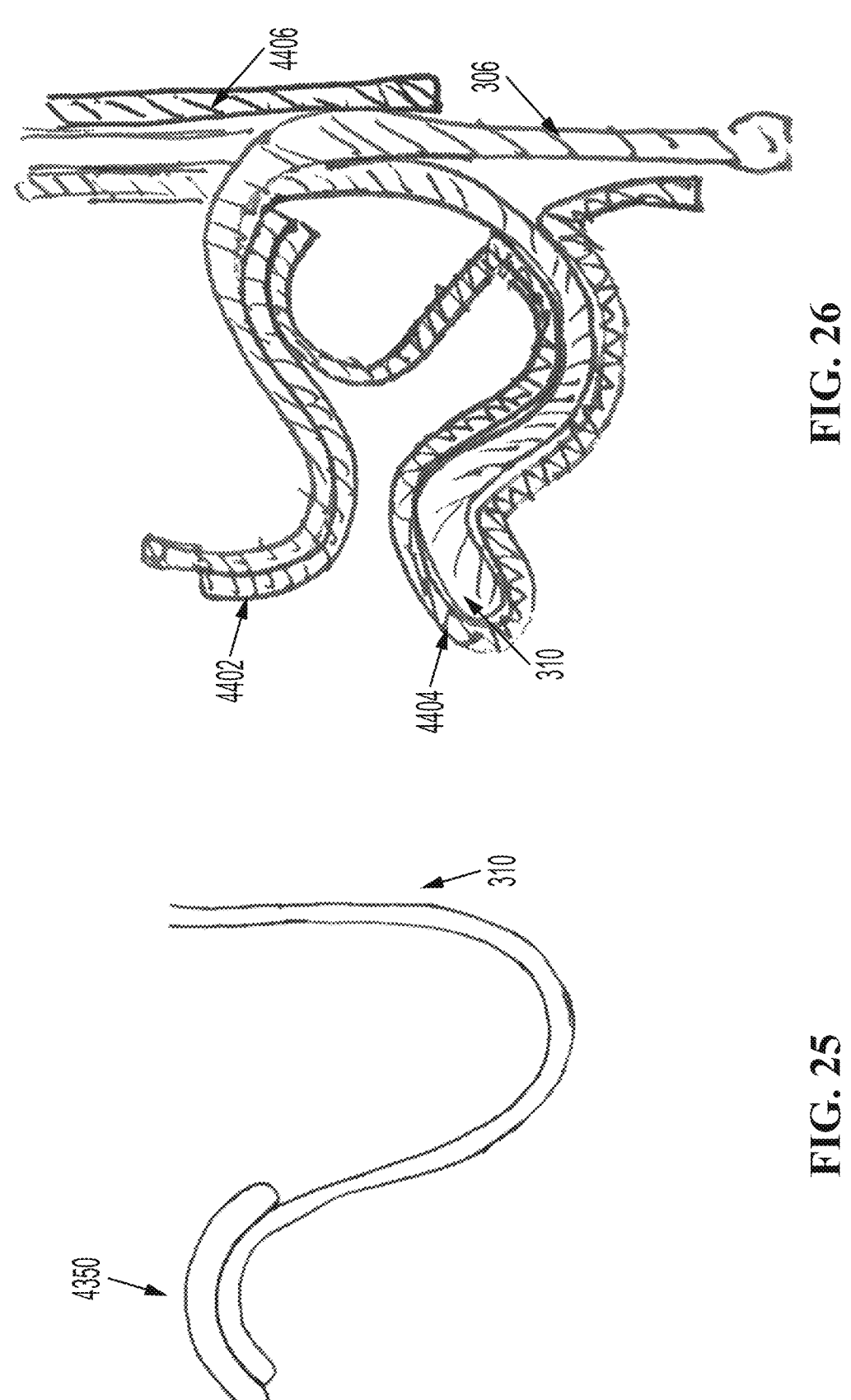
FIG. 25 is a cross-sectional view of a pad associated with a set of arms, according to one set of embodiments.
FIG. 26 is a side cross-sectional view of a prosthetic heart valve having an atrial set of arms, a ventricular set of arms, and one or more covers attached to the atrial set of arms and the ventricular set of arms, in accordance with an embodiment.

In some embodiments, one or more pads may be attached to the ventricular set of arms. As shown in FIG. 25, a pad 4350 may be attached to the atrial surface of the ventricular arms 310 to prevent direct contact of the ventricular arm with the native leaflet. In some embodiments, the pads may wrap around the distal end of the ventricular atm to contact at least a portion of the ventricular surface of the ventricular arm. The pads may be made of any kind of compliant material, such as a polyurethane foam, silicone, hydrogel, other polymer foam, bioabsorbable material, polyester fabric, and the like. In some embodiments, the pads may be attached to the ventricular arms using suture or other form of wire or line. In some embodiments, the ventricular skirt may have one or more extensions that extend to the distal end of one or more ventricular arms. The one or more extensions may cover all or a portion of one or more of the ventricular arms. The one or more extensions may be used in combination with a pad or sleeve or on its own. The one or more extensions may assist recapture of the ventricular arms into a delivery catheter by preventing any feature on the ventricular arm (e.g., a pad on the distal end) from catching on the edge of the delivery catheter. While the description above generally relates to one or more pads associated with a ventricular set of arms, one of ordinary skill in the art would understand, based upon the teachings of this specification, that one or more pads may be associated with a ventricular set of arms an atrial set of arms and/or a third set of arms.

FIG. 26 shows a side cross-sectional view of an embodiment wherein the atrial set of arms 306 has an atrial cover 4402 configured to contact a ventricular side of the atrial set of arms 306. The ventricular set of arms 310 has a ventricular cover 4404 configured to both contact an outer surface of the ventricular set of arms 310 and encompass one or more of the arms of the ventricular set of arms 310, and the ventricular cover 4404 is further configured to expand in a radial direction when moved into a deployed configuration. As shown In some such embodiments, the atrial set of arms 306 extends from a cylindrical portion of a support structure of the prosthetic heart valve, which has a cylindrical cover 4406 configured to cover an inner surface of the cylindrical portion.

Prosthetic Leaflets

Figure 27:
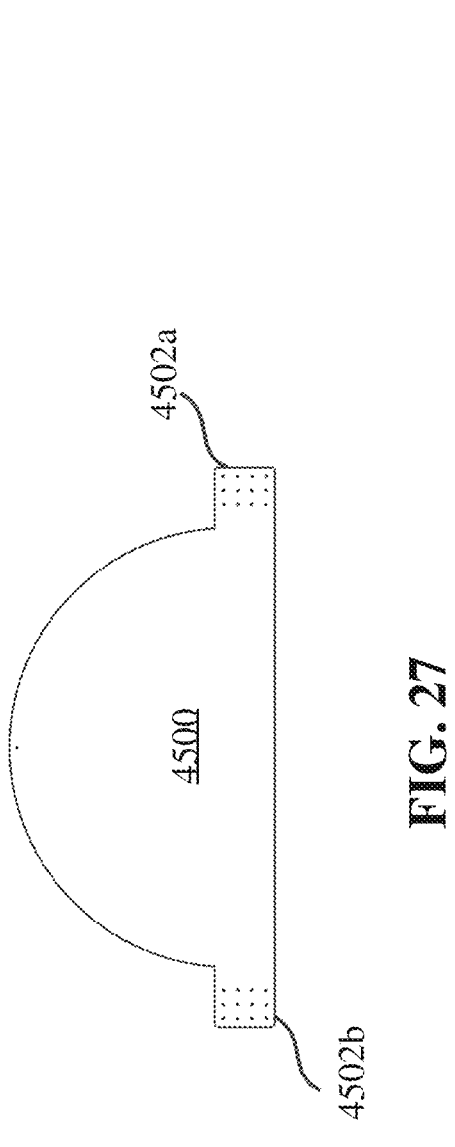
FIG. 27 is a CAD drawing of a top view of a leaflet of a prosthetic heart valve, in accordance with an embodiment.

FIG. 27 depicts the top view of a prosthetic leaflet 4500 for the prosthetic heart valve disclosed herein, which includes a main semi-circular shaped body, a first laterally-extending tab 4502*a*, a second laterally-extending tab 4502*b* (the tabs are referred to collectively as 4502), and one or more fenestrations, which may be used as an assembly aid or to facilitate attachment of the tabs to portions of the prosthetic heart valve, for example, using suture, thread, string, wire, etc.

In some embodiment, the prosthetic heart valve may further include a second prosthetic leaflet having a first laterally-extending tab and a second laterally-extending tab, and a third prosthetic leaflet having a first laterally-extending tab and a second laterally-extending tab. According to some embodiments, the first laterally-extending tab of the first prosthetic leaflet is configured to contact the second laterally-extending tab of the third prosthetic leaflet, the second laterally-extending tab of the first prosthetic leaflet is configured to contact the first laterally-extending tab of the second prosthetic leaflet, and the first laterally-extending tab of the third prosthetic leaflet is configured to contact the second laterally-extending tab of the second prosthetic leaflet.

Cylinder Covers

Figure 28:
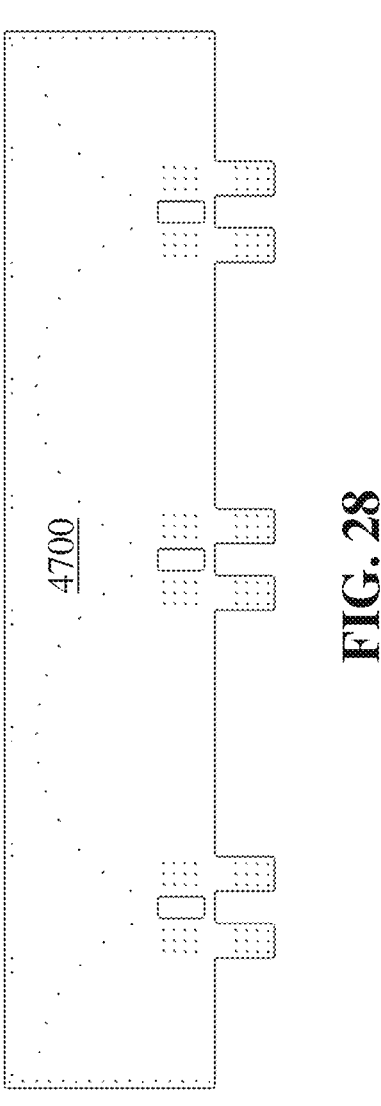
FIG. 28 is a CAD drawing of a top view of a cylinder cover for a prosthetic heart valve, in accordance with an embodiment.
Figures 29, 30, 31:
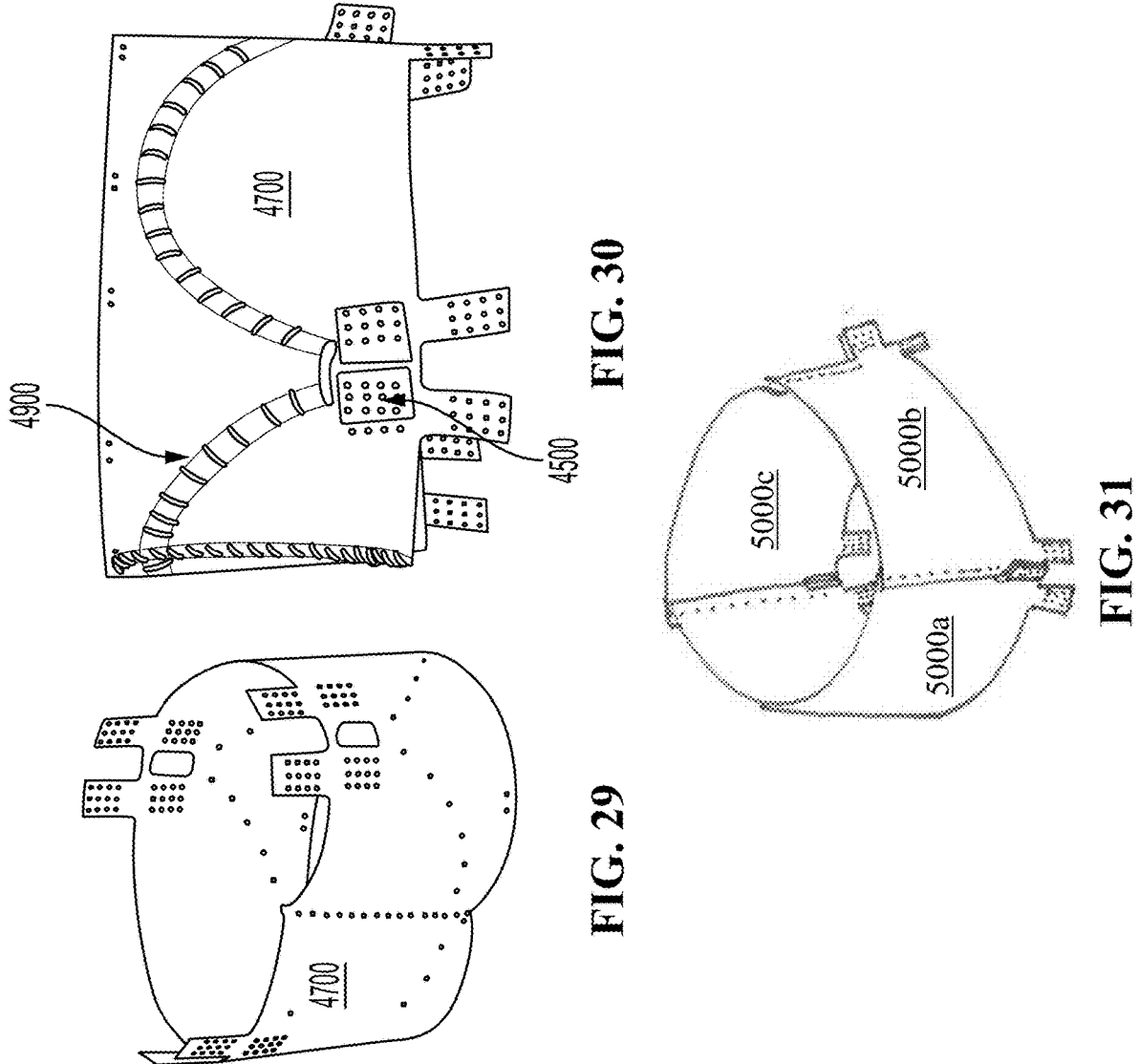
FIG. 29 is a perspective view of a cylinder cover for a prosthetic heart valve, in accordance with an embodiment.
FIG. 30 is a perspective view of three leaflets attached to a cylinder cover for a prosthetic heart valve, in accordance with an embodiment.
FIG. 31 is a perspective view of a cylinder cover for a prosthetic heart valve that includes three covers, in accordance with an embodiment.
Figure 32:
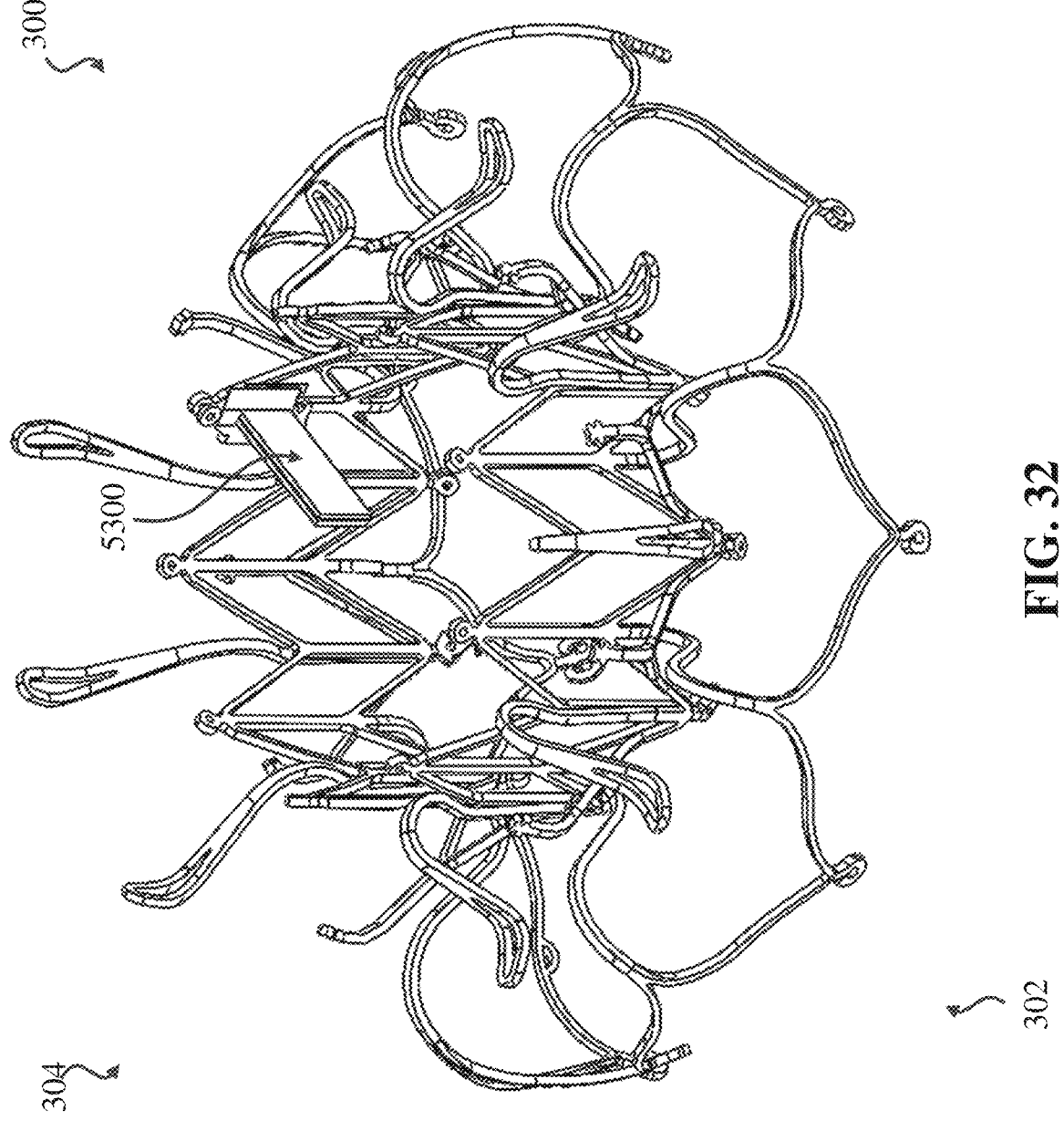
FIG. 32-FIG. 36 illustrate different views of a prosthetic heart valve that includes one or more brackets in an interior portion of the prosthetic heart valve, in accordance with an embodiment.
Figures 33, 34:
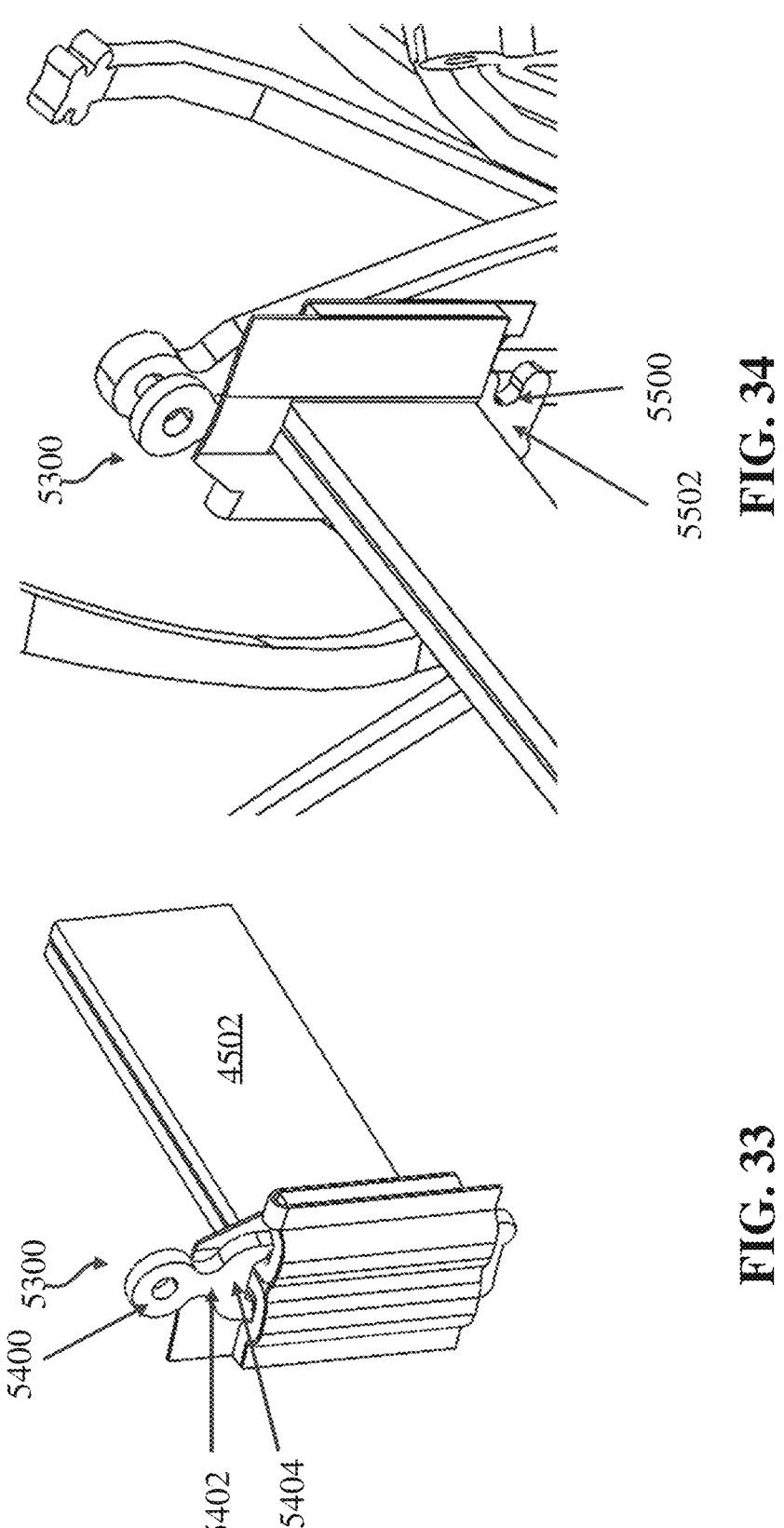
Figure 35:
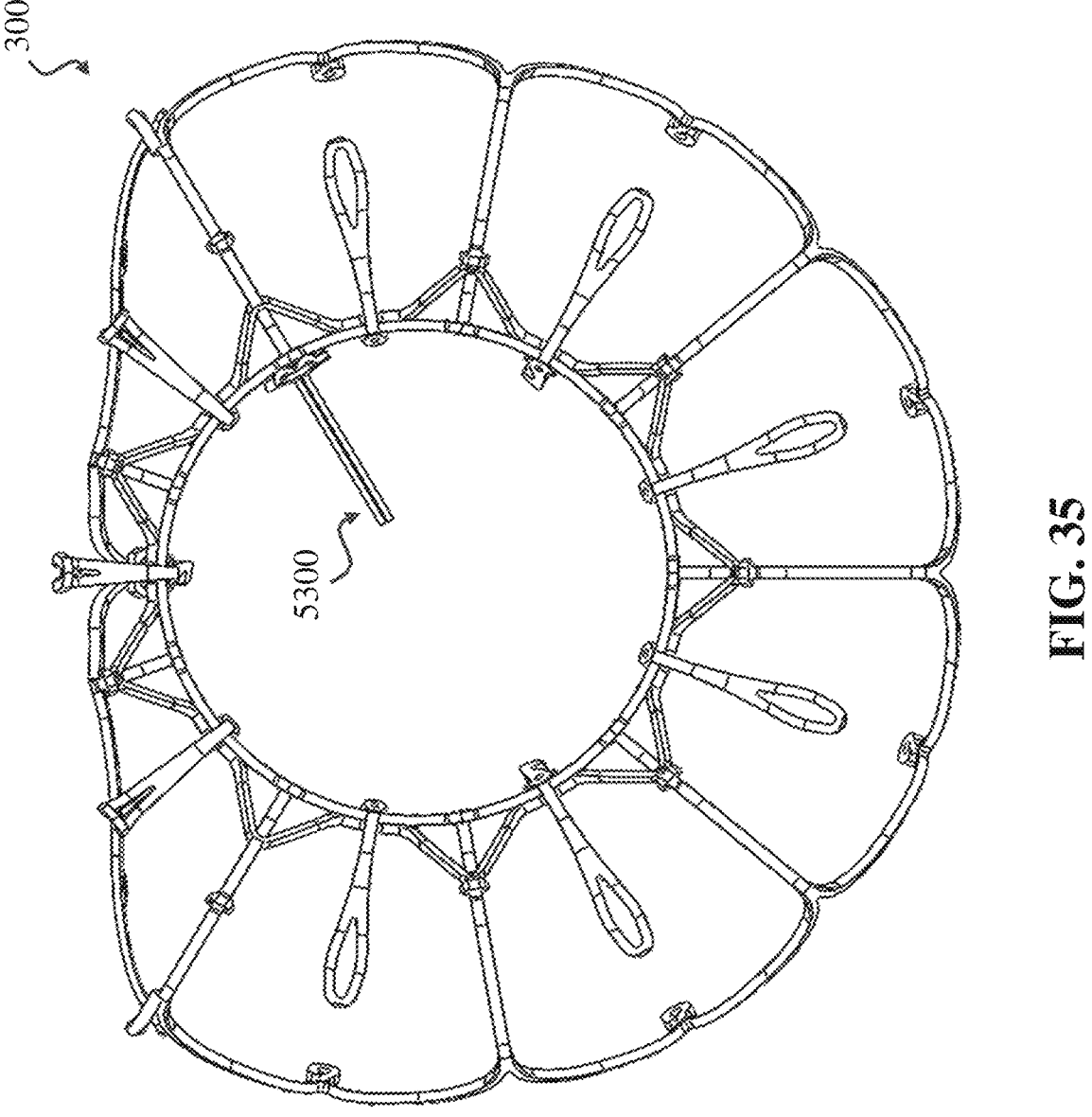

FIG. 28 depicts the top view of a two-dimensional cylinder cover 4700 configured to contact an inner surface of a cylindrical portion of one or more support structures 300 of a prosthetic heart valve. Although described as a "cylinder", the cylinder cover 4700 may or may not be cylindrical in shape. For example, the cylinder cover 4700 may have a cross-sectional shape that is oval, oblong, or crescent-shaped. The cylinder cover 4700 includes a first side and a second side, in which the first and second sides are configured to be placed adjacent one another to create a continuous circumference, as depicted in FIG. 29. The cylinder cover 4700 is configured to be placed on the inner surface of the cylindrical portion of the one or more support structures 300. In some embodiments, the cylinder cover 4700 may be configured to contact an outer surface of the cylindrical portion of the one or more support structures 300. The cylinder cover 4700 may have one or more fenestrations through which a suture (or thread, string, wire, etc.) may be passed to attach the cylinder cover to one or more support structures 300. The one or more fenestrations may also aid in alignment of mating components during assembly.

The prosthetic leaflets can, in some embodiments, be configured to contact an inner surface of the cylinder cover 4700 of FIG. 29, wherein the tabs of the prosthetic leaflet 4500 are configured to extend through one or more fenestrations of the cylinder skirt 4700, as depicted in FIG. 30. Also shown in the embodiment of FIG. 30 are sutures 4900 used to attach the prosthetic leaflets 4500, 4600, 4602 to the cylinder skirt 4700 approximately along the semi-circular edges of the prosthetic leaflets. In such a way, the non-attached edges of the prosthetic leaflets may move radially inward and outward in response to blood flow when implanted in a native heart.

FIG. 31 depicts an embodiment of a cylindrical cover 5000 which includes three prosthetic leaflets 5000*a*, 5000*b*, 5000*c* that each have a first side and a second side, and which together are configured to form an assembled cylinder cover. In the embodiment of FIG. 31, the first side of the first prosthetic leaflet 5000*a* is configured to attach to the second side of the third prosthetic leaflet 5000*c*, the second side of the first prosthetic leaflet 5000*a* is configured to attach to the first side of the second prosthetic leaflet 5000*b*, and the first side of the third prosthetic leaflet 5000*c* is configured to attach to the second side of the second prosthetic leaflet 5000*b*, as depicted in FIG. 31. Each cylinder cover further includes a first laterally-extending tab and a second laterally-extending tab, which may be configured to extend radially outward from an outer surface of the assembled cylinder cover, as shown in FIG. 31. However, in some embodiments, the laterally-extending tabs may be configured to extend radially inward towards the central axis of the elongate central passageway.

In some embodiments, one cover of a three-piece cylinder cover comprises an atrial side of the cylinder cover that includes three spices. In some embodiments, one cover of a three-piece cylinder cover comprises an atrial side of the cylinder cover that includes three spices and comprises a ventricular side that includes a region of lesser material than shown in FIG. 31, which may be desirable to prevent stagnation of blood on the ventricular side of the prosthetic heart valve.

Brackets for Prosthetic Leaflets

Figure 37:
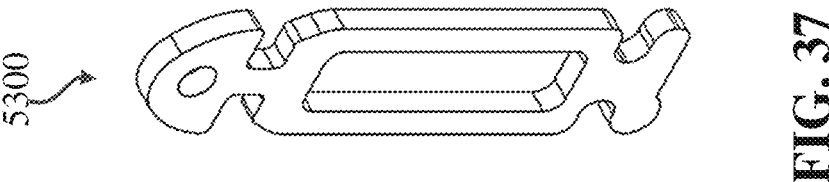
FIG. 37 illustrates a CAD drawing of a bracket for a prosthetic heart valve, in accordance with an embodiment.
Figure 36:
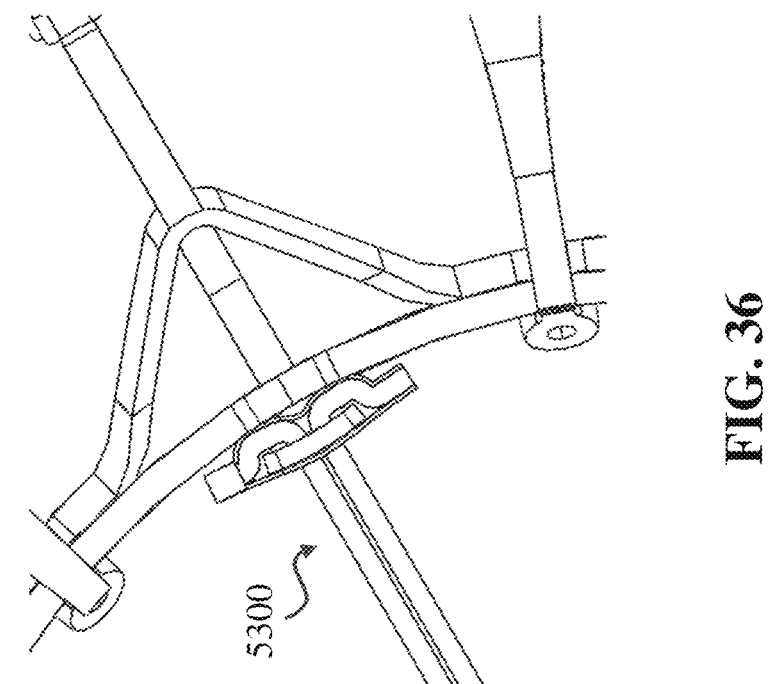

The embodiment shown in FIG. 32-FIG. 36 comprises a bracket 5300 that is configured to support attachment of the laterally-extending tabs of the prosthetic leaflets 4500 of FIG. 27 to the prosthetic heart valve. In a preferred embodiment, the prosthetic heart valve includes three brackets 5300 that are located at the three commissures of the prosthetic heart valve. In another set of embodiments, the prosthetic heart valve may include one, two, or more than three brackets 5300, depending on the desired result. The bracket 5300, also depicted in FIG. 37, includes a head portion 5400 with a single fenestration, a neck portion 5402 inferior to the head portion 5400 with a width that is less than a width of the head portion 5400 and is also less than a width of the frame portion 5404, a frame portion 5404 inferior to the neck portion 5402, an ankle portion 5500 with a width that is less than the width of the frame portion 5404 and is also less than a width of a foot portion 5502 that is inferior to the ankle portion 5500. The head portion 5400 of the bracket 5300 includes a single fenestration, which may be desirable to facilitate attachment to the least one support structure, for example, by laser welding, riveting, suturing, mechanical connection, or other means of attachment. The narrower width of the neck portion 5402 and/or ankle portion 5500 of the bracket 5300 may be advantageous to facilitate attachment of the bracket to the one or more support structures, for example, by using a thread-like element such as a suture. The bracket may be made from a metal (such as Nitinol, stainless steel, titanium, or gold), plastic (such as PTFE, PEEK, nylon, polyurethane, etc.), rubber (such as silicone), or other stiff material. In a preferred embodiment, the bracket 5300 may be laser cut from a Nitinol or Nitinol alloy hypotube. In some embodiments, the bracket has only a frame portion. In some embodiments, the bracket may be attached directly to the cylinder skirt, e.g., as a grommet.

Figures 38, 39:
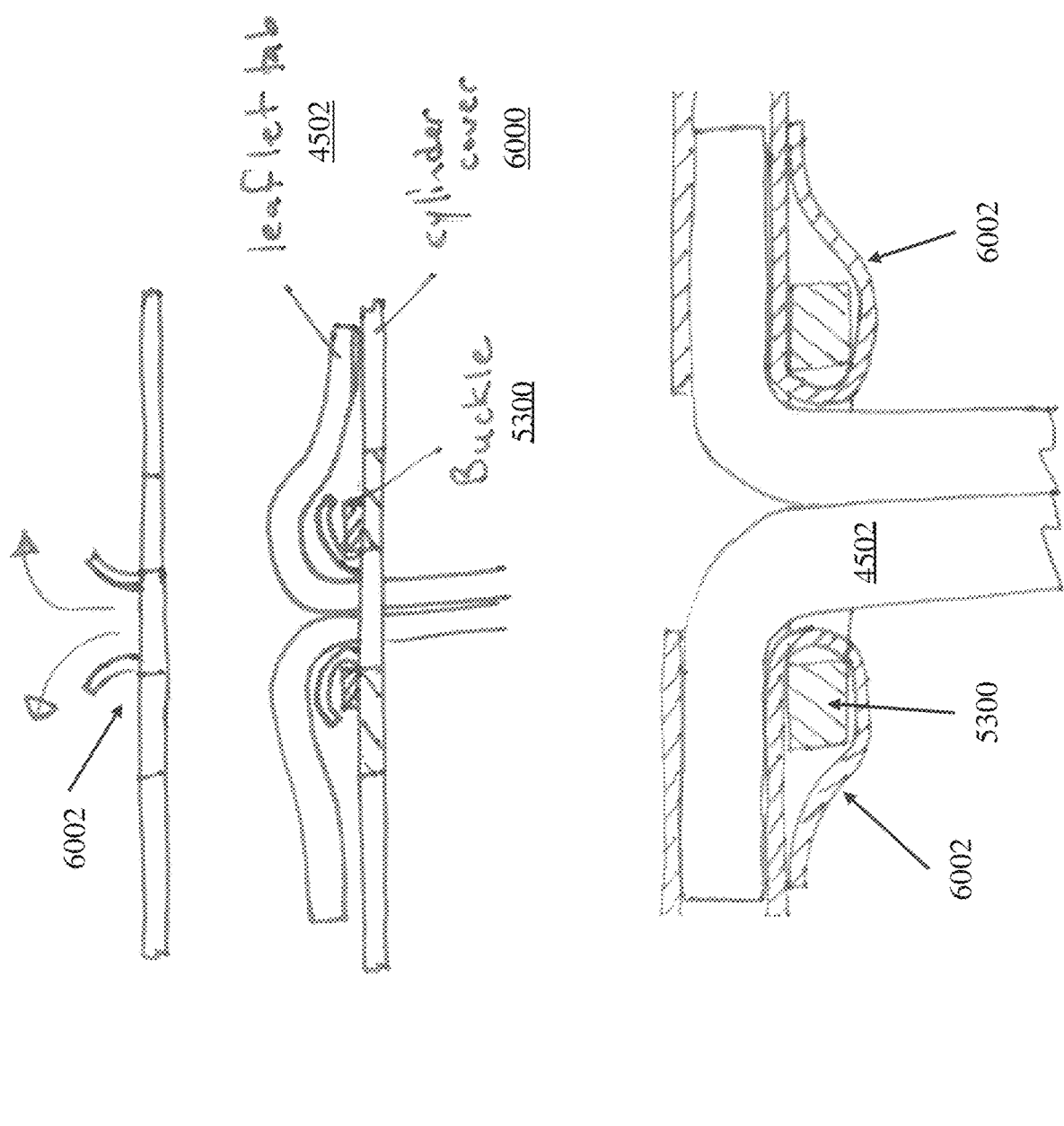
FIG. 38 is a top view of the cylinder cover of FIG. 28 in communication with a bracket and prosthetic leaflets of a prosthetic heart valve, in accordance with an embodiment.
FIG. 39 is a top, cross-sectional view of a bracket for a prosthetic heart valve having two frame sleeves, in accordance with an embodiment.

As shown in FIG. 32-FIG. 36, the bracket 5300 may be configured to receive the laterally-extending tabs 4502 of the prosthetic leaflets 4500 through the frame portion of the bracket 5300. For example, advantageously, passing the laterally-extending tabs of the prosthetic leaflets through the bracket may reduce the stress that would otherwise be applied to the commissures of the prosthetic leaflets if they were sutured directly to the cylinder skirt, thus extending the lifetime of the prosthetic leaflets. The bracket 5300 may be further configured to contact an outer surface or an inner surface of the cylinder cover, such as the cover 4700 depicted in FIG. 28, where a circumference of the frame portion 5404 may be aligned with a window portion of the cylinder cover. In some embodiments, one or more cylinder covers 6000 may have window tabs 6002 extending within the window portion as shown in FIG. 38 and are configured to bend outward from the cylinder cover 6000 to wrap around the frame portion 5404 of the bracket 5300 which is contacting an outer surface of the cylinder cover, as shown. The bracket may be advantageous, in some embodiments, by improving and securing alignment of the prosthetic leaflets with the cylindrical portion of the prosthetic heart valve. The bracket may also improve ease of assembly or allow flexibility in the manufacturing process by allowing subassemblies of prosthetic leaflets and brackets to be prepared in advance of attaching to the cylindrical portion of the prosthetic heart valve.

In the embodiment shown in FIG. 39, the window tabs 6002 may be configured to bend inward from the cylinder cover to wrap around the frame portion 5404 of the bracket 5300 which is contacting an inner surface of the cylinder cover.

The embodiments of FIG. 38, and FIG. 39 may be realized through use of preferably one, two, or three cylinder covers such as the ones shown in FIG. 28 and FIG. 31, or through use of cylinder covers of different design or with more than three cylinder covers. A potential advantage of the use of a cylinder cover that includes three cylinder covers to realize the embodiments of FIG. 38, and FIG. 39, is that the window tabs 6002 previously described may be of any length, which may be advantageous to more completely cover the surface of the frame and thereby protect the prosthetic leaflet from contacting the frame.

The one or more cylinder covers previously described may further include one or more atrial-directed tabs which may be configured to bend away from the central axis of the elongate central passageway and contact the laterally-extending tabs 4502 of the prosthetic leaflet outside the cylindrical portion of the prosthetic heart valve. In this way, the atrial-directed tabs of the one or more cylinder covers may be configured to prevent contact between any portion of the prosthetic leaflet and the one or more support structures of the prosthetic heart valve, which may be advantageous to reduce wear and extend the longevity of the prosthetic leaflets. In some embodiments, the atrial-directed tabs of the one or more cylinder covers may be configured to bend toward the central axis of the elongate central passageway into an interior portion of the cylindrical portion of the prosthetic heart valve.

In some embodiments, such as the one shown in FIG. 28, the cylinder cover may include one or more window portions configured to allow passage therethrough of the laterally-extending tabs 4502 of the prosthetic leaflets. Such embodiments may further include one or more frame sleeves configured to encompass at least a portion of a cross-sectional circumference of the frame portion of the bracket. The frame sleeves may be made from bioprosthetic tissue (e.g., bovine, porcine, etc.) or may be made from synthetic material (e.g. polyester, nylon, polyurethane, ePTFE, hydrogel, silicone rubber, etc.). FIG. 40 depicts an embodiment comprising two frame sleeves 6302, each of which includes a sheet of material that is configured to wrap around a vertically-oriented member of the frame such that two opposing sides of the sheet contact one another outside a central window portion of the frame portion 5404, and the opposing sides may be attached to one another, for example, using suture, thread, wire, line, etc. In another set of embodiments, one or more sleeves may wrap around only a portion of one or more members of the frame without its ends coming into contact.

As shown in FIG. 41, the laterally-extending tabs 4502 of the prosthetic leaflet may be configured to pass through the central window portion of the bracket of FIG. 40 and contact an outer surface of one or more frame sleeves 6302, which may be desirable to prevent contact between the prosthetic leaflets and the bracket, for example to reduce wear and extend the longevity of the prosthetic leaflets. The prosthetic leaflets of FIG. 41 may also be configured to bend in opposing directions towards an outer surface of the cylinder cover, and in some embodiments may be configured to contact the outer surface of the cylinder cover. In some embodiments, such as the one shown in FIG. 41, the bracket 5300 and the frame sleeves 6302 are located in an interior portion of the cylindrical portion 6400 of the prosthetic heart valve. In some embodiments, such as the one shown in FIG. 42, the bracket 5300 and the frame sleeves 6302 are located in an exterior portion of the cylindrical portion 6400 of the prosthetic heart valve.

Figures 43A, 43B, 43C:
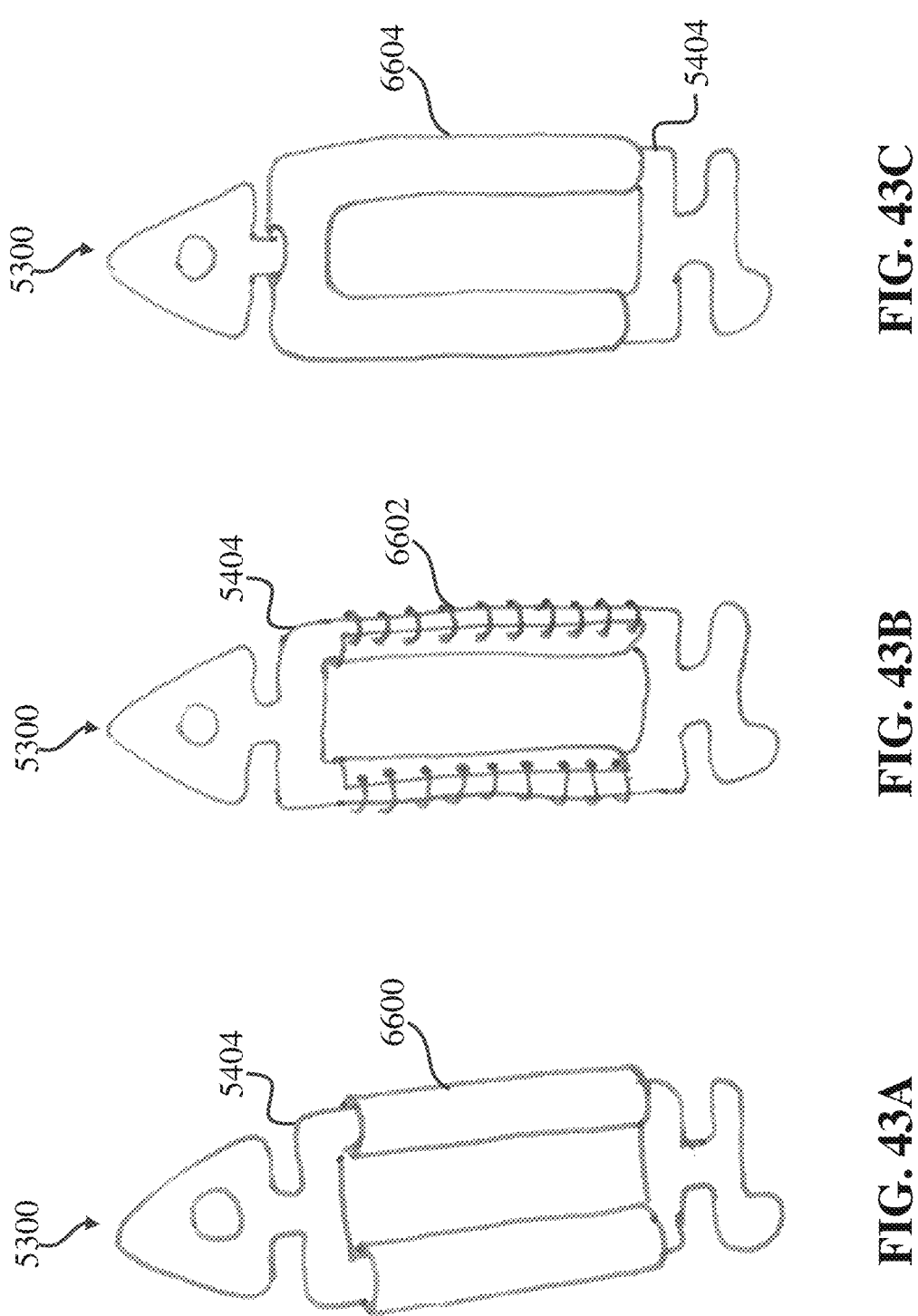
FIGS. 43A-43C illustrate several embodiments of a bracket of a prosthetic heart valve having one or more frame sleeves, in accordance with several embodiments.

FIGS. 43A-43C depict several embodiments of a bracket 5300 and one or more frame sleeves. The embodiment of FIG. 43A includes two frame sleeves 6600 that wrap around the entire cross-sectional circumference of the frame portion 5404 of the bracket 5300. The embodiment of FIG. 43B includes two frame sleeves 6602 that wrap around only a portion of the cross-sectional circumference of the frame portion 5404 of the bracket 5300 and are secured in place using suture, thread, wire, line, or similar means. The embodiment of FIG. 43C depicts a bracket 5300 with one frame sleeve 6604 that covers two vertically-oriented members of frame portion 5404 of the bracket 5300.

Figures 44A, 44B, 44C:
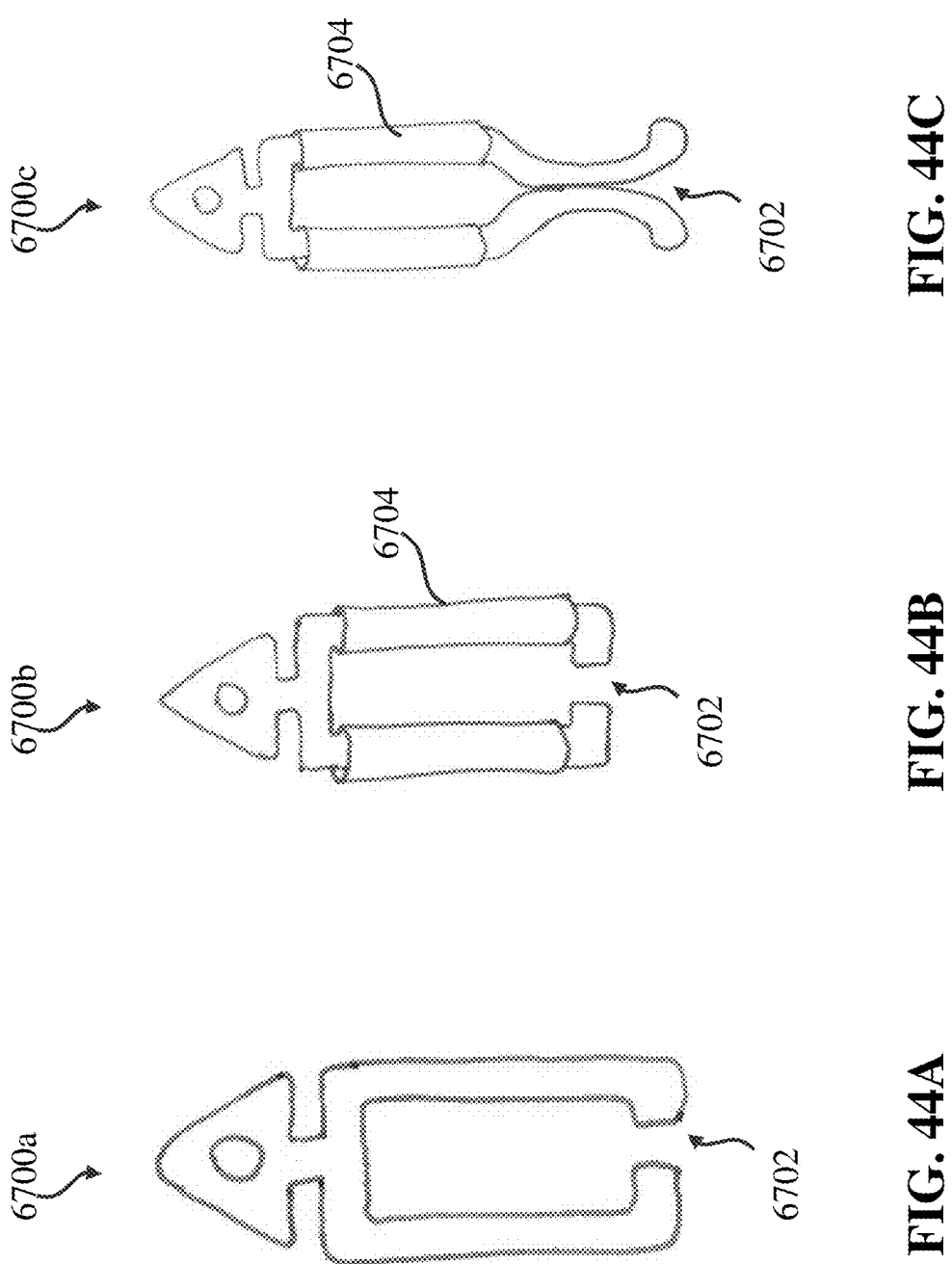
FIGS. 44A-44C illustrate several embodiments of a bracket of a prosthetic heart valve wherein a frame portion of the bracket does not form a continuous loop, in accordance with several embodiments.

FIGS. 44A-44C depict several embodiments in which the frame of the bracket 6700a, 6700b, 6700c does not form a continuous loop by inclusion of a gap 6702 in the perimeter of the frame, which may be advantageous to allow one or more frame sleeves 6704 to be easily attached to the bracket. For example, in the embodiment depicted in FIG. 44B and 44C, the frame sleeves 6704 include two frame sleeves which are each a continuous cylinder and which may be attached to the frame of the bracket 6700b, 6700c by passing the frame sleeves 6704 over an open end at gap 6702 of the frame of the bracket. The embodiment of FIG. 44C depicts a bracket 6700c in which the frame does not form a continuous loop and which further includes an ankle portion inferior to the frame portion with a width that is less than a width of the frame portion and less than a width of a foot portion located inferior to the ankle portion. The inclusion of an ankle portion in a bracket without a continuous loop frame may be desirable to facilitate attachment of the bracket to one or more support structures of the prosthetic heart valve. In another set of embodiments, the frame may have a gap on any portion of the frame, or the frame may have more than one gap, and in some embodiments the gap may be larger or smaller than what is depicted in FIG. 44A-44C. In some embodiments, the vertically-oriented members of the frame portion of the bracket are not parallel, but instead converge or diverge at an angle of between about 0 and 45 degrees. In another set of embodiments, the bracket may consist of only one or two vertically oriented members.

Figure 46:
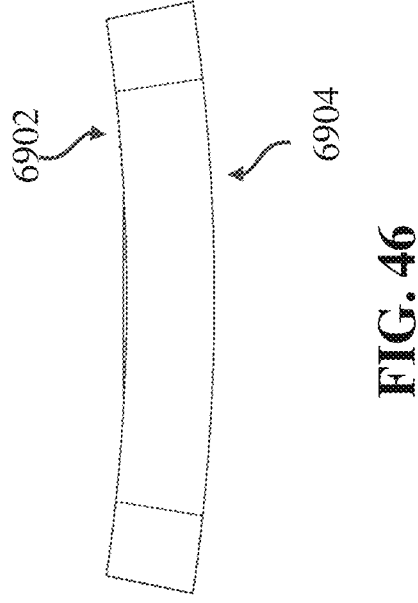
FIG. 46 is a top view of a bracket of a prosthetic heart valve, in accordance with an embodiment.
Figure 45B:
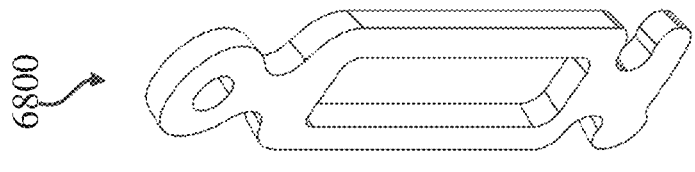
FIGS. 45A-45B illustrates two views of a bracket of a prosthetic heart valve, in accordance with an embodiment.
Figure 45A:
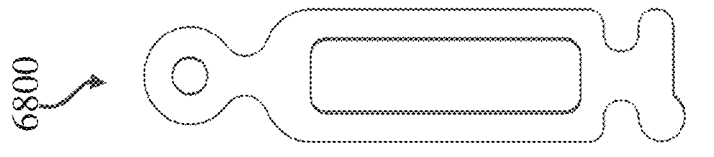

FIGS. 45A-45B depict an embodiment of a bracket 6800 wherein the head portion of the bracket has a generally circular exterior shape, which may be desirable to match the generally circular shape of a mating portion of one or more of the support structures of the prosthetic heart valve. In some embodiments, the bracket 6800 may have a first face 6902 with concave curvature and a second face 6904 with convex curvature, as depicted in FIG. 46, which may be desirable to improve contact between a portion of the laterally-extending tab of the leaflet and a portion of the prosthetic heart valve. In some embodiments, the ankle portion of the bracket has an asymmetric shape, such as a circular region on only one side of the ankle portion as shown in FIG. 45A and FIG. 45B, which may be desirable to facilitate identification of the concave and convex faces of the bracket.

Figures 47A, 47B, 48, 49:
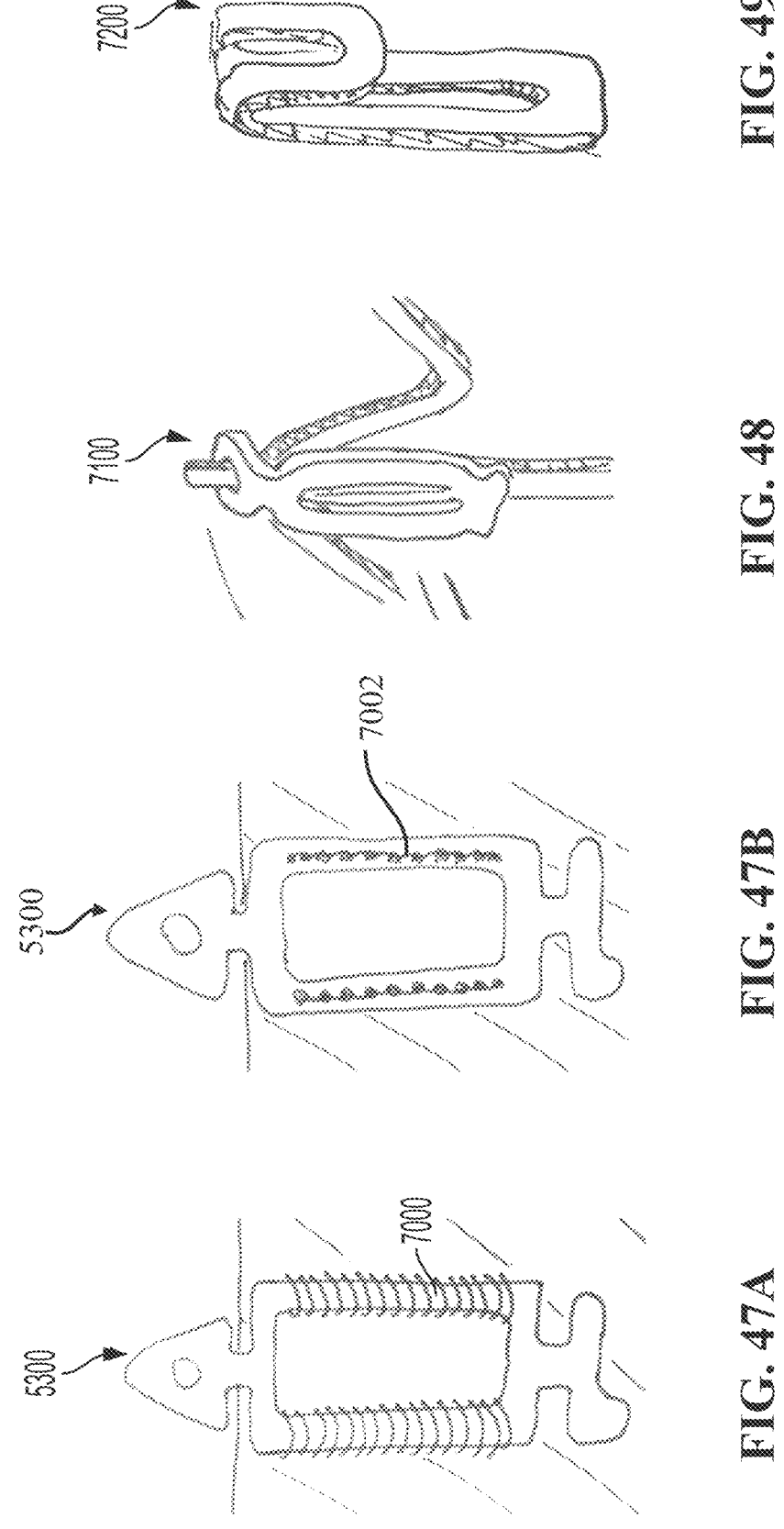
FIGS. 47A-47B illustrate two embodiments of a bracket of a prosthetic heart valve attached to a cylinder cover of the prosthetic heart valve, in accordance with two embodiments.
FIG. 48 illustrates a bracket of a prosthetic heart valve attached to a support structure of the prosthetic heart valve, in accordance with an embodiment.
FIG. 49 illustrates a perspective view of a bracket of a prosthetic heart valve attached to a support structure of the prosthetic heart valve, in accordance with an embodiment.

In some embodiments, the sleeve may be constructed from multiple windings of a thread-like element 7000 (e.g., a suture), which may be used to secure the frame to the one or more covers that extend within the elongate central passageway, as shown in FIG. 47A. In another set of embodiments, such as the one depicted in FIG. 47B, the frame of the bracket 5300 may have one or more fenestrations 7002 along one or more of the vertical members of the frame to facilitate connection to the one or more cylinder covers that extend within the elongate central passageway or directly to the one or more support structures, for example, using a thread-like element (e.g., a suture).

As shown in the embodiment of FIG. 48, the head portion of the bracket 7100 may be configured to have one or more bends such that a face of the head portion creates an angle with a face of the frame portion that is less than 180 degrees. The head portion may further include a fenestration that may be configured to mate with a member of the one or more support structures 300 of the prosthetic heart valve to facilitate attachment of the bracket 7100 to one or more support structures 300.

The embodiments of FIG. 49 depicts a bracket 7200 which includes an upper frame portion and a lower frame portion wherein the upper frame portion is configured to have one or more bends such that a face of the upper frame portion creates an angle with a face of the lower frame portion that is less than 180 degrees. For example, FIG. 49 depicts a bracket 7200 where the angle between the upper face and the lower face is approximately 0 degrees, although in other embodiments the angle may be greater than 0 degrees. In some embodiments, the bracket may be configured to engage with the one or more support structures of the prosthetic heart valve to facilitate attachment of the bracket to one or more support structures. In some embodiments, the distance between a second face of the lower frame portion of the bracket and a second face of the upper frame portion of the bracket is equal to or less than the thickness of the mating portion of one or more support structures which may be desirable to cause a force fit between the bracket and one or more support structures to facilitate attachment.

Figure 50:
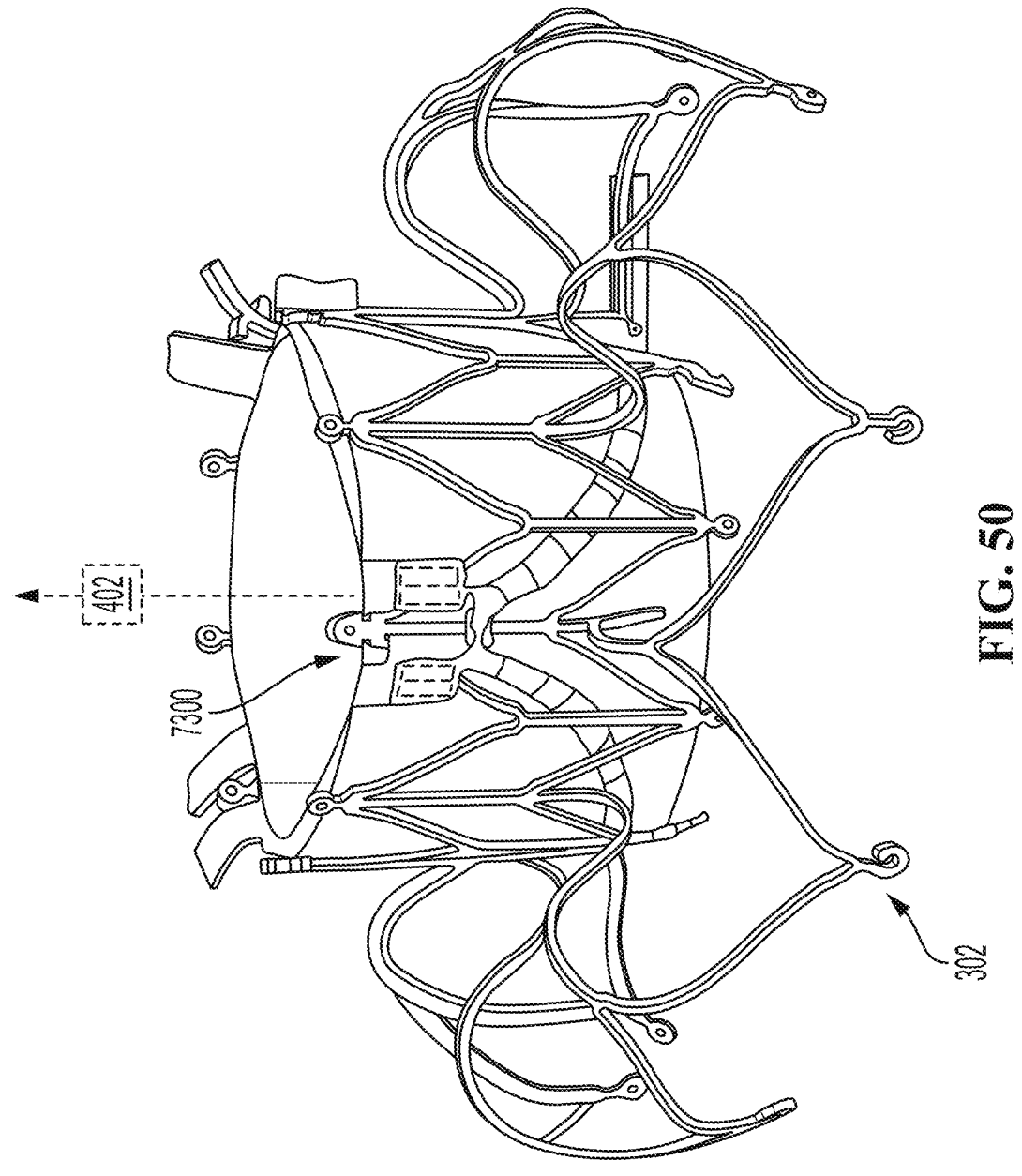
FIG. 50 is a perspective view of a support structure of a prosthetic heart valve wherein the bracket of FIG. 37 is located adjacent an outer surface of the support structure, in accordance with an embodiment.

In some embodiments, the bracket 7300 may be located such that a first face of the bracket that is closest to the central axis 402 of the elongate central passageway of the cylindrical portion of one or more support structures 300 is nearer to an outer edge of the one or more support structures than a second face of the bracket 7300 that is farther from the central axis 402 than the first face, as shown in FIG. 50. In some such embodiments, the laterally-extending tabs 4502 of the prosthetic leaflets may be configured to extend beyond a member of the one or more support structures before passing through the window portion of the bracket 7300, as depicted in the top cross-sectional view of FIG. 51. In some embodiments, the laterally-extending tabs 4502 of the prosthetic leaflets may be configured to contact an internal surface of the one or more support structures after first passing through the window portion of the bracket, as displayed in FIG. 51. In another set of embodiments, the laterally-extending tabs of the prosthetic leaflets may be configured to contact an external surface of the one or more support structures after first passing through the window portion of the bracket. In any of the aforementioned embodiments, one or more of the previously described frame sleeves may be configured to encircle a portion of the frame of the bracket and/or a portion of one or more members of the one or more support structures such that the laterally-extending tabs of the prosthetic leaflets contact the one or more frame sleeves instead of directly contacting the bracket or the one or more support structures.

Figures 51, 52:
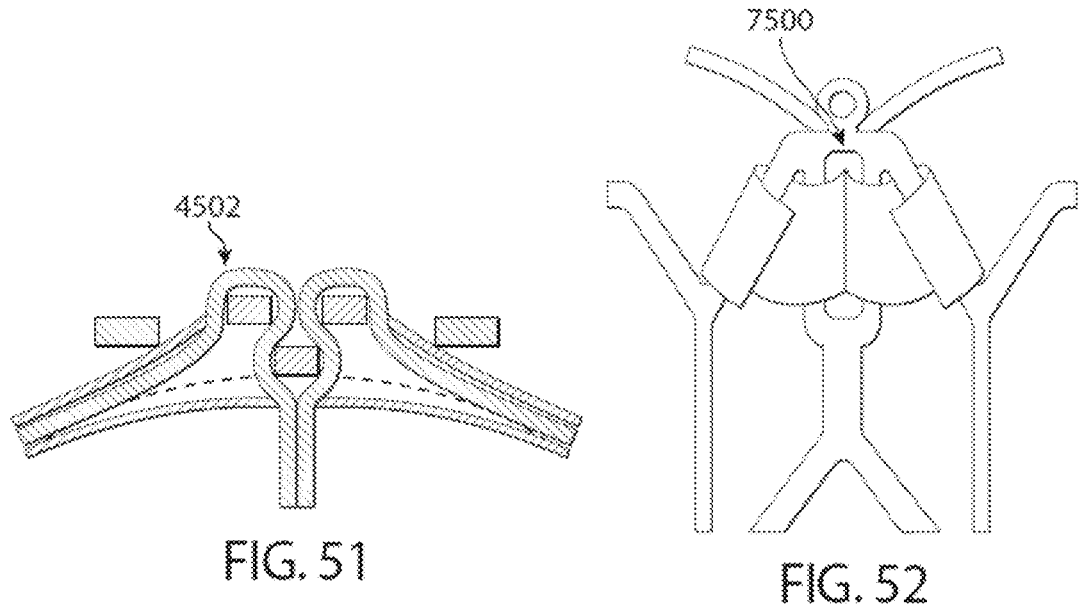
FIG. 51 is a top cross-sectional view of two leaflet tabs passing through a bracket where the bracket is positioned outside an elongate central passageway of a prosthetic heart valve, in accordance with an embodiment.
FIG. 52 illustrates a portion of a support structure of a prosthetic heart valve having one or more slots, in accordance with an embodiment.

FIG. 52 depicts an embodiment in which a support structure (e.g., 302 and/or 304) of the prosthetic heart valve includes one or more slots 7500 configured to receive the laterally-extending tabs 4502 of the prosthetic leaflets as an alternative to using the bracket previously described.

Prosthetic Heart Valve Assembly

Figure 53:
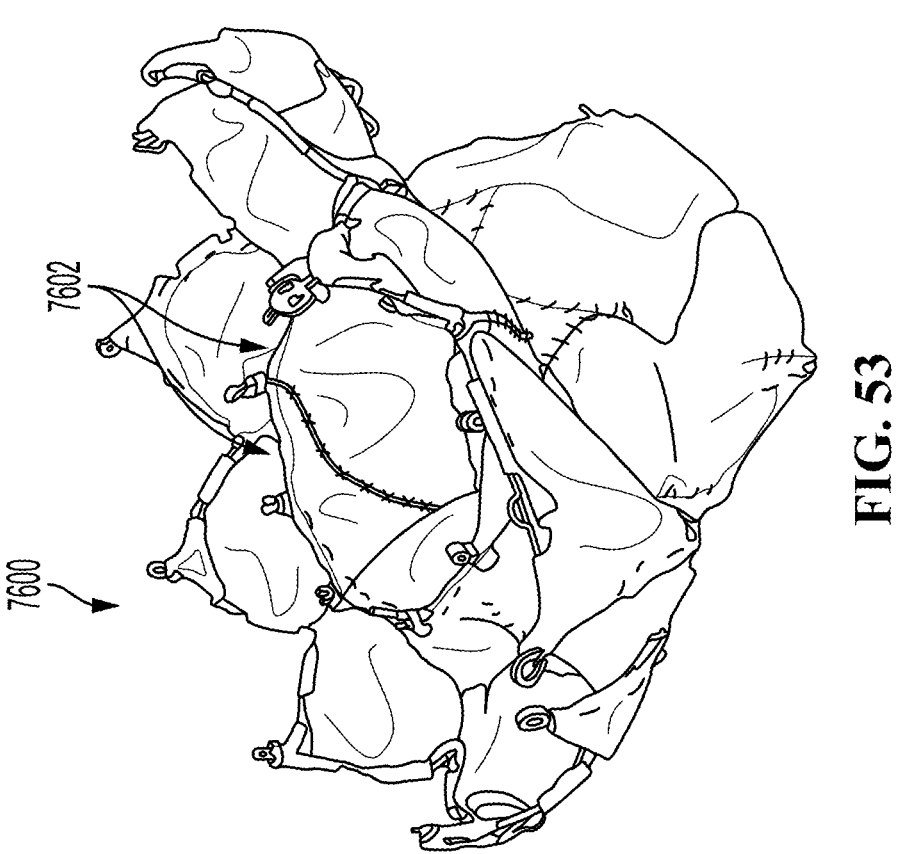
FIG. 53 illustrates a perspective view of several covers attached to support structures of a prosthetic heart valve, in accordance with an embodiment.

FIG. 53 shows a perspective view of the prosthetic heart valve 7600 including the support structures 300 (refer to FIG. 3-FIG. 7) and the atrial cover 2000 of FIG. 11, the ventricular cover 2802 of FIG. 16, the prosthetic leaflets 4500 of FIG. 27, and the cylinder cover 4700 of FIG. 28.

Figure 54:
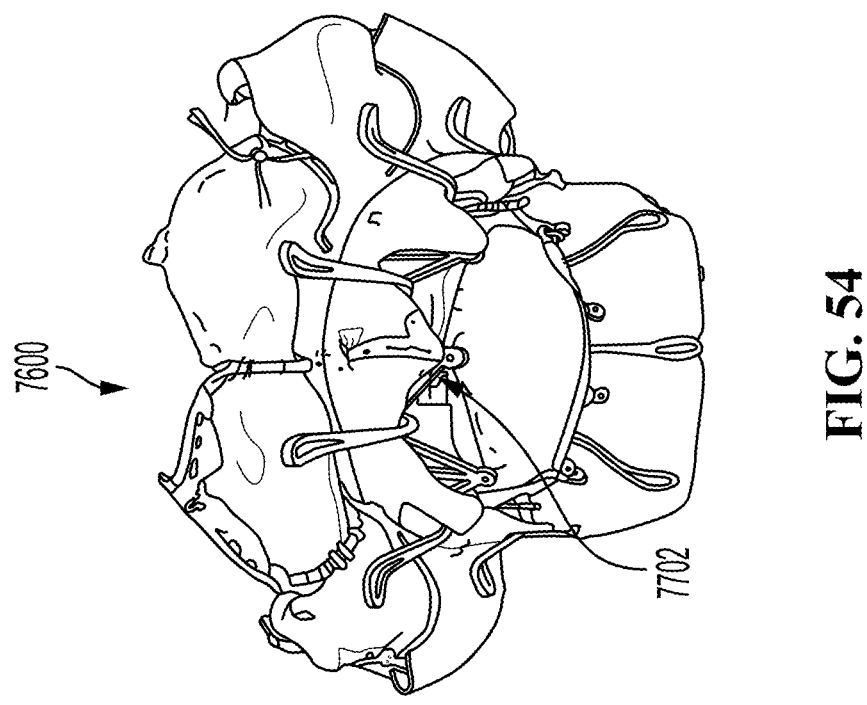
FIG. 54 illustrates another perspective view of several covers attached to support structures of a prosthetic heart valve, in accordance with an embodiment.

In some embodiments, one or more covers over one or more ventricular arms may be attached to the atrial end (e.g., along atrial perimeter 7602) of the cylindrical portion of one or more support structures 300 and the ventricular end (e.g., along portions 7702) of the cylindrical portion of one or more support structures 300 to prevent areas of blood stagnation on the ventricular side of the prosthetic heart valve, as shown in FIG. 54. This embodiment may also serve to strengthen attachment of the ventricular set of arms and the ventricular covers to the cylindrical portion or the one or more support structures.

In an illustrative embodiment, a prosthetic heart valve includes a first support structure with a cylindrical portion and an atrial set of arms, a second support structure including a ventricular set of arms, a ventricular cover configured to contact an outer surface of the ventricular set of arms, a cylinder cover configured to contact an inner surface of the cylindrical portion of the first support structure, three prosthetic leaflets configured to move radially inward and outward within the cylindrical portion of the first support structure in order to enable blood flow in only one direction, and six sleeves configured to cover each of the atrial-directed arms of the ventricular set of arms.

Additional Embodiments

Figure 55:
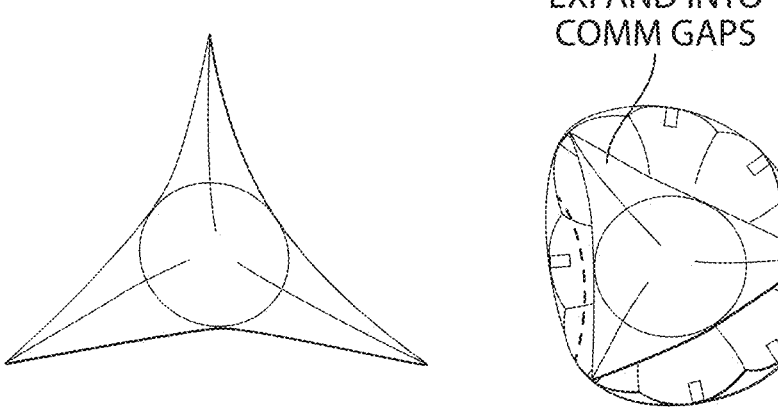
FIG. 55 is a top view of a prosthetic heart valve having an atrial set of arms that includes three arms, in accordance with an embodiment.
Figure 56:
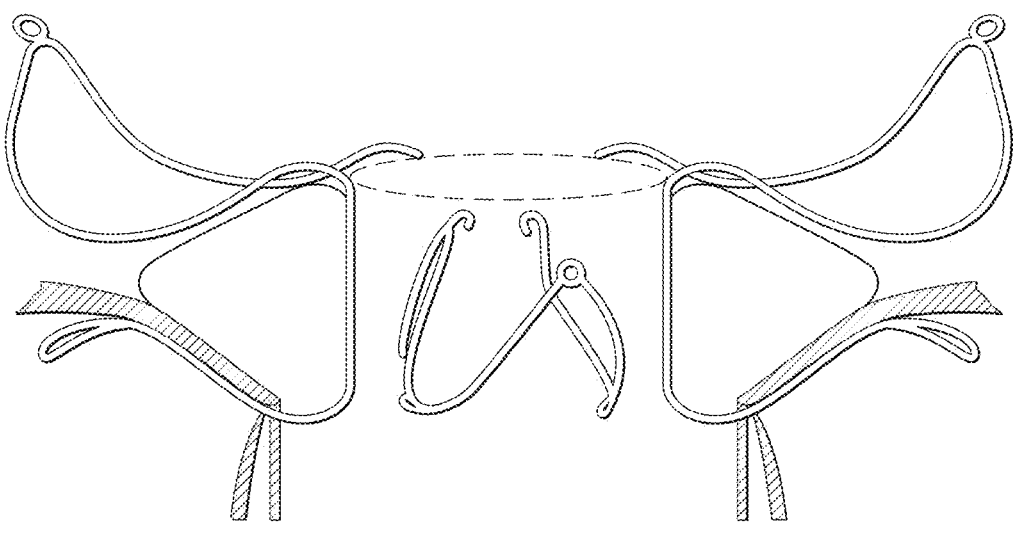
FIG. 56 is a perspective view of a prosthetic heart valve having an atrial set of arms that includes three arms, in accordance with an embodiment.

FIG. 55-FIG. 58 depict several alternate embodiments of a prosthetic heart valve. In FIG. 55, the atrial set of arms may be configured to expand into one or more native commissures of the native heart valve. FIG. 56 depicts an embodiment in which the atrial set of arms includes three arms. FIG. 57 and FIG. 58 depict an embodiment in which one or more arms of the ventricular set of arms is configured to contact a native leaflet on a ventricular side of the native leaflet at a distal portion of the one or more arms and is configured to contact a native leaflet on an atrial side of the native leaflet at a proximal portion of the one or more arms. The prosthetic heart valve of FIG. 57 and FIG. 58 may be further configured to include one or more ventricular covers, such as the ventricular cover of FIG. 16, configured to contact a native leaflet on the atrial side of the native leaflet.

In the embodiment of FIG. 3, the prosthetic heart valve includes two support structures wherein the atrial ends of the cylindrical portions of each support structure include a head portion with a single fenestration, wherein the two fenestrations are configured to be approximately coaxial, which may facilitate attachment of the at least two eyelets, for example by laser welding, riveting, suturing, or other means of attachment. In some embodiments, the atrial ends of the cylindrical portions of each support structure may have a bend such that the head portions are nearer to a central axis of the elongate central passageway of the cylindrical portions than an inner surface of the cylindrical portions of the support structures, which may facilitate entry into a catheter of a transcatheter delivery system, for example.

In the embodiment shown in FIG. 3, one or more of the arms of the atrial set of arms may have one or more eyelets on the proximal or distal segment of the one or more arms to facilitate deployment, positioning, and or recapture of the prosthetic heart valve, for example, by routing a suture through the eyelets for controlling the motion of the one or more arms. In some embodiments, the one or more eyelets may be fully closed which may be advantageous to prevent an attachment mechanism such as a suture from disengaging with the one or more eyelets. In another set of embodiments, the one or more eyelets may be open, which may be advantageous to allow an attachment mechanism to be easily engaged with or to allow disengagement with the one or more eyelets.

FIG. 59A shows an embodiment where the most distal segment of one or more of the arms of the atrial set of arms may have a curvature that extends back towards the same distal segment, such that the distal-most portion is substantially parallel to the portion of the distal segment where the curve originates. In this way, the distal segment forms a hook that is preferably open to allow an attachment mechanism such as a suture to be connected to the hook, although in some embodiments the hook may form a closed loop at the distal-most segment of one or more of the arms of the atrial set of arms. In some embodiments, the hook may have two or more openings, for example to allow more than one attachment mechanism such as a suture to be connected to the hook from different directions while preventing unintentional disengagement from the hook. In one set of embodiments, the one arm of the atrial set of arms that is shorter than the other arms of the atrial set of arms has a hook with a shape shown in FIG. 59B to allow sutures that originate from two different directions to be attached to the hook.

Figure 60:
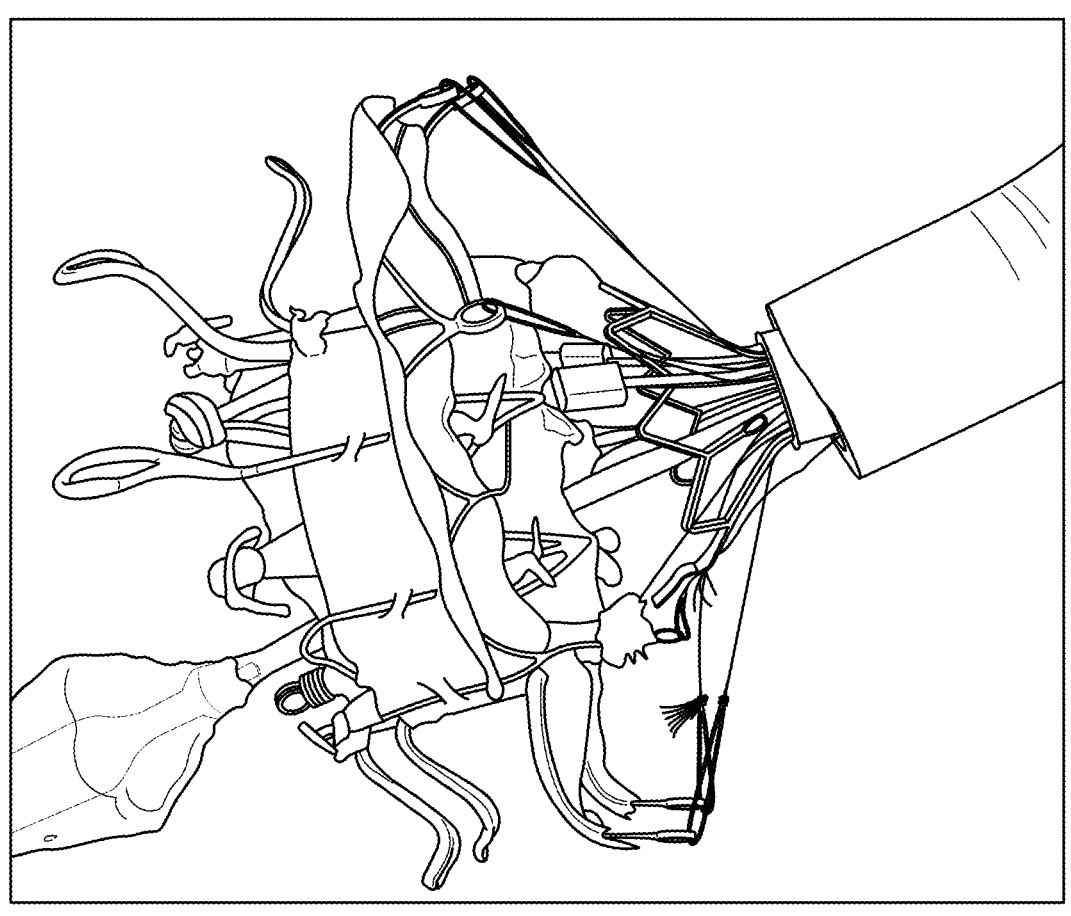
FIG. 60 is a perspective view of a prosthetic heart valve in an expanded configuration having thread-like elements, in accordance with an embodiment.

In some embodiments, the prosthetic heart valve may include one or more thread-like elements having a first end and a second end, wherein the first end may be configured to attach to a portion of a delivery system for the prosthetic heart valve and the second end may be configured to attach to a portion of the prosthetic heart valve. In the embodiment of FIG. 60, the one or more thread-like elements are attached to the hooks of the arms of the atrial set of arms of the prosthetic heart valve. The thread-like elements may be configured to transition the atrial set of arms from a compressed configuration to an expanded configuration, as shown in FIG. 60, and vice versa. In some embodiments, the thread-like elements are configured to be implanted in the native heart along with the prosthetic heart valve.

In some embodiments, the thread-like elements may be made from suture or other type of thread, string, wire, or line. In some embodiments, the thread-like elements may be bioabsorbable. In some embodiments, the thread-like elements may be made from a metal, such as Nitinol, stainless steel, or other flexible and biocompatible metal. In some embodiments, the thread-like elements may be Nitinol springs, which may be advantageous due to the superelastic properties of Nitinol which help resist plastic deformation of the thread-like elements when moving from a compressed configuration to an expanded or implanted configuration.

In some embodiments, the distal ends of the third set of arms (e.g., of a ventricular set of arms) extend farther radially than the embodiment of FIG. 9, which may be desirable to provide a larger sealing surface against which the native leaflets may contact. The arms of the ventricular set of arms may be symmetrical about the central axis of the elongate central passageway; however, in another set of embodiments, one or more arms of the ventricular set of arms may be of a different size, shape, or orientation, depending on the desired function.

In some embodiments, the support structure includes connecting members that extend from an atrial side of the support structure in an atrial direction. These connecting members may be used to connect to a delivery system to aid in delivery of the prosthetic heart valve to a native heart valve.

According to some embodiments, a ventricular cover for a ventricular set of arms, is configured to extend over an outer surface of at least one of the arms of the ventricular set of arms. In some embodiments, the ventricular cover encloses at least a portion of one or more of the third set of arms and is configured to contact an atrial side of a native leaflet. In some embodiments, the cover encloses at least a portion of one or more atrial-directed arms of the ventricular set of arms. For example, the cover may enclose a proximal portion of one or more arms of the ventricular set of arms, and an intermediate U-shaped portion of one or more arms of the atrial-directed ventricular set of arms that is distal to the proximal portion. In some embodiments, a ventricular set of arms does not have connecting members, and has a ventricular cover enclosing the ventricular set of arms.

In some embodiments, a support structure includes a cylindrical portion and an atrial set of arms, wherein the atrial set of arms are all of equal size, shape, and orientation. The atrial arms may be relatively short in length, in some embodiments, which may be advantageous to reduce the overall length of the prosthetic heart valve when in a compressed configuration, which may facilitate maneuvering of the prosthetic heart valve in the native heart prior to implantation.

Figure 61:
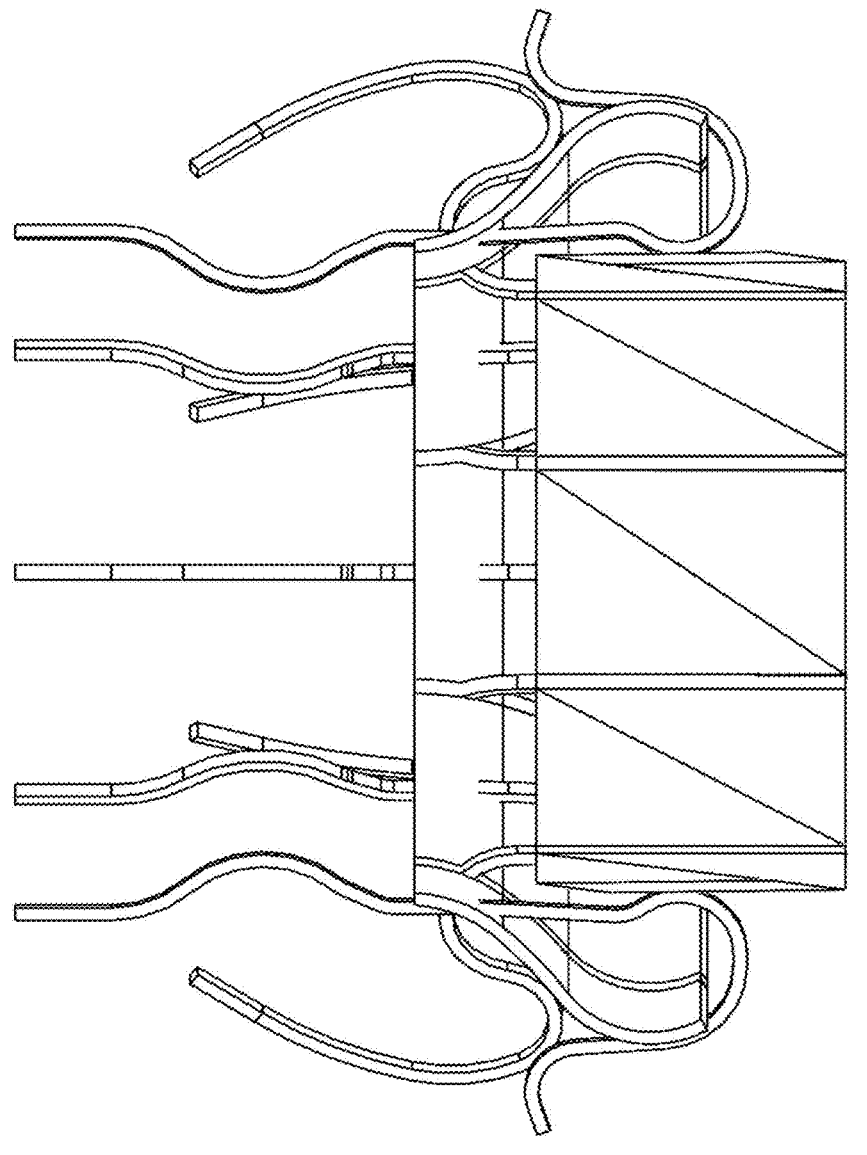
FIG. 61 is a side cross-sectional view of two support structures for a prosthetic heart valve, in accordance with an embodiment.

FIG. 61 depicts an embodiment of a prosthetic heart valve that includes a support structure and a ventricular set of arms.

In some embodiments, the third set of arms may be configured to extend in a ventricular direction beyond the ventricular-most portion of the atrial-directed arms of the ventricular set of arms. In some embodiments, the ventricular cover for the ventricular set of arms may be attached to a distal end of the third set of arms and thereby extend the ventricular cover farther in a ventricular direction beyond the ventricular-most portion of the atrial-directed arms, which may be advantageous to increase a surface area of the cover for preventing paravalvular leakage around the prosthetic heart valve.

In some embodiments, the third set of arms may be configured to extend in a radial direction radially beyond a distal portion of the atrial-directed arms of the ventricular set of arms, as depicted in FIG. 62A-62B. FIG. 62A shows a top view of an embodiment of a ventricular set of arms in which a cover for the ventricular set of arms has a contoured outer surface that extends radially beyond the distal portion of the atrial-directed arms between adjacent atrial-directed arms, thereby extending the ventricular cover closer towards the native leaflets, which may help prevent paravalvular leakage around the prosthetic heart valve. In some embodiments, a distal end of the third set of arms has a radial distance from the central axis of the elongate central passageway that is less than a radial distance between the distal portion of the atrial-directed arm and the central axis. In an illustrative embodiment, FIG. 62A depicts a side view of an atrial-directed arm of the ventricular set of arms superimposed over an annular-directed arm of the ventricular set of arms, wherein a distal end of the annular-directed arm has a radial distance from the central axis of the elongate central passageway that is greater than a radial distance between the distal portion of the atrial-directed arm and the central axis. As one of ordinary skill in the art will appreciate based upon the teachings of this specification, the arms depicted in FIG. 62A are not intended to be limiting and other arms from the third set of aims not necessarily annular-directed or atrial-directed may be present.

FIGS. 63A-63D depict several side views of an exemplary embodiments in which an atrial-directed arm is superimposed over an annular-directed arm wherein the annular-directed arms have different lengths, sizes, shapes, curvatures, or orientations.

Figure 64:
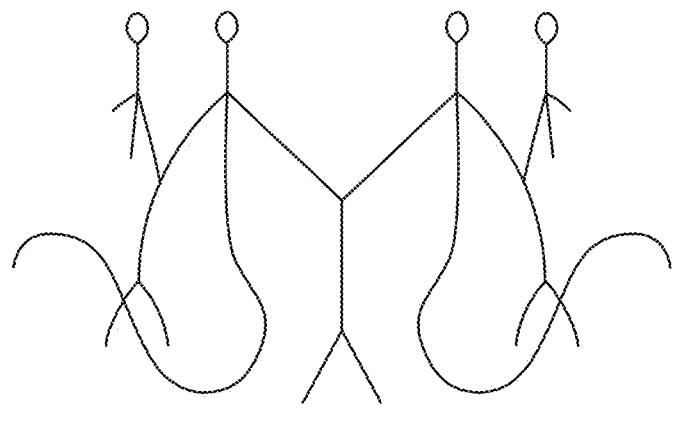
FIG. 64 depicts a side view of a ventricular set of arms, in accordance with an embodiment.
Figure 65:
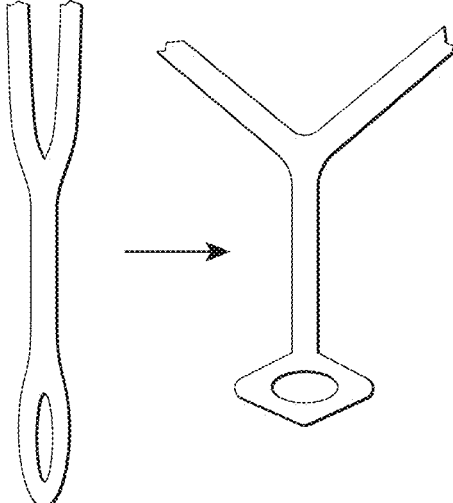
FIG. 65 depicts a side view of a collapsed and expanded arm of a ventricular set of arms, in accordance with an embodiment.

In some embodiments, the distal end of the third set of arms may have different shapes, such as a bifurcation, as demonstrated in the embodiment of FIG. 64. Depending on the embodiment, it may be desirable to provide additional radial extension of the ventricular cover between adjacent arms of the third set of arms. In some embodiments, the distal end of the third set of arms may have other shapes, such as the paddle-like shape depicted in FIG. 65. In some embodiments, the distal end of the third set of arms may have more than two extensions (e.g., three or four extending members). In some embodiments, the distal end of the annular-directed arms may be atraumatic to avoid damage to the surrounding tissue. In some embodiments, the distal end of the third set of arms may have one or more fenestrations or other features for facilitating attachment of one or more ventricular covers to the third set of arms. In some embodiments, the distal end of a first arm of the third set of arms may have a different length, size, shape, curvature, angle and/or orientation from a second arm of the third set of arms.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

It is understood that some or all steps, operations, or processes may be performed automatically, without the intervention of a user. Method claims may be provided to present elements of the various steps, operations or processes in a sample order, and are not meant to be limited to the specific order or hierarchy presented.

The Title, Background, Brief Description of the Drawings, and Claims of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it may be seen that the description provides illustrative examples and the various features are grouped together in various embodiments for the purpose of streamlining the disclosure. This method of disclosure is not to be interpreted as reflecting an intention that the claimed subject matter requires more features than are expressly recited in any claim. Rather, as the following claims s reflect, inventive subject matter lies in less than all features of a single disclosed configuration or operation. The following claims are hereby incorporated into the Detailed Description, with each claims standing on its own to represent separately claimed subject matter.

What is claimed is:

1. A prosthetic heart valve, comprising:
a support structure, wherein the support structure defines an elongate central passageway, wherein the support structure comprises one or more atrial arms, one or more ventricular arms, and a third set of arms;
a plurality of leaflet elements attached to the support structure and disposed within the elongate central passageway for control of blood flow through the elongate central passageway;
a cover formed separately from the support structure and supported by the third set of arms, the cover configured to contact a native leaflet of a native heart valve of a heart and reduce leakage around the prosthetic heart valve,
wherein the support structure is configured to biodynamically fix the prosthetic heart valve to the native leaflet of the native heart valve of the heart and is not fixed to a native annulus of the native heart valve of the heart,
wherein the one or more atrial arms and the one or more ventricular arms extend across a cross-sectional plane of a cylindrical portion of the support structure such that:
a distal segment of the one or more atrial arms and a distal segment of the one or more ventricular arms extend perpendicularly away from a central axis of the elongate central passageway and contact opposing sides of each native leaflet at locations radially inward from the native annulus such that at least a portion of each native leaflet is held radially away from the native annulus thereby permitting axial motion of the cylindrical portion of the support structure and the portion of each native leaflet, relative to the native annulus, and
wherein, during biodynamic movement of the prosthetic heart valve within the native heart valve during cardiac cycles of the heart, the ventricular arms are configured to resist the movement while the atrial arms maintain contact with native leaflets and/or the atrial arms resist the movement while the ventricular arms maintain contact with the native leaflets, such that systolic and/or diastolic pressure load is at least partially absorbed by the motion of the native leaflets.

2. The prosthetic heart valve of claim 1, wherein:
the at least one support structure comprises a cylindrical portion comprising an atrial end and a ventricular end, and
the elongate central passageway is defined by the cylindrical portion of the at least one support structure.

3. The prosthetic heart valve of claim 2, wherein:
each arm of the one or more atrial arms comprises a proximal atrial segment that is proximal to the cylindrical portion and a distal atrial segment that is distal to the cylindrical portion, and
at least one of a size, a shape, or an angle of a first atrial arm of the one or more atrial arms is different from a corresponding one of a size, a shape, or an angle of a second atrial arm of the one or more atrial arms.

4. The prosthetic heart valve of claim 3, wherein the size of the first atrial arm is greater than the size of the second atrial arm.

5. The prosthetic heart valve of claim 3, wherein:
the first atrial arm has a first length in a direction parallel to a longitudinal axis and the second atrial arm has a second length in the direction parallel to the longitudinal axis, and
the first length is greater than the second length.

6. The prosthetic heart valve of claim 5, wherein the first length is greater than the second length when the prosthetic heart valve is implanted in the heart.

7. The prosthetic heart valve of claim 5, wherein:
each arm of the one or more ventricular arms comprises a proximal ventricular segment that is proximal to the cylindrical portion and a distal ventricular segment that is distal to the cylindrical portion, and
at least one of a size, a shape, or an angle of a first ventricular arm is different from a corresponding one of a size, a shape, or an angle of a second ventricular arm.

8. The prosthetic heart valve of claim 7, wherein the size of the first ventricular arm is greater than the size of the second ventricular arm.

9. The prosthetic heart valve of claim 7, wherein:
the first ventricular arm has a first length in a direction parallel to the longitudinal axis and the second ventricular arm has a second length in the direction parallel to the longitudinal axis, and
the first length is greater than the second length.

10. The prosthetic heart valve of claim 9, wherein the first length is greater than the second length when the prosthetic heart valve is implanted in the heart.

11. The prosthetic heart valve of claim 7, wherein in an implanted configuration:
a first subset of the one or more ventricular arms is proximate to a ventricular side of a first the native leaflet, and
a second subset of the one or more ventricular arms is proximate to an atrial side of a second the native leaflet.

12. The prosthetic heart valve of claim 11, wherein, in the implanted configuration, at least one arm of a third subset of the one or more ventricular arms is proximate to at least one of: a commissure of the native heart or an atrial side of the first native leaflet.

13. The prosthetic heart valve of claim 12, wherein:
the at least one arm of the third subset has a first length in a direction parallel to a longitudinal axis of the prosthetic heart valve and another arm of the third subset has a second length in the direction parallel to the longitudinal axis, and the first length is greater than the second length.

14. The prosthetic heart valve of claim 11, wherein each arm of the first subset is configured such that the arms of the first subset, when in the implanted configuration, do not contact a native annulus of the heart, thereby reducing trauma to the heart.

15. The prosthetic heart valve of claim 7, wherein the cover is a ventricular cover disposed adjacent to a perimeter of the proximal ventricular segments, wherein the perimeter is opposite the cylindrical portion.

16. The prosthetic heart valve of claim 7, wherein the cover is a ventricular cover disposed adjacent to the proximal ventricular segments of the one or more ventricular arms, wherein a portion of the ventricular cover extends to be disposed adjacent to the distal ventricular segments of a subset of the one or more ventricular arms.

17. The prosthetic heart valve of claim 7, wherein the one or more ventricular arms is attached to an atrial end of the cylindrical portion of the at least one support structure.

18. The prosthetic heart valve of claim 3, wherein:

the distal atrial segment of the first atrial arm has a first distal end at a first distance from a longitudinal axis and a distal atrial segment of the second atrial arm has a second distal end at a second distance from the longitudinal axis, and the distal atrial segment of the first atrial arm extends relative to the longitudinal axis such that the first distance is less than the second distance.

19. The prosthetic heart valve of claim 3, further comprising:

an atrial cover comprising a plurality of distal atrial covers configured to be disposed adjacent to the distal atrial segments of the one or more atrial arms.

20. The prosthetic heart valve of claim 19, wherein the plurality of distal atrial covers comprise one or more pleats such that the plurality of distal atrial covers is configured to expand or contract as a corresponding one of the one or more atrial arms increases or decreases in length.

21. The prosthetic heart valve of claim 2, wherein the cylindrical portion of the at least one support structure is radially collapsible for transcatheter implantation.

22. The prosthetic heart valve of claim 1, wherein the cover is configured to contact an atrial side of the native leaflet.

23. The prosthetic heart valve of claim 1, wherein the cover is configured to contact a ventricular side of the native leaflet.

24. The prosthetic heart valve of claim 1, wherein a bend region of a distal segment of the third set of arms is configured such that a clamping force is exerted on the native leaflet.

\* \* \* \* \*